US011021545B2

(12) United States Patent
Kwon et al.

(10) Patent No.: US 11,021,545 B2
(45) Date of Patent: Jun. 1, 2021

(54) MULTIMODAL CANCER THERAPY COMPRISING CHIMERIC VIRAL/NONVIRAL NANOPARTICLES AND ANTICANCER AGENTS

(71) Applicant: The Regents of the University of California, Oakland, CA (US)

(72) Inventors: Young Jik Kwon, Irvine, CA (US); Margaret Lugin, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/528,305

(22) Filed: Jul. 31, 2019

(65) Prior Publication Data
US 2020/0040100 A1 Feb. 6, 2020

Related U.S. Application Data

(60) Provisional application No. 62/712,956, filed on Jul. 31, 2018.

(51) Int. Cl.
| | |
|---|---|
| C07H 21/02 | (2006.01) |
| C07H 21/04 | (2006.01) |
| C07K 16/30 | (2006.01) |
| C07K 16/40 | (2006.01) |
| C07K 16/32 | (2006.01) |
| C12N 15/113 | (2010.01) |
| C07K 14/47 | (2006.01) |
| C12N 15/52 | (2006.01) |
| A61K 31/7105 | (2006.01) |
| A61K 45/06 | (2006.01) |

(52) U.S. Cl.
CPC ...... *C07K 16/3007* (2013.01); *A61K 31/7105* (2013.01); *C07K 14/4746* (2013.01); *C07K 14/4747* (2013.01); *C07K 16/3053* (2013.01); *C07K 16/3092* (2013.01); *C07K 16/32* (2013.01); *C07K 16/40* (2013.01); *C12N 15/113* (2013.01); *C12N 15/1135* (2013.01); *C12N 15/52* (2013.01); *A61K 45/06* (2013.01); *C12N 2310/14* (2013.01); *C12N 2320/30* (2013.01)

(58) Field of Classification Search
CPC ............ C12N 2320/30; C12N 2310/14; C12N 15/113
See application file for complete search history.

(56) References Cited

U.S. PATENT DOCUMENTS 9,708,605 B2 * 7/2017 Brown ................ C12N 15/1135
2017/0355686 A1 * 12/2017 Dasgupta ............. C07D 413/12

FOREIGN PATENT DOCUMENTS

WO WO 2012/082074 A1 * 6/2012 ........... C12N 15/111

OTHER PUBLICATIONS

Cho et al. (Biomaterials, 33, 2012, 3316-3323).*
Hong et al. (J. Am. Chem. Soc., 2013, 135, 17655-17658).*
Panuzzo et al. (PLoS One, 2014, 9(10):e110682, 1-4).*
Brossartetal. (Cancer Research, 61, 6846-6850, 2001).*
Agarwal et al., "Effects of plerixafor in combination with BCR-ABL kinase inhibition in a murine model of CML." Blood, 120(13):2658-2668 (2012).
An et al., "BCR-ABL tyrosine kinase inhibitors in the treatment of Philadelphia chromosome positive chronic myeloid leukemia: A review." Leukemia Research 34:1255-1268 (2010).
Ashtari et al., "The human visual cortex responds to gene therapy—mediated recovery of retinal function." J Clin Invest. 121(6):2160-2168 (2011).
Balabanov et al., "Current aspects in resistance against tyrosine kinase inhibitors in chronic myelogenous leukemia." Drug Discovery Today: Technologies, 11:89-99 (2014).
Benskey et al., "Targeted Gene Delivery to the Enteric Nervous System Using AAV: A Comparison Across Serotypes and Capsid Mutants." Molecular Therapy 23(3):488-500 (2015).
Bignell et al., "Signatures of mutation and selection in the cancer genome." Nature 463(18):893-900 (2000).
Bixby et al., "Seeking the causes and solutions to imatinib-resistance in chronic myeloid leukemia." Leukemia 25:7-22 (2011).
Carlisle et al., "Coating of adeno-associated virus with reactive polymers can ablate virus tropism, enable retargeting and provide resistance to neutralising antisera." J Gene Med 10:400-411 (2008).
Cho et al., "Polyamine/DNA polyplexes with acid-degradable polymeric shell as structurally and functionally virus-mimicking nonviral vectors." Journal of Controlled Release 150:287-297 (2011).
Cho et al., "Simultaneous gene transduction and silencing using stimuli-responsive viral/nonviral chimeric nanoparticles." Biomaterials 33:3316-3323 (2012).
Cho et al., "Synthetically engineered viruses: Can synthetic chemistry tame the nature?" Current Opinion in Solid State and Materials Science 16:276-286 (2012).
Cho et al., "Acid-degradable Core-shell Nanoparticles for Reversed Tamoxifen-resistance in Breast Cancer by Silencing Manganese Superoxide Dismutase (MnSOD)." Biomaterials. 34(38):10228-10237 (2013).
Cohen et al., "Approval Summary for Imatinib Mesylate Capsules in the Treatment of Chronic Myelogenous Leukemia." Clinical Cancer Research 8:935-942 (2002).
Contreras-Ruiz et al., "Intracellular trafficking of hyaluronic acid-chitosan oligomer based nanoparticles in cultured human ocular surface cells". Molecular Vision 7:279-290 (2011).
Corbin et al., "Several BCR-ABL kinase domain mutants associated with imatinib mesylate resistance remain sensitive to imatinib." Bilood 101,(11):4611-4614 (2003).

(Continued)

*Primary Examiner* — Amy H Bowman
(74) *Attorney, Agent, or Firm* — Gavrilovich, Dodd & Lindsey LLP

(57) ABSTRACT

The disclosure provides for a multimodal cancer therapy comprising chimeric viral/nonviral nanoparticles and anticancer agents and uses thereof to treat a subject with cancer or suspected of having a cancer.

13 Claims, 32 Drawing Sheets

(56) References Cited

OTHER PUBLICATIONS

Costa et al., "The Impact of EGFR T790M Mutations and BIM mRNA Expression on Outcome in Patients with EGFR-Mutant NSCLC Treated with Erlotinib or Chemotherapy in the Randomized Phase III EURTAC Trial." Clin Cancer Res; 20(7)2001-2010 (2014).
Cragg et al. "Treatment of B-RAF mutant human tumor cells with a MEK inhibitor requires Bim and is enhanced by a BH3 mimetic." Clin Invest. 118(11):3651-3659 (2008).
Daley et al., "Induction of Chronic Myelo^enous Leukemia in Mice by the P210 cr/a Gene of the Philadelphia Chromosome." Science 247(4944):824-830 (1990).
Dalkara et al., "In Vivo-Directed Evolution of a New Adeno-Associated Virus for Therapeutic Outer Retinal Gene Delivery from the Vitreous." Sci Transl Med 5:189ra76 (2013).
Davies et al., "Mutations of the BRAF gene in human cancer." Nature 417:949-954 (2002).
Daya et al., "Adeno-Associated Virus Site-Specific Integration Is Mediated by Proteins of the Nonhomologous End-Joining Pathway." Journal of Virology 83(22):11655-11664 (2009).
Deininger et al., "The molecular biology of chronic myeloid leukemia." Blood 96(10):3343-3356 (2000).
Dias et al., "Molecular genetics and emerging therapies for retinitis pigmentosa: Basic research and clinical perspectives." Progress in Retinal and Eye Research 63:107-131 (2018).
Druker et al., "Activity of a specific inhibitor of the BCL-ABL tyrosine kinase in the blast crisis of chronic myeloid leukemia and acute lyphoblastic leukemia with the Philadelphia chromosome." N Engl J Med 344(14):1038-1042 (2001).
Druker et al., "Efficacy and safety of a specific inhibitor of the BCR-ABL tyrosine kinase in chronic myeloid leukemia." N Engl J Med 344(14):1031-1037 (2001).
Essafi et al., "Direct transcriptional regulation of Bim by FoxO3a mediates STI571-induced apoptosis in Bcr-Abl-expressing cells." Oncogene 24:2317-2329 (2005).
Faber et al., "BIM Expression in Treatment-Naïve Cancers Predicts Responsiveness to Kinase Inhibitors." Cancer Discovery 1:352-365 (2011).
Gillings et al., "Apoptosis and autophagy: BIM as a mediator of tumour cell death in response to oncogene-targeted therapeutics." FEBS Journal 276:6050-6062 (2009).
Glaysher et al., "Targeting EGFR and PI3K pathways in ovarian cancer". British Journal of Cancer 109:1786-1794 (2013).
Gschwantler-Kaulich et al., "HER Specific TKIs Exert Their Antineoplastic Effects on Breast Cancer Cell Lines through the Involvement of STAT5 and JNK." PLoS ONE 11(1): e0146311 (2016).
Gschwind et al., "The discovery of receptor tyrosine kinases: targets for cancer therapy." Nature Reviews 4:361-370 (2004).
Han et al., "Interrelated Roles for Mcl-1 and BIM in Regulation of TRAIL-mediated Mitochondrial Apoptosis." The Journal of Biological Chemistry 281(15): 10153-10163 (2006).
He et al., "Functions of flt3 in zebrafish hematopoiesis and its relevance to human acute myeloid leukemia." Blood 123(16)2518-2529 (2014).
Herzog et al. "AAV Vector Biology in Primates: Finding the Missing Link?" Molecular Therapy 19(11):1923-1924 (2011).
Hong et al., "Viral/Nonviral Chimeric Nanoparticles to Synergistically Suppress Leukemia Proliferation via Simultaneous Gene Transduction and Silencing." ACS Nano. 10(9): 8705-8714 (2016).
Hong et al., "Functional Nanostructures for Effective Delivery of Small Interfering RNA Therapeutics." Theranostics 4 (12)1211-1232 (2014).
Iwamoto et al. "Challenges of Drug Delivery Systems That Contribute to Cancer Chemotherapy." Biol. Pharm. Bull. 36(5):715-718 (2013).
Jacquemin et al., "Quercetin-mediated MGM and survivin downregulation restores TRAIL-induced apoptosis in non-Hodgkin's lymphoma B cells." haematologica 97(1):38-46 (2012).
Jorgensen et al., "MLL AT-hook sequence is strongly conserved in infant acute leukemia with or without MLL gene rearrangement." Leukemia 17:1432-1433 (2003).
Kanasty et al., "Delivery materials for siRNA therapeutics." Nature Materials 12:967-977 (2013).
Kaplan et al., "Another tyrosine kinase inhibitor-resistance mutation within the BCR-ABL kinase domain: chasing our tails?" Lymphoma, 58(7):1526-1527 (2017).
Kervala et al., "Evaluating AAV Hybrid Variants for Improved Tropism after Intravitreal Gene Delivery to the Retina." Molecular Therapy vol. 23(1):S127-S128 (2015).
Kim et al., "The effect of surface modification of adenovirus with an arginine-grafted bioreducible polymer on ransduction efficiency and immunogenicity in cancer gene therapy." Biomaterials 31:1865-1874 (2010).
Kindler et al., "FLT3 as a therapeutic target in AML: still challenging after all these years." Blood 116 (24):5089-5102 (2012).
Kiyota et al. "FTY720 induces apoptosis of chronic myelogenous leukemia cells via dual activation of BIM and BID and overcomes various types of resistance to tyrosine kinase inhibitors." Apoptosis 18:1437-1446 (2013).
Koldenhoff et al., "Additive antileukemia effects by GFI1B- and BCR—ABL-specific siRNA in advanced phase chronic myeloid leukemic cells." Cancer Gene Therapy 20:421-427 (2013).
Kolosenko et al., "Identification of novel small molecules that inhibit STAT3-dependent transcription and function." PLoS ONE 12(6): e0178844 (2017).
Koo et al., "The movement of self-assembled amphiphilic polymeric nanoparticles in the vitreous and retina after intravitreal injection." Biomaterials 33:3485e3493 (2012).
Koss et al., "Requirement for antiapoptotic MCL-1 in the survival of BCR-ABL B-lineage acute lymphoblastic leukemia." Blood 122(9):1587-1598 (2017).
Kotterman et al., "Antibody Neutralization Poses a Barrier to Intravitreal Adeno-Associated Viral Vector Gene Delivery to Non-Human Primates." Gene Ther. 22(2):116-126 (2015).
Silvassy et al., "Quantitative assay for totipotent reconstituting hematopoietic stem cells by a competitive repopulation strategy." PNAS 87:8736-8740 (1990).
Taswell et al., "Limiting Dilution Assays for the Determination of Immunocompetent Cell Frequencies. JIIT. Validity Tests for the Single-Hit Poisson Model." Journal of Immunological Methods 72:29-40 (1984).
Wang et al., "Apoptosis drives cancer cells proliferate and metastasize." J. Cell. Mol. Med. 17(1):205-211 (2013).
Ward et al., "Targeted integration of a rAAV vector into the AAVS1 region." Virology 433:356-366 (2012).
Wei et al., "Conjugation of paclitaxel on adeno-associated virus (AAV) nanoparticles for co-delivery of genes and drugs." European Journal of Pharmaceutical Sciences 46:167-172 (2012).
Wen et al., "Delivery of AAV9 cyclin-A2 via hyaluronic acid hydrogel induces cardiac regeneration as well as improves cardiac function in vivo post mycardial infarction." Heart 99(Suppl 3):e1-e302 (2013).
Wojcicki et al., "Hyaluronic acid-bearing lipoplexes: Physicochemical characterization and in vitro targeting of the CD44 receptor." J Control Release 62(3):545-52 (2012).
Wu et al., "BCR/ABL oncogene-induced PI3K signaling pathway leads to chronic myeloid leukemia pathogenesis by impairing immuno-modulatory function of hemangioblasts." Cancer Gene Therapy 22:227-237 (2015).
Yin et al., "Non-viral vectors for gene-based therapy." Nature Reviews Genetics 15:541-555 (2014).
Yoshida et al., "The Potential Benefits of BIM in the Further Pursuit of Biomarker Discovery in Cancer Therapeutics." Cancer Discovery 1(4):289-90 (2011).
Zamora et al., "Photochemical internalization mediated nonviral gene transfection: polyamine core-shell nanoparticles as gene carrier." Journal of Biomedical Optics 19(10):105009 (2014).
Kotterman et al., "Engineering adeno-associated viruses for clinical gene therapy" Nat Rev Genet. 15(7): 445-451 (2014).
Krause et al., "Tyrosine Kinases as Targets for Cancer Therapy." N Engl J Med 353:172-87 (2005).

(56) References Cited

OTHER PUBLICATIONS

Kreppel et al., "Modification of Adenovirus Gene Transfer Vectors With Synthetic Polymers: A Scientific Review and Technical Guide." Molecular Therapy 16(1):16-29 (2008).
Kuribara et al., "Roles of Bim in Apoptosis of Normal and Bcr-Abl-Expressing Hematopoietic Progenitors." Molecular and Cellular Biology 24(14):6172-6183 (2004).
Kurioka et al., "Hyaluronic acid pretreatment for Sendai virus-mediated cochlear gene transfer." Gene Therapy 23:187-195 (2016).
Kwon et al., "Directed Antigen Presentation Using Polymeric Microparticulate Carriers Degradable at Lysosomal pH or Controlled Immune Responses" Molecular Pharmaceutics 2(1):83-91 (2004).
Kwon et al., "In vivo targeting of dendritic cells for activation of cellular immunity using vaccine carriers based on pH-responsive microparticles." PNAS 102(51):18264-18268 (2005).
Laurent et al., "The BCR Gene and Philadelphia Chromosome-positive Leukemogenesis." Cancer Research 61:2343-2355 (2001).
Leaver et al., "Cooperative effects of bcl-2 and AAV-mediated expression of CNTF on retinal ganglion cell survival and axonal regeneration in adult transgenic mice." European Journal of Neuroscience, vol. 24:3323-3332 (2006).
Lee et al., "Targeted cellular delivery of robust enzyme nanoparticles for the treatment of drug-induced hepatotoxicity and liver injury". Acta Biomaterialia 81:231-241 (2018).
Lee et al., "PEG Conjugation Moderately Protects Adeno-Associated Viral Vectors Against Antibody Neutralization." Biotechnology and Bioengineering 92(1):25-34 (2005).
Lee et al., "Anti-VEGF PolysiRNA Polyplex for the Treatment of Choroidal Neovascularization." Mol. Pharmaceutics 13:1988-1995 (2016).
Lee et al., "Development of efficient adeno-associated virus (AAV)-mediated gene delivery system with a phytoactive material for targeting human melanoma cells." New Biotechnology 37:194-199 (2017).
Lowenstein et al., "Immune Responses to Adenovirus and Adeno-Associated Vectors Used for Gene Therapy of Brain Diseases: The Role of Immunological Synapses in Understanding the Cell Biology of Neuroimmune Interactions." Curr Gene Ther. 7(5): 347-360 (2007).
Luo et al., "Dasatinib (BMS-354825) Pharmacokinetics and Pharmacodynamic Biomarkers in AnimalModels Predict optimal Clinical Exposure." Clin Cancer Res 12(23):7180-7186 (2006).
Lwin et al., "Follicular dendritic cell-dependent drug resistance of non-Hodgkin lymphoma involves cell adhesion-Tiediated Bim down-regulation through induction of microRNA-181a." Blood 116(24):5228-5236 (2010).
Martens et al., "Effect of hyaluronic acid-binding to lipoplexes on intravitreal drug delivery for retinal gene therapy." European Journal of Pharmaceutical Sciences 103:27-35 (2017).
McAllister et al., "The tumour-induced systemic environment as a critical regulator of cancer progression and metastasis." Nat Cell Biol. 16(8): 717-727 (2014).
Melo et al., "The Diversity of BCR-ABL Fusion Proteins and Their Relationship to Leukemia Phenotype." Blood 88 (7): 2375-2384 (1996).
Mingozzi et al., "Immune responses to AAV vectors: overcoming barriers to successful gene therapy." Blood 122 (1):23-36 (2013).
Mingozzi et al., "Therapeutic in vivo gene transfer for genetic disease using AAV: progress and challenges." Nature Reviews Genetics 12:341-355 (2011).
Mohamed et al., "The Effect of Imatinib Mesylate on Patients with Philadelphia Chromosome-positive Chronic Myeloid Leukemia with Secondary Chromosomal Aberrations." Clinical Cancer Research 9:1333-1337 (2003).
Nakagawa et al., "EGFR-TKI Resistance Due to BIM Polymorphism Can Be Circumvented in Combination with HDAC Inhibition." Cancer REs 73(8):2428-2434 (2013).

Nathwani et al., "Adenovirus-Associated Virus Vector—Mediated Gene Transfer in Hemophilia B." The New England Journal of Medicine 365:2357-2365 (2011).
Notta et al., "Evolution of human BCR-ABL1 lymphoblastic leukaemia-initiating cells." Nature 469(7330):362-7 (2011).
O'Hare et al., "Targeting the BCR-ABL Signaling Pathway in Therapy-Resistant Philadelphia Chromosome-Positive Leukemia." Clin Cancer Res 17(2):212-21 (2011).
Perciavalle et al., "Anti-Apoptotic MCL-1 Localizes to the Mitochondrial Matrix and Couples Mitochondrial Fusion to Respiration." Nat Cell Biol. 14(6): 575-583 (2012).
Potter et al., "BMX Acts Downstream of PI3K to Promote Colorectal Cancer Cell Survival and Pathway Inhibition Sensitizes to the BH3 Mimetic ABT-737." Neoplasia 16(2):147-157 (2014).
Qiang et al., "Mechanisms of resistance to the BCR-ABL1 allosteric inhibitor asciminib." Leukemia 31:2844-2847 (2017).
Qin et al., "Hyaluronic acid-modified cationic niosomes for ocular gene delivery: improving transfection efficiency in retinal pigment epithelium." Journal of Pharmacy and Pharmacology 70:1139-1151 (2018).
Ran et al., "Enhanced gene delivery efficiency of cationic liposomes coated with PEGylated hyaluronic acid for anti P-glycoprotein siRNA: A potential candidate for overcoming multi-drug resistance." International Journal of Pharmaceutics 477:590-600 (2014).
Roeder et al., "Dynamic modeling of imatinib-treated chronic myeloid leukemia: functional insights and clinical implications." Nature Medicine 12(10):1181-1184 (2006).
Rubert et al., "Bim and Mcl-1 exert key roles in regulating JAK2V617F cell survival." BMC Cancer 11:24 (2011).
Salmon et al., "Safety profile of recombinant adeno-associated viral vectors: focus on alipogene tiparvovec (Glybera)." Expert Rev. Clin. Pharmacol. 7(1):53-65 (2014).
Schultz et al., "Recombinant Adeno-associated Virus Transduction and Integration." Molecular Therapy 16(7): 1189-1199 (2008).
Shao et al., "A novel polyethyleneimine-coated adeno associatedvirus-like particle formulation for efficient siRNA delivery in breast cancer therapy: preparation and in vitro analysis." International Journal of Nanomedicine 7:1575-1586 (2012).
Shet et al., "Chronic myelogenous leukemia: mechanisms underlying disease progression." Leukemia 16:1402-1411 (2002).
Shibata et al., "Hyaluronic Acid Enhances Gene Delivery into the Cochlea." Human Gene Therapy 23:302-310 (2012).
Shim et al., "Acid-Responsive Linear Polyethylenimine for Efficient, Specific, and Biocompatible siRNA Delivery." Bioconjugate Chem. 20:488-499 (2009).
Shim et al., "Controlled Delivery of Plasmid DNA and siRNA to Intracellular Targets Using Ketalized Polyethylenimine." Biomacromolecules 9:444-455 (2008).
Shim et al., "Acid-transforming polypeptide micelles for targeted nonviral gene delivery." Biomaterials 31:3404-3413 (2010).
Shim et al., "Dual mode polyspermine with tunable degradability for plasmid DNA and siRNA delivery." Biomaterials 32:4009-4020 (2011).
Shim et al., "Stimuli-responsive siRNA carriers for efficient gene silencing in tumors via systemic delivery." Biomater. Sci. 2:35-40 (2014).
Shim et al., "Controlled cytoplasmic and nuclear localization of plasmid DNA and siRNA by differentially tailored polyethylenimine." Journal of Controlled Release 133:206-213 (2009).
Shim et al., "Ketalized poly(amino ester) for stimuli-responsive and biocompatible gene delivery." Polym. Chem. 3:2570-2577 (2012).
Shukla et al., "Synthesis and characterization of a BODIPY conjugate of the BCR-ABL kinase inhibitor Tasigna® (Nilotinib): Evidence for transport of Tasigna® and its fluorescent derivative by ABC drug transporters." Mol Pharm. 8(4):1292-1302 (2011).
Soverini et al., "BBCR-ABL kinase domain mutation analysis in chronic myeloid leukemia patients treated with tyrosine kinase inhibitors: recommendations from an expert panel on behalf of European LeukemiaNet." Blood 118 (5):1208-15 (2011).
Standley et al., "Acid-Degradable Particles for Protein-Based Vaccines: Enhanced Survival Rate for Tumor-Challenged Mice Using Ovalbumin Model." Bioconjugate Chem. 15:1281-1288 (2004).

(56) References Cited

OTHER PUBLICATIONS

Sunshine et al., "Uptake and transfection with polymeric nanoparticles are dependent on polymer end-group structure, but largely independent of nanoparticle physical and chemical properties." Mol Pharm. 9(11): 3375-3383 (2012).

Suwan et al., "Hybrid AAV/Phage Vector Enhances Chemotherapy Efficacy Against Cancer." Molecular Therapy 24(1):S265-S266 (2016).

\* cited by examiner

| Entrez Gene ID | Current Symbol | Refseq Transcript |
|---|---|---|
| 25 | ABL1 | NM_007313 NM_005157 |
| 134 | ADORA1 | NM_000674 NM_001048230 |
| 135 | ADORA2A | NM_000675 |
| 142 | PARP1 | NM_001618 |
| 143 | PARP4 | NM_006437 |
| 148 | ADRA1A | NM_033304 NM_033303 NM_033302 NM_000680 |
| 186 | AGTR2 | NM_000686 |
| 196 | AHR | NM_001621 |
| 199 | AIF1 | NM_001623 NM_032955 |
| 207 | AKT1 | NM_001014431 NM_005163 NM_001014432 |
| 208 | AKT2 | NM_001626 |
| 239 | ALOX12 | NM_000697 |
| 317 | APAF1 | NM_013229 NM_181868 NM_181861 NM_181869 NM_001160 |
| 318 | NUDT2 | NM_147172 NM_001161 NM_147173 |
| 328 | APEX1 | NM_080649 NM_080648 NM_001641 |
| 329 | BIRC2 | NM_001166 |
| 330 | BIRC3 | NM_182962 NM_001165 |
| 331 | BIRC4 | NM_001167 |
| 332 | BIRC5 | NM_001012271 NM_001168 NM_001012270 |
| 333 | APLP1 | NM_001024807 NM_005166 |
| 351 | APP | NM_201413 NM_201414 NM_000484 |
| 355 | FAS | NM_152871 NM_152877 NM_000043 NM_152876 NM_152874 NM_152873 NM_152875 NM_152872 |
| 356 | FASLG | NM_000639 |
| 387 | RHOA | NM_001664 |
| 388 | RHOB | NM_004040 |
| 472 | ATM | NM_000051 NM_138292 |
| 572 | BAD | NM_004322 NM_032989 |
| 573 | BAG1 | NM_004323 |
| 578 | BAK1 | NM_001188 |
| 580 | BARD1 | NM_000465 |
| 581 | BAX | NM_004324 NM_138764 NM_138763 NM_138761 NM_138765 |
| 596 | BCL2 | NM_000657 NM_000633 |
| 597 | BCL2A1 | NM_004049 |
| 598 | BCL2L1 | NM_138578 NM_001191 |
| 599 | BCL2L2 | NM_004050 |
| 602 | BCL3 | NM_005178 |
| 604 | BCL6 | NM_138931 NM_001706 |
| 608 | TNFRSF17 | NM_001192 |
| 627 | BDNF | NM_170733 NM_170734 NM_170731 NM_001709 NM_170735 NM_170732 |
| 637 | BID | NM_001196 NM_197966 NM_197967 |
| 638 | BIK | NM_001197 |
| 652 | BMP4 | NM_130850 NM_130851 NM_001202 |
| 662 | BNIP1 | NM_013979 NM_013978 NM_001205 NM_013980 |
| 663 | BNIP2 | NM_004330 |
| 664 | BNIP3 | NM_004052 |

FIG. 19

| Entrez Gene ID | Current Symbol | Refseq Transcript |
|---|---|---|
| 666 | BOK | NM_032515 |
| 672 | BRCA1 | NM_007300 NM_007297 NM_007304 NM_007294 NM_007296 NM_007299 NM_007303 NM_007302 NM_007295 NM_007298 NM_007305 |
| 673 | BRAF | NM_004333 |
| 695 | BTK | NM_000061 |
| 727 | C5 | NM_001735 |
| 729 | C6 | NM_000065 |
| 730 | C7 | NM_000587 |
| 731 | C8A | NM_000562 |
| 732 | C8B | NM_000066 |
| 733 | C8G | NM_000606 |
| 735 | C9 | NM_001737 |
| 823 | CAPN1 | NM_005186 |
| 827 | CAPN6 | NM_014289 |
| 834 | CASP1 | NM_033293 NM_033292 NM_001223 NM_033295 NM_033294 |
| 835 | CASP2 | NM_032983 NM_032982 |
| 836 | CASP3 | NM_032991 NM_004346 |
| 837 | CASP4 | NM_001225 NM_033306 |
| 838 | CASP5 | NM_004347 |
| 839 | CASP6 | NM_001226 NM_032992 |
| 840 | CASP7 | NM_001227 NM_033339 NM_033338 NM_033340 |
| 841 | CASP8 | NM_001080125 NM_033355 NM_033358 NM_033356 NM_001080124 NM_001228 |
| 842 | CASP9 | NM_001229 NM_032996 |
| 843 | CASP10 | NM_001230 NM_032977 NM_032974 |
| 857 | CAV1 | NM_001753 |
| 858 | CAV2 | NM_001233 NM_198212 |
| 867 | CBL | NM_005188 |
| 914 | CD2 | NM_001767 |
| 922 | CD5L | NM_005894 |
| 929 | CD14 | NM_000591 NM_001040021 |
| 939 | CD27 | NM_001242 |
| 940 | CD28 | NM_006139 |
| 943 | TNFRSF8 | NM_001243 NM_152942 |
| 944 | TNFSF8 | NM_001244 |
| 949 | SCARB1 | NM_001082959 NM_005505 |
| 952 | CD38 | NM_001775 |
| 958 | CD40 | NM_001250 NM_152854 |
| 959 | CD40LG | NM_000074 |
| 970 | CD70 | NM_001252 |
| 984 | CDC2L1 | NM_033488 NM_033492 NM_033486 NM_033489 NM_033487 NM_033493 |
| 993 | CDC25A | NM_201567 NM_001789 |
| 1026 | CDKN1A | NM_078467 NM_000389 |
| 1029 | CDKN2A | NM_000077 NM_058195 NM_058197 |
| 1032 | CDKN2D | NM_079421 NM_001800 |
| 1082 | CGB | NM_000737 |

FIG. 19 (cont'd)

| Entrez Gene ID | Current Symbol | Refseq Transcript |
| --- | --- | --- |
| 1147 | CHUK | NM_001278 |
| 1149 | CIDEA | NM_001279 NM_198289 |
| 1191 | CLU | NM_001831 NM_203339 |
| 1201 | CLN3 | NM_001042432 NM_000086 |
| 1268 | CNR1 | NM_016083 NM_033181 |
| 1269 | CNR2 | NM_001841 |
| 1270 | CNTF | NM_000614 |
| 1432 | MAPK14 | NM_139012 NM_139014 NM_139013 NM_001315 |
| 1434 | CSE1L | NM_001316 |
| 1499 | CTNNB1 | NM_001098210 NM_001904 NM_001098209 |
| 1509 | CTSD | NM_001909 |
| 1537 | CYC1 | NM_001916 |
| 1603 | DAD1 | NM_001344 |
| 1611 | DAP | NM_004394 |
| 1612 | DAPK1 | NM_004938 |
| 1613 | DAPK3 | NM_001348 |
| 1616 | DAXX | NM_001350 |
| 1630 | DCC | NM_005215 |
| 1647 | GADD45A | NM_001924 |
| 1649 | DDIT3 | NM_004083 |
| 1676 | DFFA | NM_004401 NM_213566 |
| 1677 | DFFB | NM_004402 |
| 1773 | DNASE1 | NM_005223 |
| 1776 | DNASE1L3 | NM_004944 |
| 1777 | DNASE2 | NM_001375 |
| 1793 | DOCK1 | NM_001380 |
| 1848 | DUSP6 | NM_022652 NM_001946 |
| 1849 | DUSP7 | NM_001947 |
| 1869 | E2F1 | NM_005225 |
| 1871 | E2F3 | NM_001949 |
| 1875 | E2F5 | NM_001083589 NM_001951 NM_001083588 |
| 1982 | EIF4G2 | NM_001418 NM_001042559 |
| 2012 | EMP1 | NM_001423 |
| 2013 | EMP2 | NM_001424 |
| 2014 | EMP3 | NM_001425 |
| 2033 | EP300 | NM_001429 |
| 2068 | ERCC2 | NM_000400 |
| 2071 | ERCC3 | NM_000122 |
| 2081 | ERN1 | NM_152461 NM_001433 |
| 2147 | F2 | NM_000506 |
| 2149 | F2R | NM_001992 |
| 2175 | FANCA | NM_001018112 NM_000135 |
| 2185 | PTK2B | NM_004103 NM_173176 NM_173175 NM_173174 |
| 2277 | FIGF | NM_004469 |
| 2308 | FOXO1 | NM_002015 |
| 2309 | FOXO3 | NM_001455 NM_201559 |
| 2355 | FOSL2 | NM_005253 |
| 2549 | GAB1 | NM_002039 NM_207123 |

FIG. 19 (cont'd)

| Entrez Gene ID | Current Symbol | Refseq Transcript |
|---|---|---|
| 2620 | GAS2 | NM_005256 NM_177553 |
| 2668 | GDNF | NM_199231 NM_000514 NM_199234 |
| 2765 | GML | NM_002066 |
| 2876 | GPX1 | NM_201397 NM_000581 |
| 2879 | GPX4 | NM_002085 NM_001039847 NM_001039848 |
| 2885 | GRB2 | NM_002086 NM_203506 |
| 2932 | GSK3B | NM_002093 |
| 2934 | GSN | NM_000177 NM_198252 |
| 2936 | GSR | NM_000637 |
| 2944 | GSTM1 | NM_000561 NM_146421 |
| 2950 | GSTP1 | NM_000852 |
| 2953 | GSTT2 | NM_000854 |
| 2999 | GZMH | NM_033423 |
| 3001 | GZMA | NM_006144 |
| 3002 | GZMB | NM_004131 |
| 3004 | GZMM | NM_005317 |
| 3064 | HD | NM_002111 |
| 3065 | HDAC1 | NM_004964 |
| 3309 | HSPA5 | NM_005347 |
| 3336 | HSPE1 | NM_002157 |
| 3375 | IAPP | NM_000415 |
| 3440 | IFNA2 | NM_000605 |
| 3456 | IFNB1 | NM_002176 |
| 3480 | IGF1R | NM_000875 |
| 3481 | IGF2 | NM_001007139 NM_000612 |
| 3482 | IGF2R | NM_000876 |
| 3483 | IGFALS | NM_004970 |
| 3485 | IGFBP2 | NM_000597 |
| 3487 | IGFBP4 | NM_001552 |
| 3488 | IGFBP5 | NM_000599 |
| 3489 | IGFBP6 | NM_002178 |
| 3551 | IKBKB | NM_001556 |
| 3552 | IL1A | NM_000575 |
| 3553 | IL1B | NM_000576 |
| 3558 | IL2 | NM_000586 |
| 3559 | IL2RA | NM_000417 |
| 3562 | IL3 | NM_000588 |
| 3563 | IL3RA | NM_002183 |
| 3586 | IL10 | NM_000572 |
| 3588 | IL10RB | NM_000628 |
| 3604 | TNFRSF9 | NM_001561 |
| 3605 | IL17A | NM_002190 |
| 3607 | FOXK2 | NM_004514 XM_001134363 XM_001134364 |
| 3659 | IRF1 | NM_002198 |
| 3725 | JUN | NM_002228 |
| 3726 | JUNB | NM_002229 |
| 3727 | JUND | NM_005354 |
| 3906 | LALBA | NM_002289 |

FIG. 19 (cont'd)

| Entrez Gene ID | Current Symbol | Refseq Transcript |
|---|---|---|
| 3956 | LGALS1 | NM_002305 |
| 3987 | LIMS1 | XM_001129158 NM_004987 |
| 4049 | LTA | NM_000595 |
| 4050 | LTB | NM_009588 NM_002341 |
| 4055 | LTBR | NM_002342 |
| 4064 | CD180 | NM_005582 |
| 4069 | LYZ | NM_000239 |
| 4137 | MAPT | NM_016834 NM_016835 NM_016841 NM_005910 |
| 4170 | MCL1 | NM_021960 NM_182763 |
| 4193 | MDM2 | NM_006881 NM_002392 NM_006879 NM_006878 NM_006882 |
| 4194 | MDM4 | NM_002393 |
| 4214 | MAP3K1 | XM_042066 XM_001128827 |
| 4215 | MAP3K3 | NM_203351 NM_002401 |
| 4217 | MAP3K5 | NM_005923 |
| 4294 | MAP3K10 | NM_002446 |
| 4318 | MMP9 | NM_004994 |
| 4353 | MPO | NM_000250 |
| 4599 | MX1 | NM_002462 |
| 4602 | MYB | NM_005375 |
| 4605 | MYBL2 | NM_002466 |
| 4609 | MYC | XM_001129520 NM_002467 |
| 4616 | GADD45B | NM_015675 |
| 4671 | NAIP | NM_022892 NM_004536 |
| 4790 | NFKB1 | NM_003998 |
| 4791 | NFKB2 | NM_001077494 NM_001077493 NM_002502 |
| 4792 | NFKBIA | NM_020529 |
| 4793 | NFKBIB | NM_001001716 NM_002503 |
| 4794 | NFKBIE | NM_004556 |
| 4803 | NGFB | NM_002506 |
| 4804 | NGFR | NM_002507 |
| 4832 | NME3 | NM_002513 |
| 4842 | NOS1 | NM_000620 |
| 4843 | NOS2A | NM_000625 |
| 4869 | NPM1 | NM_001037738 NM_199185 NM_002520 |
| 4908 | NTF3 | NM_002527 |
| 4914 | NTRK1 | NM_001012331 NM_002529 NM_001007792 |
| 4982 | TNFRSF11B | NM_002546 |
| 5023 | P2RX1 | NM_002558 |
| 5055 | SERPINB2 | NM_002575 |
| 5058 | PAK1 | NM_002576 |
| 5062 | PAK2 | NM_002577 XM_001126110 |
| 5074 | PAWR | NM_002583 |
| 5077 | PAX3 | NM_181457 NM_181460 NM_181459 NM_013942 NM_181461 NM_181458 NM_000438 |
| 5081 | PAX7 | NM_013945 NM_002584 |
| 5133 | PDCD1 | NM_005018 |
| 5134 | PDCD2 | NM_144781 NM_002598 |
| 5153 | PDE1B | NM_000924 |

FIG. 19 (cont'd)

| Entrez Gene ID | Current Symbol | Refseq Transcript |
|---|---|---|
| 5288 | PIK3C2G | NM_004570 |
| 5366 | PMAIP1 | NM_021127 |
| 5371 | PML | NM_033238 NM_033250 NM_033246 NM_033249 NM_033240 NM_033244 NM_033247 NM_002675 NM_033239 |
| 5447 | POR | NM_000941 |
| 5519 | PPP2R1B | NM_002716 NM_181699 |
| 5551 | PRF1 | NM_001083116 NM_005041 |
| 5562 | PRKAA1 | NM_006251 NM_206907 |
| 5578 | PRKCA | NM_002737 |
| 5581 | PRKCE | NM_005400 |
| 5590 | PRKCZ | NM_002744 NM_001033581 NM_001033582 |
| 5594 | MAPK1 | NM_138957 NM_002745 |
| 5596 | MAPK4 | NM_002747 |
| 5598 | MAPK7 | NM_139033 NM_139032 NM_002749 NM_139034 |
| 5599 | MAPK8 | NM_139046 NM_139049 NM_139047 NM_002750 |
| 5602 | MAPK10 | NM_138980 NM_002753 NM_138982 NM_138981 |
| 5604 | MAP2K1 | NM_002755 |
| 5607 | MAP2K5 | NM_002757 NM_145160 |
| 5608 | MAP2K6 | NM_002758 |
| 5610 | EIF2AK2 | NM_002759 |
| 5663 | PSEN1 | NM_000021 |
| 5664 | PSEN2 | NM_012486 NM_000447 |
| 5728 | PTEN | NM_000314 |
| 5733 | PTGER3 | NM_198716 NM_198713 NM_198715 NM_198712 NM_198719 NM_198717 NM_198714 NM_000957 NM_198718 |
| 5741 | PTH | NM_000315 |
| 5743 | PTGS2 | NM_000963 |
| 5747 | PTK2 | NM_153831 NM_005607 |
| 5777 | PTPN6 | NM_002831 NM_080548 |
| 5783 | PTPN13 | NM_080685 NM_006264 NM_080684 NM_080683 |
| 5885 | RAD21 | NM_006265 |
| 5887 | RAD23B | NM_002874 |
| 5894 | RAF1 | NM_002880 |
| 5925 | RB1 | NM_000321 |
| 5926 | ARID4A | NM_023001 NM_002892 NM_023000 |
| 5927 | JARID1A | NM_001042603 NM_005056 |
| 5928 | RBBP4 | NM_005610 |
| 5929 | RBBP5 | NM_005057 |
| 5930 | RBBP6 | NM_032626 NM_018703 NM_006910 |
| 5933 | RBL1 | NM_002895 NM_183404 |
| 5934 | RBL2 | NM_005611 |
| 5970 | RELA | NM_021975 |
| 5971 | RELB | NM_006509 |
| 5977 | DPF2 | NM_006268 |
| 6285 | S100B | NM_006272 |
| 6300 | MAPK12 | NM_002969 |
| 6347 | CCL2 | NM_002982 |

FIG. 19 (cont'd)

| Entrez Gene ID | Current Symbol | Refseq Transcript |
| --- | --- | --- |
| 6416 | MAP2K4 | NM_003010 |
| 6422 | SFRP1 | NM_003012 |
| 6423 | SFRP2 | NM_003013 |
| 6425 | SFRP5 | NM_003015 |
| 6446 | SGK | NM_005627 |
| 6477 | SIAH1 | NM_003031 NM_001006610 |
| 6494 | SIPA1 | NM_006747 NM_153253 |
| 6622 | SNCA | NM_000345 NM_007308 |
| 6647 | SOD1 | NM_000454 |
| 6651 | SON | NM_032195 NM_138927 |
| 6696 | SPP1 | NM_000582 NM_001040060 NM_001040058 |
| 6753 | SSTR3 | NM_001051 |
| 6772 | STAT1 | NM_007315 NM_139266 |
| 6788 | STK3 | NM_006281 |
| 6868 | ADAM17 | NM_003183 |
| 6885 | MAP3K7 | NM_145332 NM_145333 NM_003188 NM_1453 |
| 6997 | TDGF1 | NM_003212 |
| 7009 | TEGT | NM_003217 NM_001098576 |
| 7027 | TFDP1 | NM_007111 |
| 7029 | TFDP2 | NM_006286 |
| 7040 | TGFB1 | NM_000660 |
| 7072 | TIA1 | NM_022037 NM_022173 |
| 7073 | TIAL1 | NM_003252 NM_001033925 |
| 7078 | TIMP3 | NM_000362 |
| 7097 | TLR2 | NM_003264 |
| 7122 | CLDN5 | NM_003277 |
| 7124 | TNF | NM_000594 |
| 7126 | TNFAIP1 | NM_021137 |
| 7127 | TNFAIP2 | NM_006291 |
| 7128 | TNFAIP3 | NM_006290 |
| 7130 | TNFAIP6 | NM_007115 |
| 7132 | TNFRSF1A | NM_001065 |
| 7133 | TNFRSF1B | NM_001066 |
| 7157 | TP53 | NM_000546 |
| 7159 | TP53BP2 | NM_005426 NM_001031685 |
| 7161 | TP73 | NM_005427 |
| 7184 | HSP90B1 | NM_003299 |
| 7185 | TRAF1 | NM_005658 |
| 7186 | TRAF2 | NM_021138 |
| 7187 | TRAF3 | NM_003300 NM_145726 NM_145725 |
| 7188 | TRAF5 | NM_145759 NM_001033910 NM_004619 |
| 7189 | TRAF6 | NM_004620 NM_145803 |
| 7262 | PHLDA2 | NM_003311 |
| 7292 | TNFSF4 | NM_003326 |
| 7293 | TNFRSF4 | NM_003327 |
| 7416 | VDAC1 | NM_003374 |
| 7423 | VEGFB | XM_001128909 NM_003377 |
| 7424 | VEGFC | NM_005429 |

FIG. 19 (cont'd)

| Entrez Gene ID | Current Symbol | Refseq Transcript |
|---|---|---|
| 7529 | YWHAB | NM_139323 NM_003404 |
| 7531 | YWHAE | NM_006761 XM_001126863 |
| 7532 | YWHAG | NM_012479 |
| 7533 | YWHAH | NM_003405 |
| 7534 | YWHAZ | NM_003406 NM_145690 |
| 7818 | DAP3 | NM_033657 NM_004632 |
| 8065 | CUL5 | NM_003478 |
| 8087 | FXR1 | NM_005087 NM_001013439 NM_001013438 |
| 8193 | DPF1 | NM_004647 |
| 8382 | NME5 | NM_003551 |
| 8451 | CUL4A | NM_003589 NM_001008895 |
| 8452 | CUL3 | NM_003590 |
| 8453 | CUL2 | NM_003591 |
| 8454 | CUL1 | NM_003592 |
| 8477 | GPR65 | NM_003608 |
| 8507 | ENC1 | NM_003633 |
| 8517 | IKBKG | NM_003639 |
| 8535 | CBX4 | NM_003655 |
| 8539 | API5 | NM_006595 |
| 8565 | YARS | NM_003680 |
| 8567 | MADD | NM_130476 NM_130475 NM_130470 NM_003682 NM_130473 NM_130474 NM_130471 NM_130472 |
| 8600 | TNFSF11 | NM_003701 NM_033012 |
| 8626 | TP73L | NM_003722 |
| 8678 | BECN1 | NM_003766 |
| 8717 | TRADD | NM_003789 |
| 8718 | TNFRSF25 | NM_148967 NM_003790 NM_001039664 NM_148965 NM_148970 NM_148966 |
| 8727 | CTNNAL1 | NM_003798 |
| 8737 | RIPK1 | NM_003804 |
| 8738 | CRADD | NM_003805 |
| 8739 | HRK | NM_003806 |
| 8740 | TNFSF14 | NM_003807 NM_172014 |
| 8741 | TNFSF13 | NM_172088 NM_003808 NM_172087 |
| 8742 | TNFSF12 | NM_003809 |
| 8743 | TNFSF10 | NM_003810 |
| 8744 | TNFSF9 | NM_003811 |
| 8764 | TNFRSF14 | NM_003820 |
| 8767 | RIPK2 | NM_003821 |
| 8771 | TNFRSF6B | NM_032945 NM_003823 |
| 8772 | FADD | NM_003824 |
| 8784 | TNFRSF18 | NM_004195 NM_148902 NM_148901 |
| 8792 | TNFRSF11A | NM_003839 |
| 8793 | TNFRSF10D | NM_003840 |
| 8794 | TNFRSF10C | NM_003841 |
| 8795 | TNFRSF10B | NM_147187 NM_003842 |
| 8797 | TNFRSF10A | NM_003844 |
| 8835 | SOCS2 | NM_003877 |
| 8837 | CFLAR | NM_003879 |

FIG. 19 (cont'd)

| Entrez Gene ID | Current Symbol | Refseq Transcript |
|---|---|---|
| 8841 | HDAC3 | NM_003883 |
| 8870 | IER3 | NM_003897 |
| 8887 | TAX1BP1 | NM_006024 NM_001079864 |
| 8915 | BCL10 | NM_003921 |
| 8993 | PGLYRP1 | NM_005091 |
| 8995 | TNFSF18 | NM_005092 |
| 8996 | NOL3 | NM_003946 |
| 8997 | KALRN | NM_007064 NM_003947 NM_001024660 |
| 9020 | MAP3K14 | NM_003954 |
| 9021 | SOCS3 | NM_003955 |
| 9093 | DNAJA3 | NM_005147 |
| 9131 | AIFM1 | NM_145813 NM_004208 NM_145812 |
| 9140 | ATG12 | NM_004707 |
| 9141 | PDCD5 | NM_004708 |
| 9166 | EBAG9 | NM_198120 NM_004215 |
| 9191 | DEDD | NM_001039712 NM_001039711 NM_032998 |
| 9214 | FAIM3 | NM_005449 |
| 9220 | TIAF1 | NM_004740 |
| 9262 | STK17B | NM_004226 |
| 9263 | STK17A | NM_004760 |
| 9275 | BCL7B | NM_001707 |
| 9352 | TXNL1 | NM_004786 |
| 9446 | GSTO1 | NM_004832 |
| 9450 | LY86 | NM_004271 |
| 9459 | ARHGEF6 | NM_004840 |
| 9474 | ATG5 | NM_004849 |
| 9516 | LITAF | NM_004862 |
| 9529 | BAG5 | NM_001015048 NM_004873 NM_001015049 |
| 9530 | BAG4 | NM_004874 |
| 9531 | BAG3 | NM_004281 |
| 9532 | BAG2 | NM_004282 |
| 9538 | EI24 | NM_004879 NM_001007277 |
| 9540 | TP53I3 | NM_004881 NM_147184 |
| 9542 | NRG2 | NM_013981 NM_013982 NM_013983 NM_004883 |
| 9577 | BRE | NM_199191 NM_004899 NM_199194 NM_199192 NM_199193 |
| 9616 | RNF7 | NM_183237 NM_014245 |
| 9618 | TRAF4 | NM_004295 |
| 9633 | MTL5 | NM_004923 NM_001039656 |
| 9647 | PPM1F | NM_014634 |
| 9700 | ESPL1 | NM_012291 |
| 9774 | BCLAF1 | NM_001077441 NM_001077440 NM_014739 |
| 9966 | TNFSF15 | NM_005118 |
| 9994 | CASP8AP2 | NM_012115 |
| 10000 | AKT3 | NM_181690 NM_005465 |
| 10010 | TANK | NM_133484 NM_004180 |
| 10016 | PDCD6 | NM_013232 |
| 10017 | BCL2L10 | NM_020396 |

*FIG. 19 (cont'd)*

| Entrez Gene ID | Current Symbol | Refseq Transcript |
|---|---|---|
| 10018 | BCL2L11 | NM_207002 NM_138621 NM_006538 |
| 10116 | FEM1B | NM_015322 |
| 10134 | BCAP31 | NM_005745 |
| 10201 | NME6 | NM_005793 |
| 10224 | ZNF443 | NM_005815 |
| 10285 | SMNDC1 | NM_005871 |
| 10293 | TRAIP | NM_005879 |
| 10296 | MAEA | NM_005882 NM_001017405 |
| 10392 | NOD1 | NM_006092 |
| 10420 | TESK2 | NM_007170 |
| 10497 | UNC13B | NM_006377 |
| 10507 | SEMA4D | NM_006378 |
| 10549 | PRDX4 | NM_006406 |
| 10553 | HTATIP2 | NM_001098520 NM_001098523 NM_001098522 NM_001098521 NM_006410 |
| 10572 | SIVA1 | NM_021709 NM_006427 |
| 10668 | CGRRF1 | NM_006568 |
| 10673 | TNFSF13B | NM_006573 |
| 10753 | CAPN9 | NM_006615 NM_016452 |
| 10787 | NCKAP1 | NM_013436 NM_205842 |
| 10884 | MRPS30 | NM_016640 |
| 10885 | WDR3 | NM_006784 |
| 10892 | MALT1 | NM_006785 NM_173844 |
| 10912 | GADD45G | NM_006705 |
| 10913 | EDAR | NM_022336 |
| 10922 | FASTK | NM_033015 NM_006712 |
| 10971 | YWHAQ | NM_006826 |
| 11009 | IL24 | NM_006850 NM_181339 |
| 11035 | RIPK3 | NM_006871 |
| 11124 | FAF1 | NM_007051 |
| 11131 | CAPN11 | NM_007058 |
| 11235 | PDCD10 | NM_007217 NM_145860 NM_145859 |
| 22861 | NLRP1 | NM_014922 NM_033006 NM_001033053 NM_033007 NM_033004 |
| 22900 | CARD8 | NM_014959 |
| 22984 | PDCD11 | NM_014976 |
| 23017 | FAIM2 | NM_012306 |
| 23064 | SETX | NM_015046 |
| 23087 | TRIM35 | NM_171982 |
| 23531 | MMD | NM_012329 |
| 23542 | MAPK8IP2 | NM_016431 NM_012324 |
| 23567 | ZNF346 | NM_012279 |
| 23581 | CASP14 | NM_012114 |
| 23591 | 39174 | XR_017911 XR_017759 |
| 23604 | DAPK2 | NM_014326 |
| 23636 | NUP62 | NM_016553 NM_153719 NM_012346 NM_153718 |
| 23645 | PPP1R15A | NM_014330 |
| 23647 | ARFIP2 | NM_012402 |
| 23786 | BCL2L13 | NM_015367 |

*FIG. 19 (cont'd)*

| Entrez Gene ID | Current Symbol | Refseq Transcript |
|---|---|---|
| 23787 | MTCH1 | NM_014341 |
| 25816 | TNFAIP8 | NM_001077654 NM_014350 |
| 25824 | PRDX5 | NM_181651 NM_012094 NM_181652 |
| 26471 | NUPR1 | NM_012385 NM_001042483 |
| 26574 | AATF | NM_012138 |
| 27018 | NGFRAP1 | NM_014380 NM_206917 NM_206915 |
| 27141 | CIDEB | NM_014430 |
| 27242 | TNFRSF21 | NM_014452 |
| 27250 | PDCD4 | NM_145341 NM_014456 |
| 27429 | HTRA2 | NM_013247 NM_145074 |
| 28986 | MAGEH1 | NM_014061 |
| 29108 | PYCARD | NM_145182 NM_013258 |
| 29775 | CARD10 | NM_014550 |
| 51079 | NDUFA13 | NM_015965 |
| 51129 | ANGPTL4 | NM_139314 NM_001039667 |
| 51275 | C12orf47 | XR_017874 XR_017973 |
| 51283 | BFAR | NM_016561 |
| 51330 | TNFRSF12A | NM_016639 |
| 51374 | C2orf28 | NM_080592 NM_016085 |
| 51428 | DDX41 | NM_016222 |
| 51454 | GULP1 | NM_016315 |
| 51567 | TTRAP | NM_016614 |
| 51651 | PTRH2 | NM_016077 |
| 51747 | CROP | NM_006107 NM_016424 |
| 51750 | RTEL1 | NM_016434 NM_032957 |
| 54205 | CYCS | NM_018947 |
| 54466 | SPIN2A | NM_019003 |
| 54476 | TRIAD3 | NM_207111 NM_207116 |
| 54764 | ZRANB1 | NM_017580 |
| 54840 | APTX | NM_175073 NM_175069 NM_175071 NM_175072 NM_017692 |
| 55504 | TNFRSF19 | NM_018647 NM_148957 |
| 55655 | NLRP2 | NM_017852 |
| 55973 | BCAP29 | NM_001008406 NM_018844 NM_001008407 NM_001008405 |
| 56616 | DIABLO | NM_138930 NM_138929 NM_019887 |
| 56848 | SPHK2 | NM_020126 |
| 56940 | DUSP22 | NM_020185 XM_001132925 |
| 57099 | AVEN | NM_020371 |
| 57142 | RTN4 | NM_007008 NM_153828 NM_020532 NM_207521 NM_207520 |
| 57448 | BIRC6 | NM_016252 |
| 57761 | TRIB3 | NM_021158 |
| 58484 | NLRC4 | NM_021209 |
| 59082 | ICEBERG | NM_021571 |
| 59347 | FKSG2 | NM_021631 |
| 63924 | CIDEC | NM_022094 |
| 63970 | P53AIP1 | NM_022112 |
| 64065 | PERP | NM_022121 |
| 64127 | NOD2 | NM_022162 |

FIG. 19 (cont'd)

| Entrez Gene ID | Current Symbol | Refseq Transcript |
|---|---|---|
| 64170 | CARD9 | NM_052813 |
| 64651 | AXUD1 | NM_033027 |
| 64919 | BCL11B | NM_022898 NM_138576 |
| 79092 | CARD14 | NM_024110 NM_052819 |
| 79370 | BCL2L14 | NM_138722 NM_138724 NM_030766 NM_138723 |
| 79444 | BIRC7 | NM_022161 NM_139317 |
| 79960 | PHF17 | NM_199320 NM_024900 |
| 83596 | BCL2L12 | NM_138639 NM_001040668 |
| 84306 | PDCD2L | NM_032346 |
| 84433 | CARD11 | NM_032415 |
| 84674 | CARD6 | NM_032587 |
| 91662 | NLRP12 | NM_033297 NM_144687 |
| 112401 | BIRC8 | NM_033341 |
| 114548 | NLRP3 | NM_183395 NM_001079821 NM_004895 |
| 114770 | PGLYRP2 | NM_052890 |
| 283849 | EXOC3L | NM_178516 |
| 399687 | MYO18A | NM_203318 NM_078471 |
| 440081 | DDX12 | XM_495908 XM_931833 |
| 728642 | CDC2L2 | NM_033529 NM_024011 |
| 613 | BCR | NM_004327 |
| 3716 | JAK1 | NM_001320923 |
| 3717 | JAK2 | NM_001322194 |
| 7422 | VEGF | NM_001025366 |
| 1956 | EGFR | NM_001346897 |
| 238 | ALK | NM_001353765 |
| 983 | CDK1 | NM_001320918 |
| 672 | BRCA | NM_007294 |
| 5290 | PIK3CA | NM_006218 |
| 5609 | MEK | NM_145185 |
| 3815 | KIT | NM_000222 |
| 4893 | NRAS | NM_002524 |

*FIG. 19 (cont'd)*

| Entrez Gene ID | Current Symbol | Refseq Transcript |
|---|---|---|
| 324 | APC | NM_000038 |
| 472 | ATM | NM_000051 NM_138292 |
| 545 | ATR | XM_001131387 NM_001184 |
| 580 | BARD1 | NM_000465 |
| 672 | BRCA1 | NM_007300 NM_007297 NM_007304 NM_007294 NM_007296 NM_007299 NM_007303 NM_007302 NM_007295 NM_007298 NM_007305 |
| 675 | BRCA2 | NM_000059 |
| 754 | PTTG1IP | NM_004339 |
| 857 | CAV1 | NM_001753 |
| 858 | CAV2 | NM_001233 NM_198212 |
| 999 | CDH1 | NM_004360 |
| 1026 | CDKN1A | NM_078467 NM_000389 |
| 1027 | CDKN1B | NM_004064 |
| 1028 | CDKN1C | NM_000076 |
| 1029 | CDKN2A | NM_000077 NM_058195 NM_058197 |
| 1030 | CDKN2B | NM_004936 NM_078487 |
| 1031 | CDKN2C | NM_001262 NM_078626 |
| 1033 | CDKN3 | NM_005192 |
| 1540 | CYLD | NM_001042355 NM_001042412 NM_015247 |
| 1612 | DAPK1 | NM_004938 |
| 1647 | GADD45A | NM_001924 |
| 1869 | E2F1 | NM_005225 |
| 2195 | FAT | NM_005245 |
| 2196 | FAT2 | NM_001447 |
| 2873 | GPS1 | NM_212492 NM_004127 |
| 2874 | GPS2 | NM_004489 |
| 3090 | HIC1 | NM_001098202 NM_006497 |
| 3091 | HIF1A | NM_001530 NM_181054 |
| 3814 | KISS1 | NM_002256 |
| 4616 | GADD45B | NM_015675 |
| 4763 | NF1 | NM_000267 NM_001042492 |
| 4771 | NF2 | NM_181825 NM_016418 NM_181833 NM_181828 NM_181829 NM_000268 NM_181830 NM_181831 NM_181832 |
| 4820 | NKTR | NM_005385 |
| 4978 | OPCML | NM_001012393 NM_002545 |
| 5157 | PDGFRL | NM_006207 |
| 5728 | PTEN | NM_000314 |
| 5925 | RB1 | NM_000321 |
| 5931 | RBBP7 | NM_002893 |
| 5933 | RBL1 | NM_002895 NM_183404 |
| 5934 | RBL2 | NM_005611 |
| 6251 | RSU1 | NM_152724 NM_012425 |
| 6400 | SEL1L | NM_005065 |
| 6648 | SOD2 | NM_000636 NM_001024465 NM_001024466 |
| 6868 | ADAM17 | NM_003183 |
| 324 | APC | NM_000038 |

FIG. 20

| Entrez Gene ID | Current Symbol | Refseq Transcript |
|---|---|---|
| 7157 | TP53 | NM_000546 |
| 7158 | TP53BP1 | NM_005657 |
| 7159 | TP53BP2 | NM_005426 NM_001031685 |
| 7161 | TP73 | NM_005427 |
| 7184 | HSP90B1 | NM_003299 |
| 7251 | TSG101 | NM_006292 |
| 7260 | TSSC1 | NM_003310 |
| 7411 | VBP1 | NM_003372 |
| 7428 | VHL | NM_198156 NM_000551 |
| 7490 | WT1 | NM_024425 NM_024426 NM_024424 NM_000378 |
| 7991 | TUSC3 | NM_178234 NM_006765 |
| 8555 | CDC14B | NM_001077181 NM_003671 NM_033331 |
| 8556 | CDC14A | NM_033312 NM_003672 NM_033313 |
| 8626 | TP73L | NM_003722 |
| 8844 | KSR1 | NM_014238 |
| 9113 | LATS1 | NM_004690 |
| 9232 | PTTG1 | NM_004219 |
| 9537 | TP53I11 | NM_001076787 NM_006034 |
| 9540 | TP53I3 | NM_004881 NM_147184 |
| 9589 | WTAP | NM_004906 NM_152857 NM_152858 |
| 9821 | RB1CC1 | NM_014781 NM_001083617 |
| 10078 | TSSC4 | NM_005706 |
| 10168 | ZNF197 | NM_001024855 NM_006991 |
| 10256 | CNKSR1 | NM_006314 |
| 10263 | CDK2AP2 | NM_005851 |
| 10641 | TUSC4 | NM_006545 |
| 10744 | PTTG2 | NM_006607 |
| 10912 | GADD45G | NM_006705 |
| 11068 | CYB561D2 | NM_007022 |
| 11144 | DMC1 | NM_007068 |
| 11145 | HRASLS3 | NM_007069 |
| 11178 | LZTS1 | NM_021020 |
| 11186 | RASSF1 | NM_170714 NM_170712 NM_007182 NM_170713 |
| 11319 | ECD | NM_007265 |
| 11334 | TUSC2 | NM_007275 |
| 22908 | SACM1L | NM_014016 |
| 25855 | BRMS1 | NM_001024957 NM_015399 |
| 25900 | HOM-TES-103 | NM_001039670 NM_080730 NM_080731 |
| 26255 | PTTG3 | NR_002734 |
| 26524 | LATS2 | NM_014572 |
| 27156 | RTDR1 | NM_014433 |
| 28316 | CDH20 | NM_031891 |
| 28513 | CDH19 | NM_021153 |
| 29997 | GLTSCR2 | NM_015710 |

*FIG. 20 (Cont'd)*

| Entrez Gene ID | Current Symbol | Refseq Transcript |
|---|---|---|
| 29998 | GLTSCR1 | NM_015711 |
| 51213 | LUZP4 | NM_016383 |
| 51352 | WIT1 | NM_015855 |
| 51684 | SUFU | NM_016169 |
| 51752 | ARTS-1 | NM_016442 NM_001040458 |
| 54979 | HRASLS2 | NM_017878 |
| 57110 | HRASLS | NM_020386 |
| 57509 | MTUS1 | NM_001001931 NM_001001925 NM_020749 NM_001001924 |
| 57786 | RBAK | NM_021163 |
| 64061 | TSPYL2 | XM_001128695 NM_022117 |
| 79577 | CDC73 | NM_024529 |
| 79689 | STEAP4 | NM_024636 |
| 83937 | RASSF4 | NM_032023 |
| 84312 | BRMS1L | NM_032352 |
| 84445 | LZTS2 | NM_032429 |
| 84955 | NUDCD1 | NM_032869 |
| 94241 | TP53INP1 | NM_033285 |
| 120114 | FAT3 | NM_001008781 XM_926199 XM_936538 |
| 124641 | OVCA2 | NM_080822 |
| 129025 | SUHW1 | NM_080740 |
| 140883 | SUHW2 | NM_080764 |
| 283455 | KSR2 | NM_173598 |
| 286827 | TRIM59 | NM_173084 |
| 338440 | TMEM16J | XM_001129032 NM_001012302 |

FIG. 20 (Cont'd)

MULTIMODAL CANCER THERAPY COMPRISING CHIMERIC VIRAL/NONVIRAL NANOPARTICLES AND ANTICANCER AGENTS

CROSS REFERENCE TO RELATED APPLICATIONS

This application claims priority under 35 U.S.C. § 119 from Provisional Application Ser. No. 62/712,956 filed Jul. 31, 2018, the disclosure of which is incorporated herein by reference.

STATEMENT OF GOVERNMENT SUPPORT

This invention was made with government support under Grant No. 1R21CA228099-01A1 awarded by the National Cancer Institute, and Grant No. 5T32AI7319-28 awarded by the National Institutes of Health. The government has certain rights in the invention.

TECHNICAL FIELD

The disclosure provides for a multimodal cancer therapy comprising chimeric viral/nonviral nanoparticles and anticancer agents and uses thereof to treat a subject with cancer or suspected of having a cancer.

BACKGROUND

Development of efficient and safe delivery methods remains a pivotal challenge in gene therapy. Recombinant viral vectors are superior to nonviral vectors in delivering genes, especially in vivo. However, viral vectors also offer considerable limitations, such as immune responses (particularly upon repeated administrations), difficulties in large-scale production, limited size of genes that can be packaged, narrow cell tropisms, and lack of surface modalities for molecular (synthetic) modifications without altering viral stability and infectivity. Immunosuppression is often required prior to viral gene delivery but increases the chance of opportunistic infection. Genetically modifying the viral capsid and envelope, conjugating various functional moieties (e.g., targeting molecules), and electrostatically or covalently incorporating lipids or polymers are often accompanied by compromised infectivity or retained/new immunogenicity upon repeated administrations. Nonviral vectors using synthetic materials (e.g., cationic lipids and polymers), on the other hand, are easy to manufacture on a large scale, can deliver larger payloads, and further are readily tunable for desirable structure/performance, and exhibit low immunogenicity. However, poor transfection, particularly in vivo, has been a fundamental challenge in employing nonviral vectors for gene therapy.

SUMMARY

Single modal cancer therapy that targets one pathological pathway often turns out to be inefficient. For example, tyrosine kinase inhibitors (TKI), like imatinib, interfere with cancer progression but are not known to be effective in eliminating cancer cells, thus, the development of drug-resistance in some cancer cell populations to TKIs is of clinical concern. Presented herein is a multimodal cancer therapy that avoids the foregoing drawbacks by co-administering an anticancer agent (e.g., TKI) with a chimeric nanoparticle that simultaneously tackles multiple pathways linked to the particular type of cancer. These viral/nonviral chimeric nanoparticles (ChNPs) comprise an adeno-associated virus (AAV) core and an acid-degradable polymeric shell comprising incorporated gene silencing/editing nucleic acids. The ChNPs of the disclosure have been designed to simultaneously induce pro-apoptotic gene expression (e.g., BIM) by the AAV core and silencing tumor promoting factors (e.g., MCL-1) with inhibitory RNAs (e.g., siRNA) encapsulated in the acid-degradable polymeric shell.

In studies presented herein BIM/MCL-1 ChNPs were able to efficiently suppress the proliferation of BCR-ABL+ K562, BaF3 p210 and FL5.12/p190 cells in vitro and in vivo via simultaneously expressing BIM and silencing MCL-1. It was further found herein that BIM/MCL-1 ChNPs significantly reduced $IC_{50}$ values of dasatinib, a tyrosine kinase inhibitor (TKI) against BCR-ABL, in a concentration dependent manner. For example, BIM/MCL-1 ChNPs at a concentration of $1\times10^{10}$ GC AAV/0.5 µg MCL-1 siRNA per mL decreased $IC_{50}$ of dasatinib about 22 times, compared with an $IC_{50}$ of 1 nM without ChNPs. When BCR-ABL⁻ FL5.12 cells were treated under the same conditions, about 100% cell viability was observed even at the highest concentrations of both BIM/MCL-1 ChNPs and dasatinib. In in vivo studies, mice with leukemia had significantly higher survival rates when treated with a combined therapy of BIM/MCL-1 ChNPs and dasatinib than treated with dasatanib alone. Accordingly, the foregoing results indicate that: (1) simultaneous BIM expression and MCL-1 silencing by BIM/MCL-1 ChNPs and (2) synergistic eradication of BCR-ABL⁺ cells when co-administered with BIM/MCL-1 ChNPs and chemotherapeutics. In additional studies presented herein, it was found that the ChNPs of the disclosure had broad applicability in treating various forms of cancer by acting synergistically with various anticancer agents (e.g., dasatinib, erlotinib, lapatinib, ruxolitinib, PLX-4720 and PD98059) to suppress growth and proliferation in various cancer models (e.g., Ph+ leukemias, EGFR+ non-small cell lung cancers, Her2+ Breast cancers, triple negative breast cancers, Braf+ melanomas, Kit+ melanomas, and Nras+ melanomas).

In a particular embodiment, the disclosure provides for a multimodal cancer therapy for treating a subject having a cancer, comprising: co-administering to the subject in need thereof a therapeutically effective amount of one or more anticancer agents and one or more chimeric viral/nonviral nanoparticles (ChNPs), wherein the ChNPs comprise: (i) a core comprising a recombinant adeno-associated virus (AAV) that expresses a transgene which encodes a pro-apoptosis gene product and/or tumor suppresser gene product; and (ii) one or more acid labile degradable polymer layers surrounding the core, wherein the acid labile degradable polymer layers comprise encapsulated gene silencing/editing nucleic acids that suppress or inhibit the expression of gene products from oncogenes and/or suppress the expression of gene products associated with a cancer, wherein the acid degradable polymer layers hydrolyze in a mildly acidic environment having a pH from 4.5 to 6.8. In a further embodiment, the cancer is selected from the group consisting of: adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In yet a further embodiment, the cancer is selected from the group consisting of a chronic myelogenous leukemia (CML), acute lymphoblastic leukemia (ALL), non-small cell lung cancer (NSCLC), breast cancer, melanoma, colorectal cancer, and ovarian cancer. In another embodiment, the recombinant AAV is AVV serotype 1, AVV serotype 2, AVV serotype 3, AVV serotype 5, AVV serotype 7, AVV serotype 8 or AVV serotype 9. In a particular embodiment, the AAV is AVV serotype 2. In yet a further embodiment, the one or more acid labile degradable polymer layers are polyketal-based polymer layers. In another embodiment, the polyketal-based polymer layers are made from photo-polymerization of acid-cleavable amino ketal monomers having the structure of:

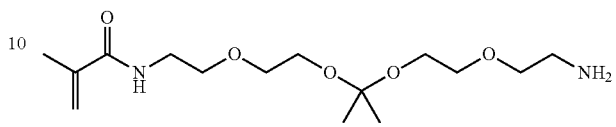

and acid-cleavable cross-linkers having the structure of:

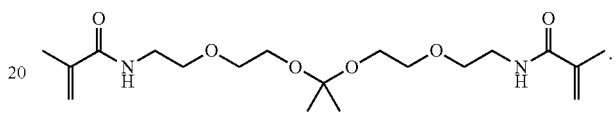

In yet another embodiment, wherein eosin is used as a photoinitiator for the photo-polymerization of the acid-cleavable amino ketal monomers and acid-cleavable cross-linkers. In a certain embodiment, the ChNPs have a diameter of 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 350 nm, 400 nm, 450 nm, 500 nm, 550 nm, 600 nm, 650 nm, 700 nm, or a range that includes or is between any two of the foregoing values, including fractional increments thereof. In a further embodiment, the ChNPs have a diameter from 100 nm to 500 nm. In another embodiment, the transgene is multicistronic and encodes either two or more pro-apoptosis genes, two or more tumor suppressor genes, or at least one pro-apoptosis gene and at least one tumor suppressor gene. In yet another embodiment, the transgene comprises a pro-apoptosis gene selected from the group consisting of MTCH1, TNFAIP8, PRDX5, NUPR1, AATF, NGFRAP1, CIDEB, TNFRSF21, PDCD4, HTRA2, MAGEH1, PYCARD, CARD10, BCL2L11, FEM1B, BCAP31, NME6, ZNF443, SMNDC1, TRAIP, MAEA, NOD1, TESK2, UNC13B, SEMA4D, PRDX4, HDAC3, IER3, TAX1BP1, BCL10, PGLYRP1, TNFSF18, NOL3, KALRN, MAP3K14, SOCS3, DNAJA3, AIFM1, ATG12, YWHAB, YWHAE, YWHAG, YWHAH, YWHAZ, DAP3, CUL5, FXR1, DPF1, NME5, CUL4A, CUL3, CUL2, MAP2K4, SFRP1, SFRP2, SFRP5, SGK, SIAH1, SIPA1, SNCA, SOD1, SON, SPP1, SSTR3, STAT1, STK3, PIK3C2G, PMAIP1, PML, POR, PPP2R1B, PRF1, PRKAA1, PRKCA, PRKCE, PRKCZ, MAPK1, LGALS1, LIMS1, LTA, LTB, LTBR, CD180, LYZ, MAPT, MCL1, MDM2, MDM4, MAP3K1, MAP3K3, GAS2, GDNF, GML, GPX1, GPX4, GRB2, GSK3B, GSN, GSR, GSTM1, GSTP1, GSTT2, GZMH, GZMA, CHUK, CIDEA, CLU, CLN3, CNR1, CNR2, CNTF, MAPK14, CSE1L, CTNNB1, CTSD, CYC1, DAD1, DAP, BOK, BRCA1, BRAF, BTK, C5, C6, C7, C8A, C8B, CBG, ABL1, ADORA1, ADORA2A, PARP1, PARP4, ADRA1A, AGTR2, AHR, AIF1, AKT1, AKT2, ALOX12, APAF1, NUDT2, APEX1, BIRC2, BIRC3, BIRC4, BIRC5, APLP1, APP, FAS, FASLG, RHOA, RHOB, ATM, BAD, BAG1, BAK1, BARD1, BAX, BCL2, BCL2A1, BCL2L1, BCL2L2, BCL3, BCL6, TNFRSF17, BDNF, BID, BIK, BMP4, BNIP1, BNIP2, BNIP3, C9, CAPN1, CAPN6, CASP1, CASP2, CASP3, CASP4, CASP5, CASP6, CASP7, CASP8, CASP9, CASP10, CAV1, CAV2, CBL, CD2, CDSL, CD14, CD27, CD28, TNFRSF8, TNFSF8, SCARB1, CD38, CD40, CD40LG, CD70, CDC2L1, CDC25A, CDKN1A, CDKN2A, CDKN2D, CGB, DAPK1, DAPK3, DAXX, DCC, GADD45A, DDIT3, DFFA, DFFB, DNASE1, DNASE1L3, DNASE2, DOCK1, DUSP6, DUSP7, E2F1, E2F3, E2F5, EIF4G2, EMP1, EMP2, EMP3, EP300, ERCC2, ERCC3, ERN1, F2, F2R, FANCA, PTK2B, FIGF, FOXO1, FOXO3, FOSL2, GAB1, GZMB, GZMM, HD, HDAC1, HSPA5, HSPE1, IAPP, IFNA2, IFNB1, IGF1R, IGF2, IGF2R, IGFALS, IGFBP2, IGFBP4, IGFBP5, IGFBP6, IKBKB, IL1A, IL1B, IL2, IL2RA, IL3, IL3RA, IL10, IL10RB, TNFRSF9, IL17A, FOXK2, IRF1, JUN, JUNB, JUND, LALBA, MAP3K5, MAP3K10, MMP9, MPO, MX1, MYB, MYBL2, MYC, GADD45B, NAIP, NFKB1, NFKB2, NFKBIA, NFKBIB, NFKBIE, NGFB, NGFR, NME3, NOS1, NOS2A, NPM1, NTF3, NTRK1, TNFRSF11B, P2RX1, SERPINB2, PAK1, PAK2, PAWR, PAX3, PAX7, PDCD1, PDCD2, PDE1B, MAPK4, MAPK7, MAPK8, MAPK10, MAP2K1, MAP2K5, MAP2K6, EIF2AK2, PSEN1, PSEN2, PTEN, PTGER3, PTH, PTGS2, PTK2, PTPN6, PTPN13, RAD21, RAD23B, RAF1, RB1, ARID4A, JARID1A, RBBP4, RBBP5, RBBP6, RBL1, RBL2, RELA, RELB, DPF2, S100B, MAPK12, CCL2, ADAM17, MAP3K7, TDGF1, TEGT, TFDP1, TFDP2, TGFB1, TIA1, TIAL1, TIMP3, TLR2, CLDN5, TNF, TNFAIP1, TNFAIP2, TNFAIP3, TNFAIP6, TNFRSF1A, TNFRSF1B, TP53, TP53BP2, TP73, HSP90B1, TRAF1, TRAF2, TRAF3, TRAF5, TRAF6, PHLDA2, TNFSF4, TNFRSF4, VDAC1, VEGFB, VEGFC, CUL1, GPR65, ENC1, IKBKG, CBX4, API5, YARS, MADD, TNFSF11, TP73L, BECN1, TRADD, TNFRSF25, CTNNAL1, RIPK1, CRADD, HRK, TNFSF14, TNFSF13, TNFSF12, TNFSF10, TNFSF9, TNFRSF14, RIPK2, TNFRSF6B, FADD, TNFRSF18, TNFRSF11A, TNFRSF10D, TNFRSF10C, TNFRSF10B, TNFRSF10A, SOCS2, CFLAR, PDCD5, EBAG9, DEDD, FAIM3, TIAF1, STK17B, STK17A, BCL7B, TXNL1, GSTO1, LY86, ARHGEF6, ATG5, LITAF, BAG5, BAG4, BAG3, BAG2, EI24, TP53I3, NRG2, BRE, RNF7, TRAF4, MTL5, PPM1F, ESPL1, BCLAF1, TNFSF15, CASP8AP2, AKT3, TANK, PDCD6, BCL2L10, HTATIP2, SIVA1, CGRRF1, TNFSF13B, CAPN9, NCKAP1, MRPS30, WDR3, MALT1, GADD45G, EDAR, FASTK, YWHAQ, IL24, RIPK3, FAF1, CAPN11, PDCD10, NLRP1, CARD8, PDCD11, FAIM2, SETX, TRIM35, MMD, MAPK8IP2, ZNF346, CASP14, 39174, DAPK2, NUP62, PPP1R15A, ARFIP2, BCL2L13, NDUFA13, ANGPTL4, C12orf47, BFAR, TNFRSF12A, C2orf28, DDX41, GULP1, TTRAP, PTRH2, CROP, RTEL1, CYCS, SPIN2A, TRIAD3, ZRANB1, APTX, TNFRSF19, NLRP2, BCAP29, DIABLO, SPHK2, DUSP22, AVEN, RTN4, BIRC6, TRIB3, NLRC4, ICE-BERG, FKSG2, CIDEC, P53AIP1, PERP, NOD2, CARD9, AXUD1, BCL11B, CARD14, BCL2L14, BIRC7, PHF17, BCL2L12, PDCD2L, CARD11, CARD6, NLRP12, BIRC8, NLRP3, PGLYRP2, EXOC3L, MYO18A, DDX12, and CDC2L2. In a particular embodiment, the transgene comprises BCL2L11 (BIM). In another embodiment, the transgene comprises a tumor suppressor gene selected from the group consisting of APC, ATM, ATR, BARD1, BRCA1, BRCA2, PTTG1IP, CAV1, CAV2, CDH1, CDKN1A, CDKN1B, CDKN1C, CDKN2A, CDKN2B, CDKN2C, CDKN3, CYLD, DAPK1, GADD45A, E2F1, FAT, FAT2, GPS1, GPS2, HIC1, HIF1A, KISS1, GADD45B, NF1, NF2, NKTR, OPCML, PDGFRL, PTEN, RB1, RBBP7, RBL1, RBL2, RSU1, SEL1L, SOD2, ADAM17, APC, TP53, TP53BP1, TP53BP2, TP73, HSP90B1, TSG101, TSSC1, VBP1, VHL, WT1, TUSC3, CDC14B, CDC14A, TP73L, KSR1, LATS1, PTTG1, TP53I11, TP53I3, WTAP, RB1CC1, TSSC4, ZNF197, CNKSR1, CDK2AP2, TUSC4, PTTG2, GADD45G, CYB561D2, DMC1, HRASLS3, LZTS1, RASSF1, ECD, TUSC2, SACM1L, BRMS1, HOM-TES-103, PTTG3, LATS2, RTDR1, CDH20, CDH19, GLTSCR2, GLTSCR1, LUZP4, WIT1, SUFU, ARTS-1, HRASLS2, HRASLS, MTUS1, RBAK, TSPYL2, CDC73, STEAP4, RASSF4, BRMS1L, LZTS2, NUDCD1, TP53INP1, FAT3, OVCA2, SUHW1, SUHW2, KSR2, TRIM59, and TMEM16J. In another embodiment, the gene silencing/editing nucleic acids are siRNA, shRNA or miRNA. In yet another embodiment, the gene silencing/editing nucleic acids suppress the expression of a gene product from a gene selected from the group consisting of BCR, BRAF, JAK1, JAK2, VEGF, EGFR, ALK, CDK1, CDK2, CDK3, CDK3, CDK4, BRCA, PIK3CA, MEK, C-KIT, NRAS, MCL-1, ABCB11, ANTXR2, BCOR, CDKN1B, CYP27A1, EMD, FANCF, ABCC8, APC, BCORL1, CDKN2A, CYP27B1, EP300, FANCG, ABCC9, AR, BLM, CEP290, DAXX, EPCAM, FANCI, ABCD1, ARID1A, BMPR1A, CFTR, DBT, EPHA5, FANCL, ABL1, ARID2, BRAF, CHEK1, DCC, EPHB2, FANCM, ACADM, ARSA, BRCA1, CHEK2, DCX, ERBB2, FAS, CADS, ASAH1, BRCA2, CHM, DDB2, ERBB3, FAT3, ACADVL, ASCC1, BRIP1, CIC, DDR2, ERBB4, FBXO11, ACTC1, ASL, BTD, CLN3, DES, ERCC2, FBXO32, ACTN2, ASPA, BTK, CLN5, DHCR7, ERCC3, FBXW7, ACVR1B, ASS1, BUB1B, CLN6, DICER1, ERCC4, FGD4, ADA, ASXL1, CALR3, CLN8, DIS3L2, ERCC5, FGFR1, ADAMTS13, ATM, CARD11, COL1A2, DKC1, ERCC6, FGFR2, ADAMTS2, ATP4A, CASP8, COL4A3, DLD, ERRFI1, FGFR3, AGA, ATP6V0D2, CAV3, COL4A4, DMD, ESCO2, FH, AGL, ATP7A, CBFB, COL7A1, DNAJB2, ESR1, FKTN, AGPS, ATP7B, CBL, COX15, DNMT3A, ETV6, FLCN, AHI1, ATP8B1, CBLB, CREBBP, DSC2, EXOC2, FLT3, AIP, ATR, CBLC, CRLF2, DSE, EXT1, FMR1, AKAP9, ATRX, CBS, CRTAP, DSC2, EXT2, FUBP1, AKT1, AXIN1, CCDC178, CRYAB, DSP, EYA4, FZD3, AKT2, AXIN2, CCNE1, CSF1R, DTNA, EZH2, G6PC, ALB, BAG3, CD79A, CSMD3, ECT2L, F11, GAA, ALDH3A2, BAI3, CD79B, CSRP3, EDA, F5, GABRA6, ALDOB, BAP1, CD96, CTNNB1, EDN3, FAH, GALNT12, ALK, BARD1, CDC27, CTNS, EDNRB, FAM46C, GALT, ALS2, BAX, CDC73, CTSK, EED, FANCA, GATA1, AMER1, BAZ2B, CDH1, CUBN, EGFR, FANCB, GATA2, AMPD1, BCKDHA, CDH23, CYLD, EGR2, FANCC, GATA3, AMPH, BCKDHB, CDK12, CYP11A1, EHBP1, FANCD2, GATAD1, ANTXR1, BCL6, CDK4, CYP21A2, ELMO1, FANCE, GBA, GCDH, JAK1, MDM2, NEK2, PLOD1, ROS1, SMPD1, GJB2, JAK2, MECP2, NEXN, PLP1, RPGRIP1L, SOX10, GLA, JAK3, MED12, NF1, PMP22, RS1, SOX2, GLB1, JUP, MEFV, NF2, PMS2, RSPO1, SPEG, GLI1, KAT6A, MEN1, NFE2L2, POLD1, RTEL1, SPOP, GLI3, KCNQ1, MET, NFKBIA, POLE, RUNX1, SRC, GLMN, KDM4B, MFSD8, NIPA2, POLH, RUNX1T1, SSTR1, GNA11, KDM6A, MIER3, NKX3-1, POMGNT1, RYR2, STAG2, GNAQ, KDR, MITF, NOTCH1, POMT1, S1PR2, STAR, GNAS, KEAP1, MKS1, NOTCH2, POU1F1, SAMD9L, STK11, GNPTAB, KIF1B, MLH1, NPC1, POU6F2, SBDS, SUFU, GPC3, KIT, MLH3, NPC2, PPM1L, SCN11A, SUZ12, GPC6, KLF6, MMAB, NPHP1, PPP2R1A, SCN5A, SYNE3, GPR78, KLHDC8B, MPL, NPHP4, PPT1, SCNN1A, TAZ, GRIN2A, KMT2A, MPZ, NPM1, PRDM1, SCNN1B, TBX20, GRM8, KMT2C, MRE11A, NRAS, PRKAG2, SCNN1G, TCAP, GXYLT1, KMT2D, MSH2, NRCAM, PRKAR1A, SCO2, TCERG1, H3F3A, KRAS, MSH3, NTRK1, PRKDC, SDHA, TCF7L2, HADHA, KREMEN1, MSH6, NUP62, PROC, SDHAF2, TERT, HADHB, L1CAM, MSMB, OR5L1, PROP1, SDHB, TET2, HBB, LAMA2, MSR1, OTC, PRPF40B, SDHC, TFG, HESX1, LAMA4, MTAP, OTOP1, PRX, SDHD, TGFB3, HEXA, LAMP2, MTHFR, PAH, PSAP, SEPT9, TGFBR1, HEXB, LDB3, MTM1, PALB2, PSEN1, SETBP1, TGFBR2, HFE, LEPRE1, MTOR, PALLD, PSEN2, SETD2, THSD7B, HGSNAT, LIG4, MUC16, PAX5, PTCH1, SF1, TINF2, HIST1H3B, LMNA, MUT, PAX6, PTCH2, SF3A1, TMC6, HNF1A, LPAR2, MUTYH, PBRM1, PTEN, SF3B1, TMC8, HRAS, LRP1B, MYBPC3, PCDH15, PTGFR, SGCD, TMEM127, HSPH1, LRPPRC, MYC, PCGF2, PTPN11, SGSH, TMEM43, IDH1, LRRK2, MYD88, PDE11A, PTPN12, SH2B3, TMEM67, IDH2, LYST, MYH6, PDGFRA, RAC1, SLC25A4, TMPO, IGF2R, MAP2K1, MYH7, PDHA1, RAD21, SLC26A2, TNFAIP3, IGHMBP2, MAP2K2, MYL2, PDZRN3, RAD50, SLC37A4, TNFRSF14, IGSF10, MAP2K4, MYL3, PEX1, RAD51B, SLC7A8, TNNC1, IKBKAP, MAP3K1, MYLK2, PEX7, RAD51C, SLC9A9, TNNI3, IKZF1, MAP4K3, MYO1B, PHF6, RAD51D, SLX4, TNNT1, IKZF4, MAP7, MYO7A, PIK3CA, RARB, SMAD2, TNNT2, IL2RG, MAPK10, MYOZ2, PIK3CG, RB1, SMAD4, TP53, IL6ST, MAS1L, MYPN, PIK3R1, RBM20, SMARCA4, TPM1, IL7R, MAX, NBN, PKHD1, RECQL4, SMARCB1, TPP1, INVS, MC1R, NCOA2, PKP2, RET, SMC1A, TRAF5, IRAK4, MCCC2, NCOR1, PLEKHG5, RHBDF2, SMC3, TRIO, ITCH, MCOLN1, NDUFA13, PLN, RNASEL, SMO, TRPV4, TRRAP, U2AF1, USH1C, WAS, WWP1, ZIC3, TSC1, U2AF2, USH1G, WBSCR17, XPA, ZNF2, TSC2, UBA1, USP16, WEE1, XPC, ZNF226, TSHB, UBR3, USP25, WNK2, XRCC3, ZNF473, TSHR, UROD, VCL, WRN, ZBED4, ZNF595, TTN, UROS, VHL, WT1, ZFHX3, HER2, and ZRSR2. In a certain embodiment, the gene silencing nucleic acid suppresses the expression of MCL-1. In a further embodiment, the one or more anticancer agents are selected from the group consisting of angiogenesis inhibitors, tyrosine kinase inhibitors, PARP inhibitors, alkylating agents, vinca alkaloids, anthracyclines, antitumor antibiotics, antimetabolites, topoisomerase inhibitors, aromatase inhibitors, mTor inhibitors, retinoids, and HDAC inhibitors. In yet a further embodiment, the angiogenesis inhibitors are selected from a group consisting of axitinib, bevacizumab, cabozantinib, everolimus, lenalidomide, lenvatinib mesylate, pazopanib, ramucirumab, regorafenib, sorafenib, sunitinib, thalidomide, vandetanib, and Ziv-aflibercept. In another embodiment, the PARP inhibitors are selected from a group consisting of olaparib, niraparib, rucaparib, and talzoparib. In yet another embodiment, the tyrosine kinase inhibitor is selected from the group consisting of adavosertib, afatinib, axitinib, binimetinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, neratinib, nilotinib, pazopanib, pegaptanib, ruxolitinib, sorafenib, sunitinib, trametinib, sU6656, PLX4720, PD98059, vandetanib, and vemurafenib. In another embodiment, the surface of the ChNPs have been modified to comprise a targeting moiety that targets the ChNPS to a certain cell type, a certain tissue type, a certain organ or a tumor. In yet another embodiment, the surface of the ChNPs have been modified to comprise a ligand that binds to a tumor-specific antigen. In a further embodiment, the ligand is an antibody or a scFv. In yet a further embodiment, the ligand is attached to the surface of the ChNPs via a cleavable linker. In another embodiment, the cleavable linker is an acid-labile linker, a protease cleavable linker, or a disulfide linker. In yet another embodiment, the tumor-specific antigen is selected from alphafetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu. In a certain embodiment, the one or more ChNPs are parenterally administered. In another embodiment, the one or more anticancer agents are parenterally, and/or orally administered. In yet another embodiment, the one or more ChNPs are concurrently or sequentially co-administered with the one or more anticancer agents. In a further embodiment, the combined administration of the one or more anticancer agents with the one or more ChNPs provides a synergistic effect in killing cancer cells.

30 cells. IC25 and IC50 values were determined by delivering a range of concentrations to ZR-75-30 cells and determining which concentrations killed 25% and 50% of the cells respectively. The concentrations of lapatinib were delivered to cells with or without ChNPs at a concentration of 1e10 GCs/mL of ChNPs. Viability was measured 3 days after delivery. Lapatinib and ChNPs were shown to be synergistic, with both the combinations of ChNPs and lapatinib having CI values of 1.3 for both the IC25 and IC50 amounts of lapatinib.

Figure 12A:
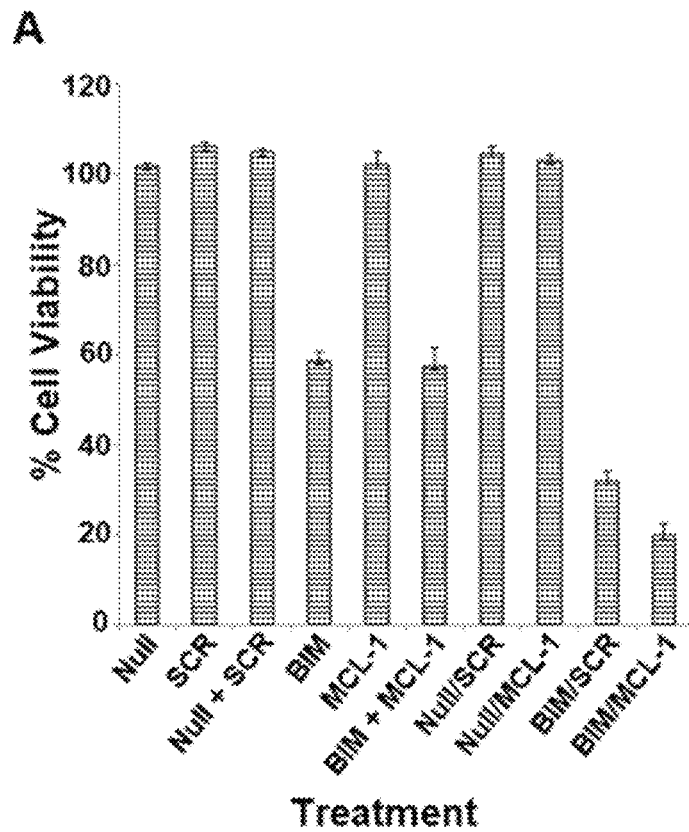
Figure 12B:
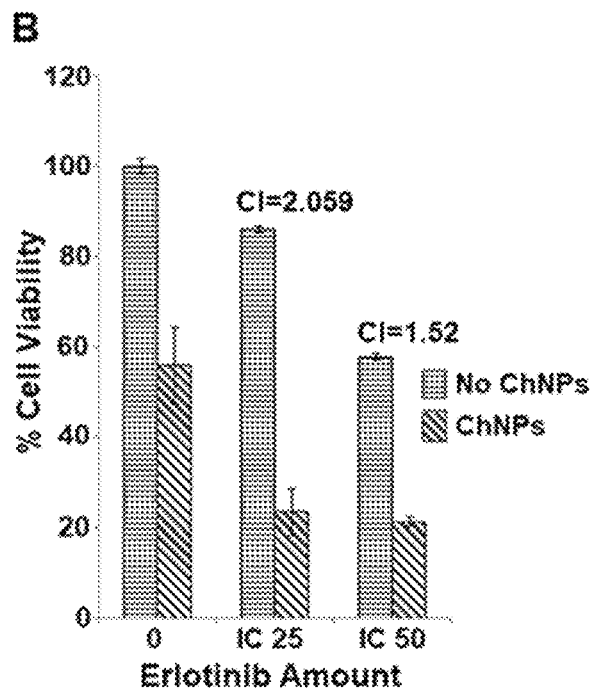

FIG. 12A-B provides for an MDA-MB-468 triple negative breast cancer model that was treated with ChNPs and Erlotinib. The cell line used in this study is MDA-MB-468, which is a triple negative breast cancer cell line with an EGFR mutation. (A) The MDA-MB-468 cells were plated and treated with various groups of AAV, siRNA, AAV and siRNA, and ChNPs containing different AAV and siRNA in the particles. Each was delivered at a concentration of 1e10 GCs/mL AAV, 0.75 ug/mL of siRNA, or both depending on what was being delivered. The BIM/MCL-1 combination outperformed all groups, with BIM/SCR nanoparticles performing better than BIM AAV alone. (B) The combined effect of erlotinib (TKI to treat EGFR mutations) with BIM/MCL-1 ChNPs was tested in the MDA-MB-468 cells. IC25 and IC50 values were determined by delivering a range of concentrations to MDA-MB-468 cells and determining which concentrations killed 25% and 50% of the cells respectively. The concentrations of erlotinib were delivered to cells with or without ChNPs at a concentration of 1e10 GCs/mL of ChNPs. Viability was measured 3 days after delivery. Erlotinib and ChNPs were shown to be synergistic, with a CI value of 2.059 for the IC25 value and CI of 1.52 for IC50.

Figure 13:
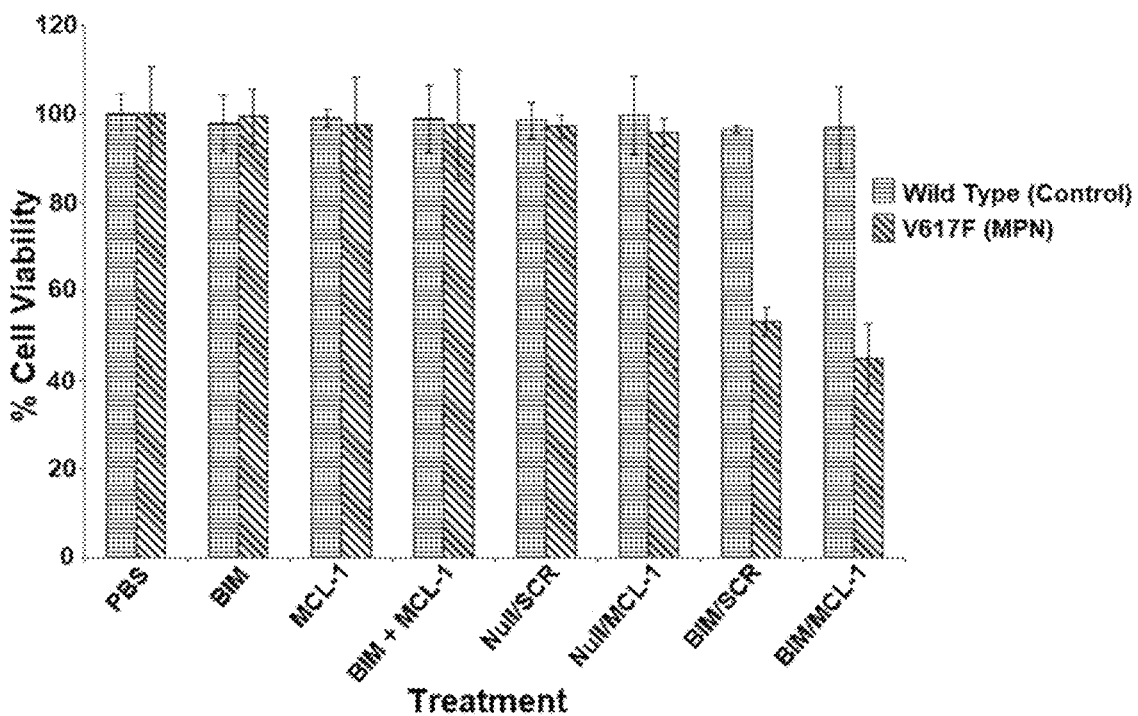

FIG. 13 provides for a BaF3 MPM model assessing the viability of BaF3 cells when treated with various agents. Myeloproliferative neoplasms (MPN) are a blood cancer that lead to overproduction of red blood cells, white blood cells, and platelets. This can cause many side effects as it causes issues with blood flow as there are too many cells. In the figure, two cell lines were used, both BaF3 cells. One is a wild type control "healthy" cell line, while the other has a jak2v617f mutation that is the cause of MPN. Viruses, siRNA, and ChNPs were delivered to these cells at a concentration of 1e10 GCs/mL AAV, 0.75 ug/mL of siRNA, or both depending on what was being delivered. The BIM ChNPs showed greater efficacy than any of the unencapsulated groups, though there did not appear to be a synergistic effect between BIM and MCl-1 for the ChNPs.

Figure 14A:
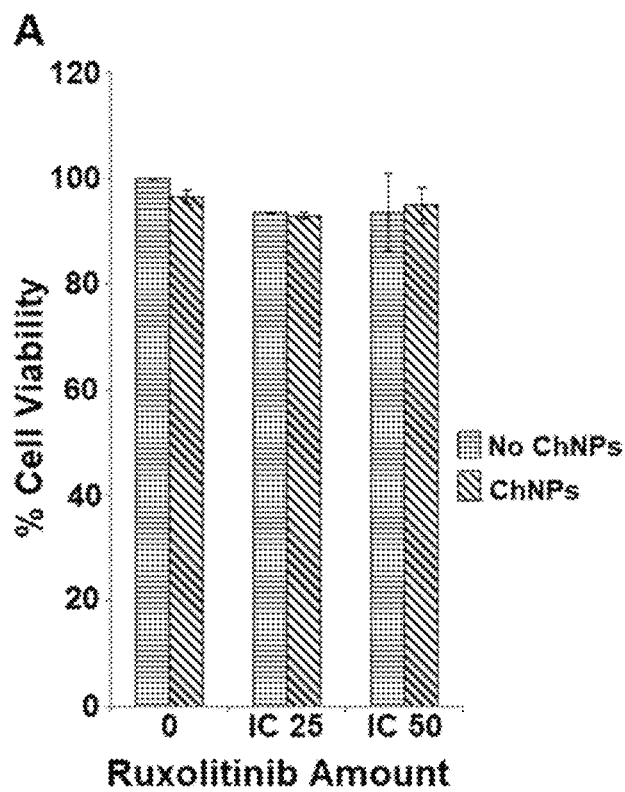
Figure 14B:
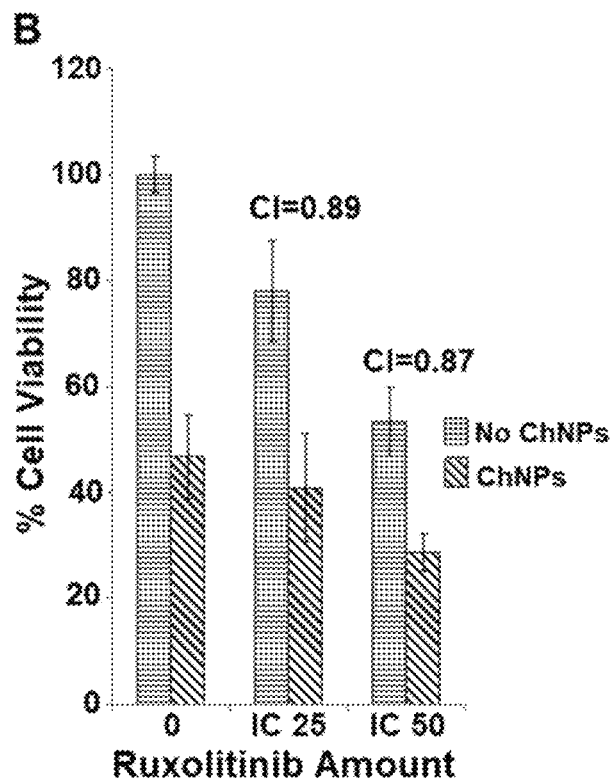

FIG. 14A-B provides for a BaF3 MPN model that was treated with ChNPs and Ruxolitinib. Two cell lines were used, both BaF3 cells: (A) wild type control "healthy" BaF3 cells; and (B) BaF3 cells with a jak2v617f mutation that is the cause of MPN. Ruxolinib (TKI for MPNs) was first delivered to BaF3 cells with the V617F mutation to determine IC25 and IC50 values. Then this amount of ruxolitinib was delivered to both healthy and diseased cells, with and without ChNPS (BIM/MCL-1) at a concentration of 1e10 GCs/mL. Viability was assessed 3 days later. In this case ruxoltinib and ChNPs appeared to have an additive to antagonist effect with CI values of 0.89 and 0.87 for the IC25 and IC50 drug concentrations respectively (B).

Figure 15A:
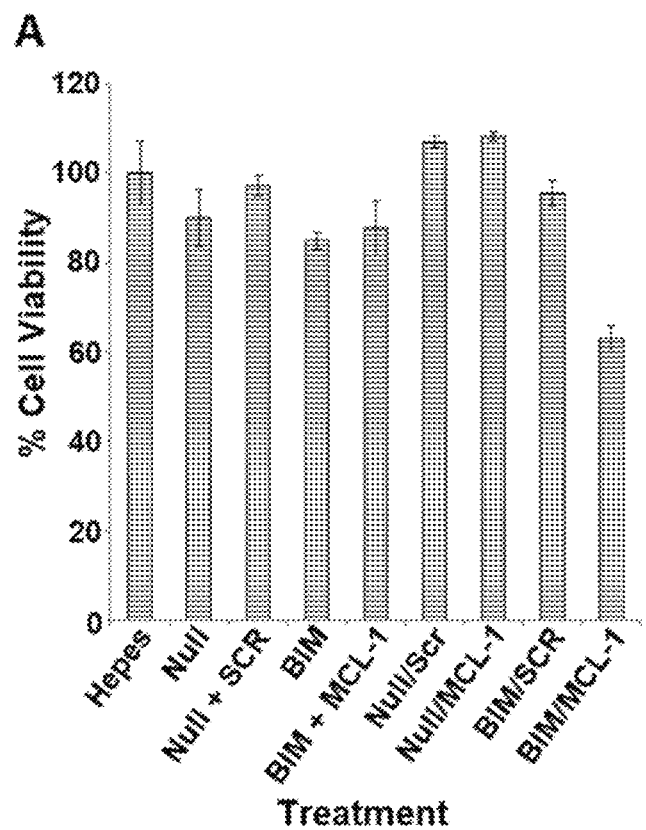
Figure 15B:
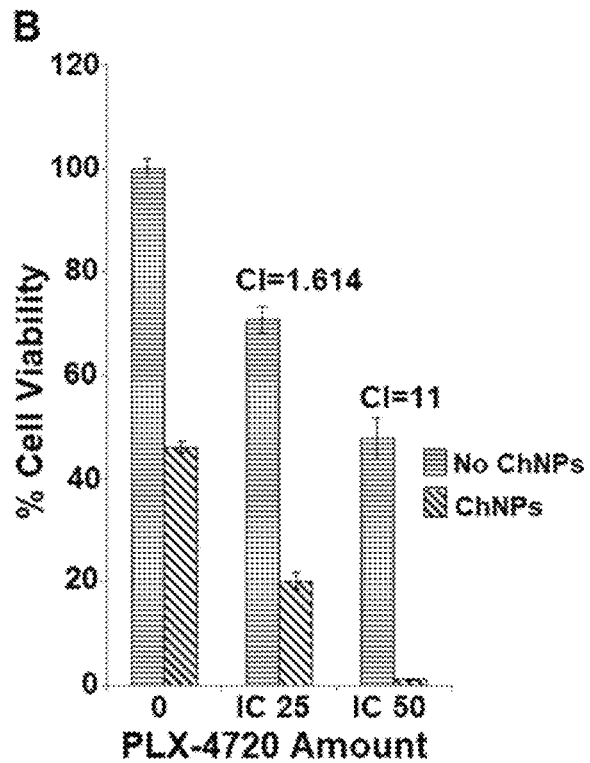

FIG. 15A-B provides for an A375 (Braf+) Melanoma Model that was treated with ChNPs and PLX-4720. The cell line used in this study is A375, which is a melanoma with a Braf mutation. (A) The A375 cells were plated and treated with various groups of AAV, siRNA, AAV and siRNA, and ChNPs containing different AAV and siRNA in the particles. Each was delivered at a concentration of 1e10 GCs/mL AAV, 0.75 ug/mL of siRNA, or both depending on what was being delivered. The BIM/MCL-1 combination outperformed all groups, with BIM/SCR nanoparticles performing better than BIM AAV alone. Viability was assessed three days after delivery. (B) The combined effect of PLX-4720 (TKI to treat Braf mutations) with Bim/Mcl-1 ChNPs was tested in the A375 cells. IC25 and IC50 values were determined by delivering a range of concentrations to A375 cells and determining which concentrations killed 25% and 50% of the cells respectively. The concentrations of PLX-4720 were delivered to cells with or without ChNPs at a concentration of 1e10 GCs/mL of nanoparticles. Viability was measured 3 days after delivery. PLX-4720 and ChNPs were shown to be synergistic, with a CI value of 1.615 for the IC25 value and CI of 11 for IC 50.

Figure 16A:
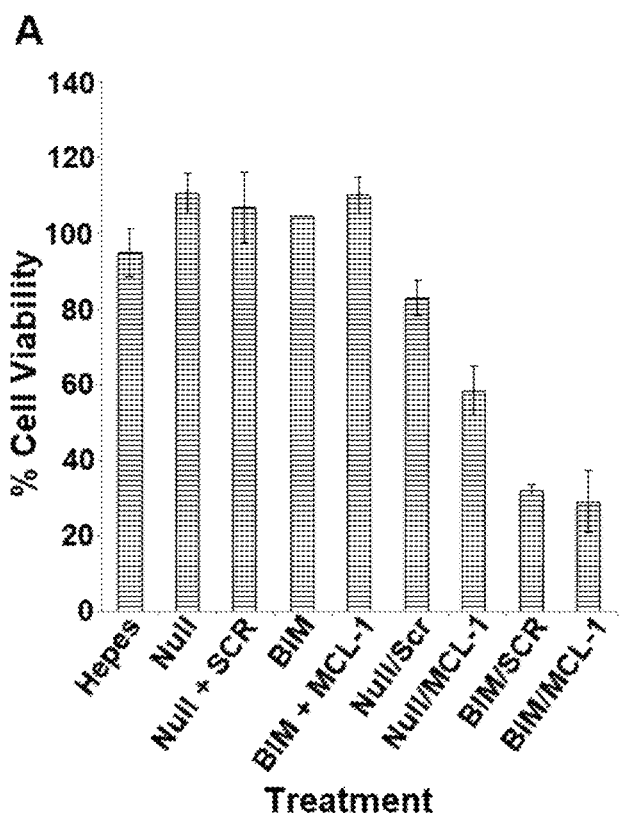
Figure 16B:
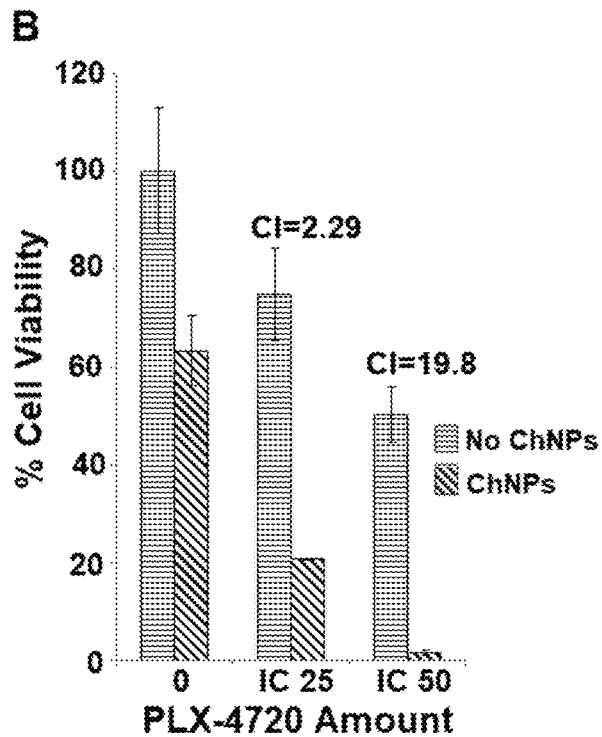

FIG. 16A-B provides for a Sk-Mel-28 (Braf+) Melanoma Model that was treated with ChNPs and PLX-4720. The cell line used in this study is Sk-Mel-28, which is a melanoma with a Braf mutation. (A) The Sk-Mel-28 cells were plated and treated with various groups of AAV, siRNA, AAV and siRNA, and ChNPs containing different AAV and siRNA in the particles. Each was delivered at a concentration of 1e10 GCs/mL AAV, 0.75 ug/mL of siRNA, or both depending on what was being delivered. The BIM/MCL-1 combination outperformed all groups, with BIM/SCR nanoparticles performing better than BIM AAV alone. Viability was assessed three days after delivery. (B) The combined effect of PLX-4720 (TKI to treat Braf mutations) with BIM/MCL-1 ChNPs was tested in the Sk-Mel-28 cells. IC25 and IC50 values were determined by delivering a range of concentrations of PLX-4720 to Sk-Mel-28 cells and determining which concentrations killed 25% and 50% of the cells respectively. The concentrations of PLX-4720 were delivered to cells with or without ChNPs at a concentration of 1e10 GCs/mL of nanoparticles. Viability was measured 3 days after delivery. PLX-4720 and CHnPs were shown to be synergistic, with a CI value of 2.29 for the IC25 value and CI of 19.8 for IC 50.

Figure 17A:
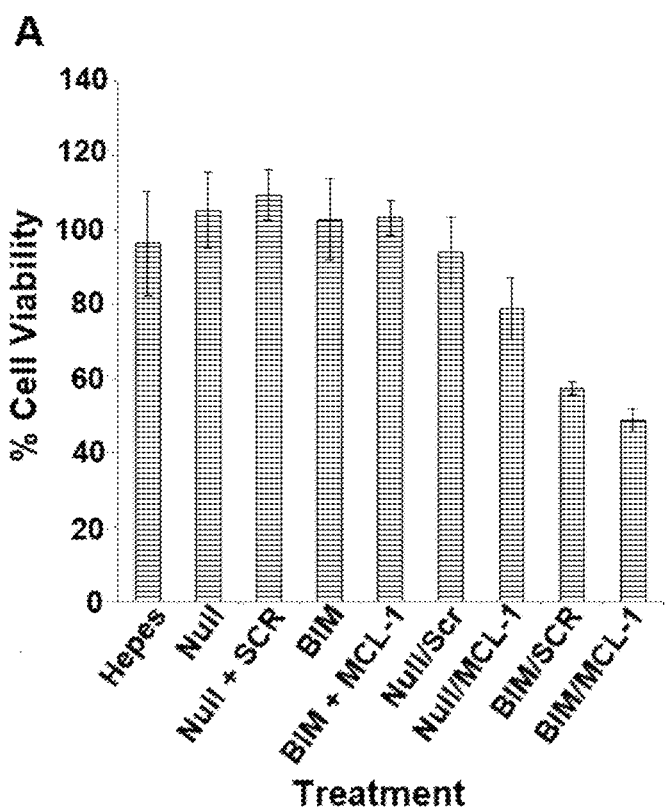
Figure 17B:
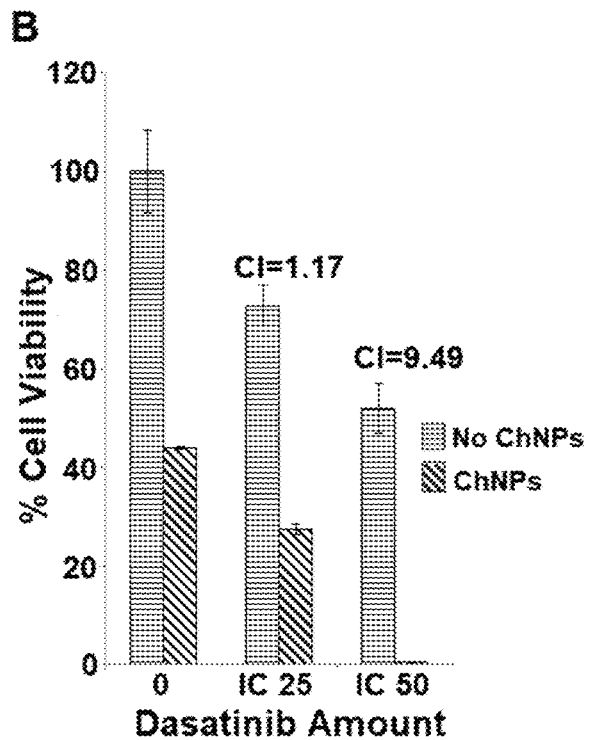

FIG. 17A-B provides for a WM3211 (Kit+) melanoma model that was treated with ChNPs and dasatinib. The cell line used in this study is WM3211, which is a melanoma with a Kit mutation. (A) The WM3211 cells were plated and treated with various groups of AAV, siRNA, AAV and siRNA, and ChNPs containing different AAV and siRNA in the particles. Each was delivered at a concentration of 1e10 GCs/mL AAV, 0.75 ug/mL of siRNA, or both depending on what was being delivered. The BIM/MCL-1 combination outperformed all groups, with BIM/SCR nanoparticles performing better than BIM AAV alone. Viability was assessed three days after delivery. (B) The combined effect of Dasatinib (TKI that has shown to be effective on Kit mutated melanomas) with BIM/MCL-1 ChNPs was tested in the WM3211 cells. IC25 and IC50 values were determined by delivering a range of concentrations to WM3211 cells and determining which concentrations killed 25% and 50% of the cells respectively. The concentrations of Dasatinib were delivered to cells with or without ChNPs at a concentration of 1e10 GCs/mL of nanoparticles. Viability was measured 3 days after delivery. Dasatinib and ChNPs were shown to be synergistic, with a CI value of 1.17 for the IC25 value and CI of 9.49 for IC 50.

Figure 18A:
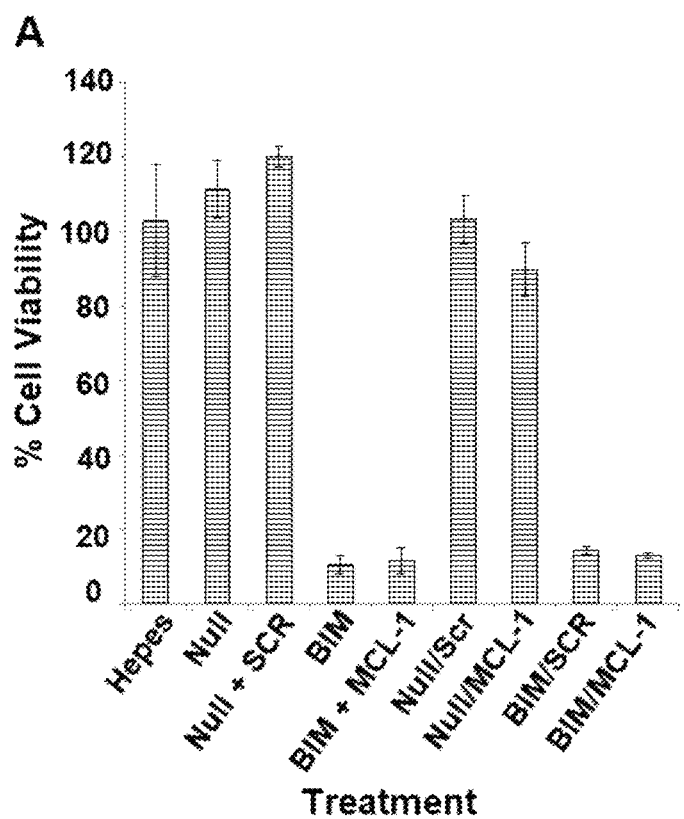
Figure 18B:
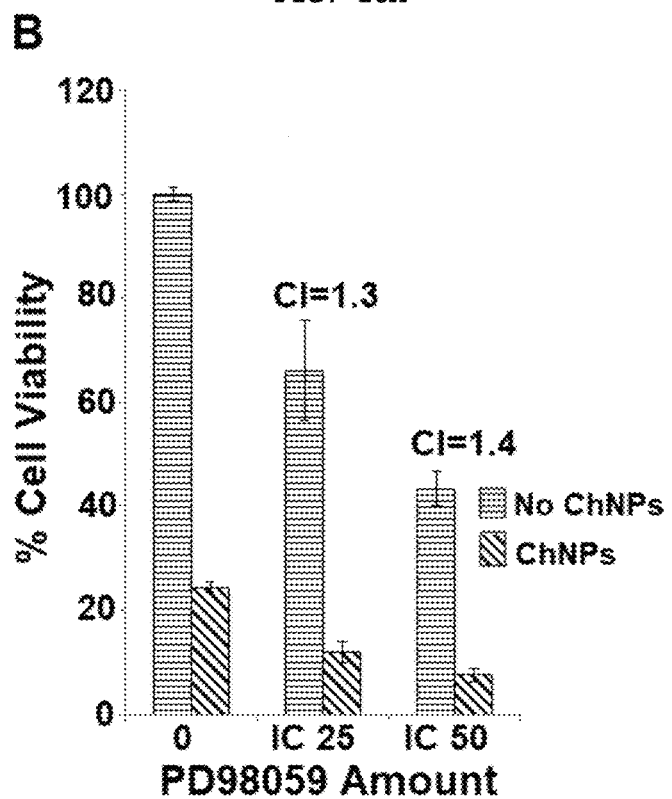

FIG. 18A-B provides for a Sk-Mel-2 (Nras+) Melanoma Model that was treated with ChNPs and PD98059. The cell line used in this study is Sk-Mel-2, which is a melanoma with a Nras mutation. (A) The Sk-Mel-2 cells were plated and treated with various groups of AAV, siRNA, AAV and siRNA, and ChNPs containing different AAV and siRNA in the particles. Each was delivered at a concentration of 1e10 GCs/mL AAV, 0.75 ug/mL of siRNA, or both depending on what was being delivered. The BIM/MCL-1 combination outperformed all groups, with BIM/SCR nanoparticles performing better than BIM AAV alone. Viability was assessed three days after delivery. (B) The combined effect of PD89059 (TKI to treat MEK mutations which is also used to treat Nras mutations) with BIM/MCL-1 ChNPs was tested in the Sk-Mel-2 cells. IC25 and IC50 values were determined by delivering a range of concentrations to Sk-Mel-2 cells and determining which concentrations killed 25% and 50% of the cells respectively. The concentrations of PD98059 were delivered to cells with or without ChNPs at a concentration of 1e10 GCs/mL of ChNPs. Viability was measured 3 days after delivery. PD98059 and ChNPs were shown to be synergistic, with a CI value of 1.3 for the IC25 value and CI of 1.4 for IC 50.

FIG. 19 provides for a pro-apoptosis gene list. The genes, the gene accession numbers and sequences presented therein are incorporated in full for this disclosure.

FIG. 20 provides for a tumor suppressor gene list. The genes, the gene accession numbers and sequences presented therein are incorporated in full for this disclosure.

DETAILED DESCRIPTION

As used herein and in the appended claims, the singular forms "a," "an," and "the" include plural referents unless the context clearly dictates otherwise. Thus, for example, reference to "a polymer layer" includes a plurality of such polymer layers and reference to "the Adeno-associated virus" includes reference to one or more Adeno-associated viruses and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

For purposes of the disclosure the term "cancer" will be used to encompass cell proliferative disorders, neoplasms, precancerous cell disorders and cancers, unless specifically delineated otherwise. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In a particular embodiment, the cancer is selected from the group consisting of melanoma, colorectal cancer, pancreatic cancer, bladder cancer, breast cancer, triple negative breast cancer, ovarian cancer and lung cancer.

Abnormalities in biological homeostasis often result from an imbalance in molecular signaling caused at the genetic level. For example, simultaneous upregulation of the bcl-2 gene with the suppression of pro-apoptotic p53 gene results in increased cancer cell survival. As such, the disclosure provides a way to disrupt these pathway imbalances by inhibiting the expression of cancer promoting genes while simultaneously over expressing therapeutic anticancer genes by the combined use of gene silencing technology with gene therapy, respectively. By use of the multimodal therapies described herein, synergistic anticancer effects can be realized.

In certain embodiments, multimodal therapies described herein comprise co-delivery of a transgene and gene silencing nucleic acids (e.g., siRNA) using a single carrier platform, in order to minimize discrepancies in pharmacokinetics and biodistribution in vivo. More importantly, in order to be appropriately processed and effective, the transgene and the gene silencing nucleic acids are transported to the nucleus and cytoplasm, respectively. Selectively controlled, ordered, and targeted delivery of therapeutic nucleic acids to intracellular targets will also maximize therapeutic efficacy, while reducing undesired side effects.

The development and progression of cancer is promoted by unbalanced homeostasis in the growth of cells, which is largely attributed to the suppression of apoptotic pathways and the increased expression of survival pathways. Cancer therapy, in general, aims to correct such unbalanced homeostasis by promoting cancer death by restoration or promotion of apoptotic pathways or suppression cell survival pathways by use of pharmaceutical agents (e.g., anticancer agents) and/or use of therapies (e.g., radiation therapy). For example, tyrosine kinases (TKs) are promising targets in cancer therapy due to their crucial roles in driving cellular proliferation, apoptosis, and angiogenesis. A well-documented TK-mediated pathogenic example is Philadelphia chromosome positive (Ph+) chronic myelogenous leukemia (CML). The Ph+ genetic lesion is a reciprocal translocation [t(9;22)(q34;q11)] between the genes encoding the breakpoint cluster region (BCR) and Abelson murine leukemia viral oncogene homologue 1 (ABL), resulting in a fusion protein BCR-ABL endowed with constitutive kinase activity that provides for increased cell proliferation while inhibiting apoptosis. This particular chimeric kinase, though highly linked with CML, can also be found in other forms of leukemia including acute lymphoblastic leukemia (ALL) and acute myeloid leukemia (AML). Characterization of the TKs molecular structures and understanding their roles in tumorigenesis has led to the first TK-specific cancer therapeutic drug, imatinib, which was FDA-approved for the first-line treatment of CML in 2002. Imatinib binds close to the ATP binding site of constitutively activated BCR-ABL and inhibits the proliferation of Ph+ cells as well as induces apoptosis. Despite the impressive clinical results with imatinib, CML patients still face the high likelihood of imatinib-resistant cancer cells from mutations in the kinase domain of BCR-ABL or the activation of compensatory survival pathways. This suggests that the current tyrosine kinase inhibitor (TKI)-mediated chemotherapy, by itself, interferes with cancer progression but fails to eradicate cancer cells, and over time selects for mutated clones resistant to TKIs. Such problems can be minimized or ameliorated by providing multifactorial therapies that utilize tyrosine kinase inhibitors in combination with other cancer treatment options, such as the ChNPs provided herein (i.e., gene therapy+antisense therapy combined in a single delivery device).

Recent progress in deciphering the BCR-ABL pathways has led to a new therapeutic approach to apoptosis-mediated gene therapy. It is well documented that BCR-ABL-mediated leukemic potential is directly regulated by B-cell lymphoma-2 (Bcl-2) family proteins such as Bcl-2-interacting mediator of cell death (BIM) and myeloid cell leukemia-1 (MCL-1); specifically, BIM provokes the apoptosis of leukemia cells but is readily inactivated by MCL-1. Pro-survival MCL-1 and pro-apoptotic BIM counteract each other in the apoptosis pathway, and therefore, the antileukemic effect caused by simultaneous BIM expression and MCL-1 silencing is greater than the effects caused by BIM restoration or MCL-1 silencing alone. Additionally, further synergisms can be realized by inhibiting downstream MCL-1 signaling proto-oncogenic mediators and effectors (e.g., kinases, receptors, etc.). Thus, by providing for such multifactorial therapy can result in more efficacious treatments for inducing apoptosis in cancer cells, such as BCR-ABL$^+$ cancer cells.

Figure 5A:
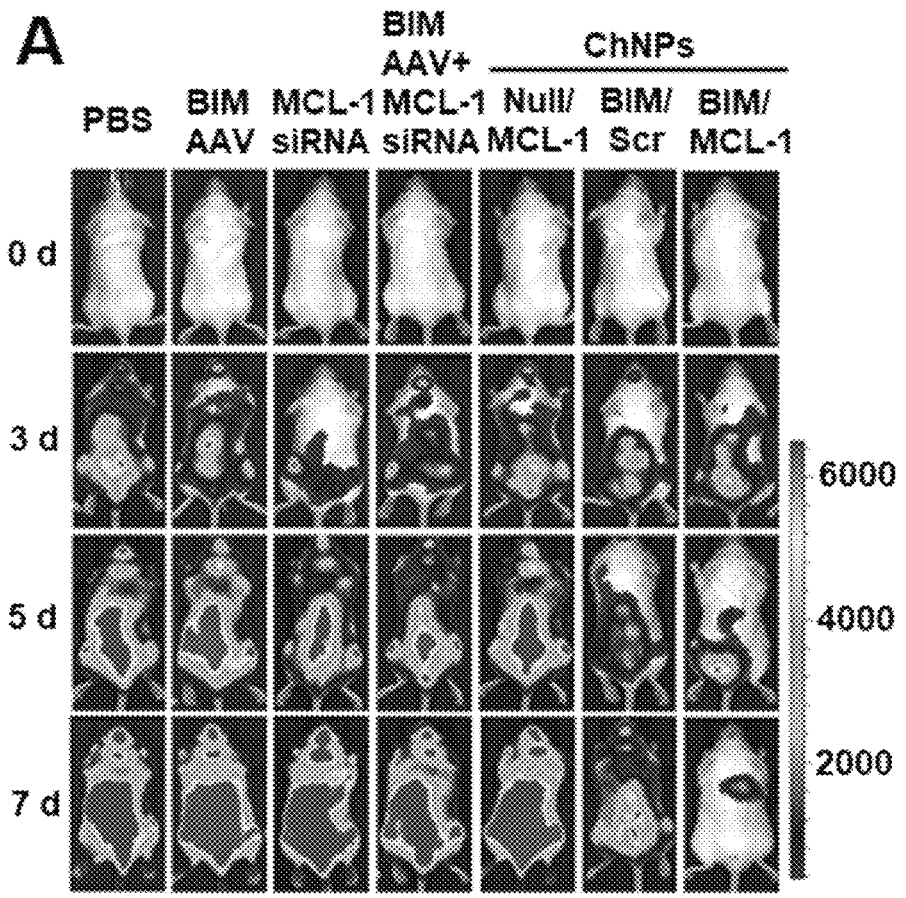
FIG. 5A-B provides the results of in vivo studies with mice using BIM/MCL-1 ChNPs with other agents. (A) Bioluminescence images of FL5.12 p190-Luc cell-carrying BALB/c mice after intravenous injection (once at day 0) with BIM/MCL-1 ChNPs and other agents. (B) Kaplan-Meier survival chart of FL5.12 p190-Luc cell-carrying BALB/c mice treated as in (A). Details along with confirmed low systemic toxicity (spleen size change, whole blood cell counting, and liver enzymatic activity) and low immunogenicity.
Figure 5B:
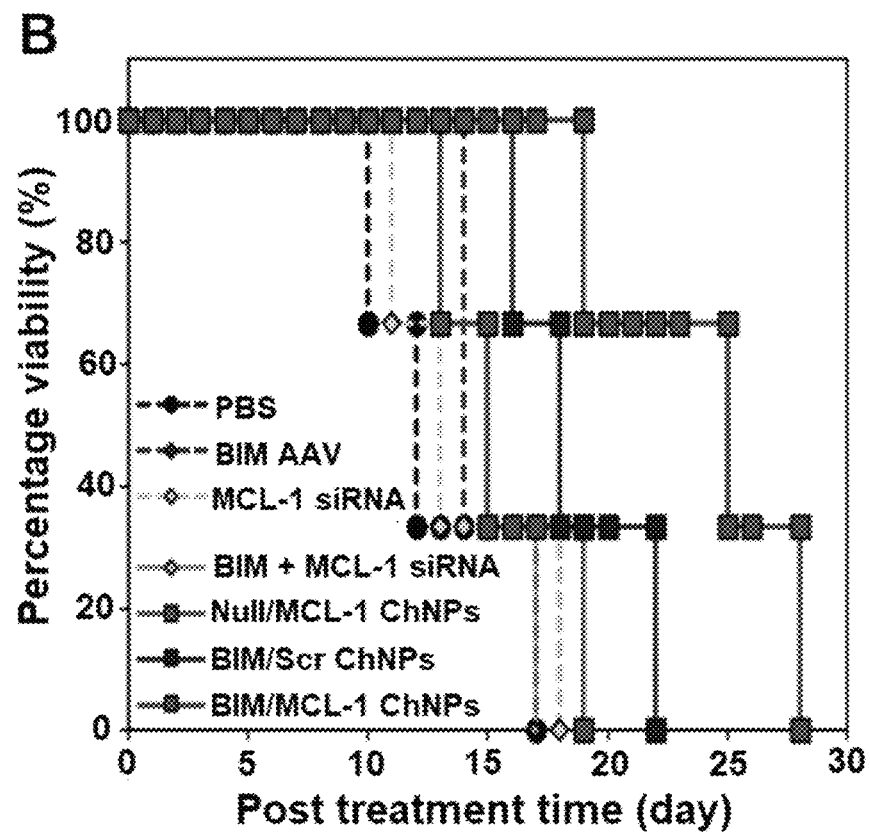

Cancer is a disease attributed to a broad range of molecular abnormalities. Efficient and safe cancer therapy implicates the need for the development of a drug specific to each kind of molecular abnormality. Due to the significant cross-talk between pathways involved in cancer development and progression, single-modal therapy targeting one pathological pathway has seen only limited success. Simultaneously tackling key molecular pathways that are commonly shared by many different kinds of cancers will "universally boost" the efficacy of a "targeted" therapy. For example, pro-apoptotic BIM is downregulated and often counteracted by a pro-survival MCL-1 in many kinds of cancers including leukemia, lung cancer, breast cancer, melanoma, colorectal cancer, ovarian cancer, and more (see FIG. 5 and Table 1). Simultaneous BIM expression and MCL-1 silencing would facilitate the therapeutic efficacy of a downstream acting chemotherapeutic (e.g., protein kinase inhibitors). This approach also avoids development of drug-resistance attributed to mutations in the drug targets (e.g., BCR-ABL and EGFR), activated efflux transporters, and other intermediate pathways (e.g., STAT3).

TABLE 1

Targets and chemotherapeutics associated with a specific type of cancer.

| Type of Cancer | Targets | Chemotherapeutics |
|---|---|---|
| Chronic myelogenous leukemia (CML) | BCR-ABL | Imatinib<br>Dasatinib<br>Nilotinib<br>Bosutinib<br>Ponatinib |
| Acute lymphoblastic leukemia (ALL) | BCR-ABL | Imatinib<br>Dasatinib<br>Nilotinib<br>Bosutinib<br>Ponatinib |
| Myeloproliferative neoplasms (MPN) | JAK1/JAK2 | Ruxolitinib<br>Momelotinib<br>Pacritinib<br>Fedratinib |
| Non-small cell lung cancer (NSCLC) | VEGF | Bevacizumab<br>Ramucirumab |
| | EGFR | Necitumumab<br>Erlotinib<br>Afatinib |

TABLE 1-continued

Targets and chemotherapeutics associated with a specific type of cancer.

| Type of Cancer | Targets | Chemotherapeutics |
|---|---|---|
|  | ALK | Gefitinib |
|  |  | Osimertinib |
|  |  | Dacomitinib |
|  |  | Crizotinib |
|  |  | Ceritinib |
|  |  | Alectinib |
|  |  | Brigatinib |
|  |  | Lorlatinib |
|  | BRAF | Dabrafenib |
|  |  | Trametinib |
| Breast cancer | HER2 | Trastuzumab |
|  |  | Pertuzumab |
|  |  | Lapatinib |
|  |  | Neratinib |
|  | CDKs | Everolimus |
|  | BRCA | Olaparib |
|  |  | Talazoparib |
|  | PIK3CA | Alpelisib |
| Melanoma | BRAF | Vemurafenib |
|  |  | Dabrafenib |
|  |  | Encorafenib |
|  |  | PLX4720 |
|  |  | UO126 |
|  | MEK | Trametinib |
|  |  | Cobimetinib |
|  |  | Binimetinib |
|  | C-KIT | Imatinib |
|  |  | Nilotinib |
|  | NRAS | binimetinib |
|  |  | PD98059 |
| Colorectal | VEGF | Bevacizumab |
|  |  | Ramucirumab |
|  |  | Ziv-aflibercept |
|  | EGFR | Cetuximab |
|  |  | Panitumumab |
| Ovarian | VEGF | Bevacizumab |
|  | BRCA | Olaparib |
|  |  | rucaparib |
|  |  | niraparib |

Source: American Cancer Society

Simultaneously expressing and silencing multiple genes is a daunting task using ether viral or nonviral gene carriers. Provided herein are innovative viral/nonviral hybrid gene vectors that can be used as a therapy option for treating cancer. In a particular embodiment, the ChNPs of the disclosure comprise a viral core of a recombinant adeno-associated virus (AAV). AAV allows for efficient transgene expression in cancer cells; is not linked with human illness; cannot replicate without a helper virus; and integrates its genome into a specific region in human chromosome 19 (i.e., low risk of mutagenesis), making it a widely-used vector in human gene therapy. In a certain embodiment, the AAV has been modified to express a transgene that encodes for one or more pro-apoptosis gene products. Examples of pro-apoptosis gene products include, but are not limited to, the pro-apoptosis genes and products made therefrom listed in FIG. 19. In a further embodiment, the AAV has been modified to express a transgene that codes for one or more tumor suppressor gene products. Examples of tumor suppressor gene products include, but are not limited to, the tumor suppressor genes and products made therefrom listed in FIG. 20. In yet a further embodiment, the AAV has been modified to express a multicistronic transgene that codes for one or more pro-apoptosis gene products and one or more tumor suppressor gene products. In such a case, the protein coding regions can be separated by self-cleaving peptide sequences (e.g., 2A peptides) or IRES sequences. Examples for construction of such multicistronic AAV vectors can be found at Lewis et al., *Journal of Neuroscience Methods* 256:22-29 (2015)), and US20130281516A, which disclosures are incorporated herein in-full. In a particular embodiment, the AAV encodes a transgene that at least encodes BIM.

Figure 1A:
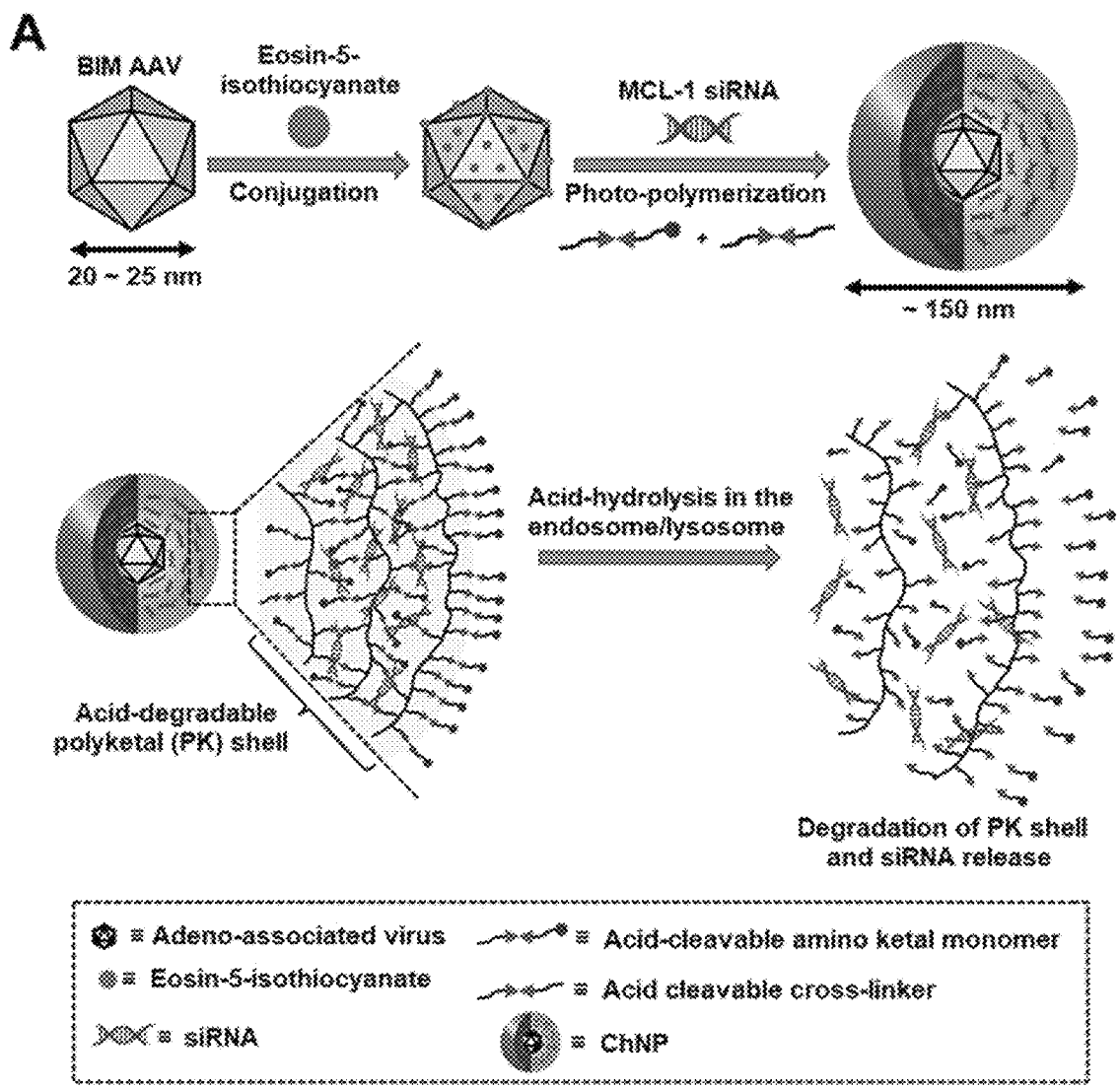
FIG. 1A-B provides an embodiment for the syntheses of viral/nonviral chimeric nanoparticles of the disclosure which simultaneously express BIM and silence MCL-1 (BIM/MCL-1 ChNPs); and further, presents a process by which BIM/MCL-1 ChNPs in BCR-ABL$^+$ cells act synergistically to induce apoptosis. (A) Syntheses of BIM/MCL-1 ChNPs and acid degradation in a cell. BIM-encoding AAV (serotype 2) was encapsulated by an acid-degradable polyketal (PK) shell via photopolymerization of acid-cleavable amino ketal monomers and cross-linkers with the photoinitiator eosin. During the polymerization, MCL-1 siRNA is premixed with the amino ketal monomers in order to provide concurrent encapsulation in the PK shell. The resulting viral/nonviral nanoparticles comprise a BIM AAV core and an acid-degradable, MCL-1 siRNA encapsulating PK shell (BIM/MCL-1 ChNPs). The PK shell is synthetically programmed to degrade in the mildly acidic endosome/lysosome environment, thereby releasing MCL-1 siRNA and BIM AAV to affect intracellular processes. (B) Diagram showing how BIM/MCL-1 ChNPs simultaneously increases BIM expression and silences MCL-1 expression in a BCR-ABL$^+$ leukemia cell. The AAV core and siRNA in BIM/MCL-1 ChNPs are shielded from the immune system and are protected against degradation by nucleases. Upon endocytosis, the PK shell rapidly degrades in the mildly acidic endosome/lysosome and the BIM AAV core and MCL-1 siRNA are released into the cytoplasm to affect intracellular processes. The siRNA released into the cytoplasm silences the expression of pro-survival MCL-1. Concurrently, AAV is transported into the nucleus and provides for the expression of BIM, whose transcription and half-life are interfered with by BCR-ABL-initiated pathways. Re-sensitization to BIM-mediated apoptosis via MCL-1 silencing combined with restored apoptosis by BIM expression, provides for the synergistic suppression of the proliferation of BCR-ABL$^+$ leukemia cells.
Figure 1B:
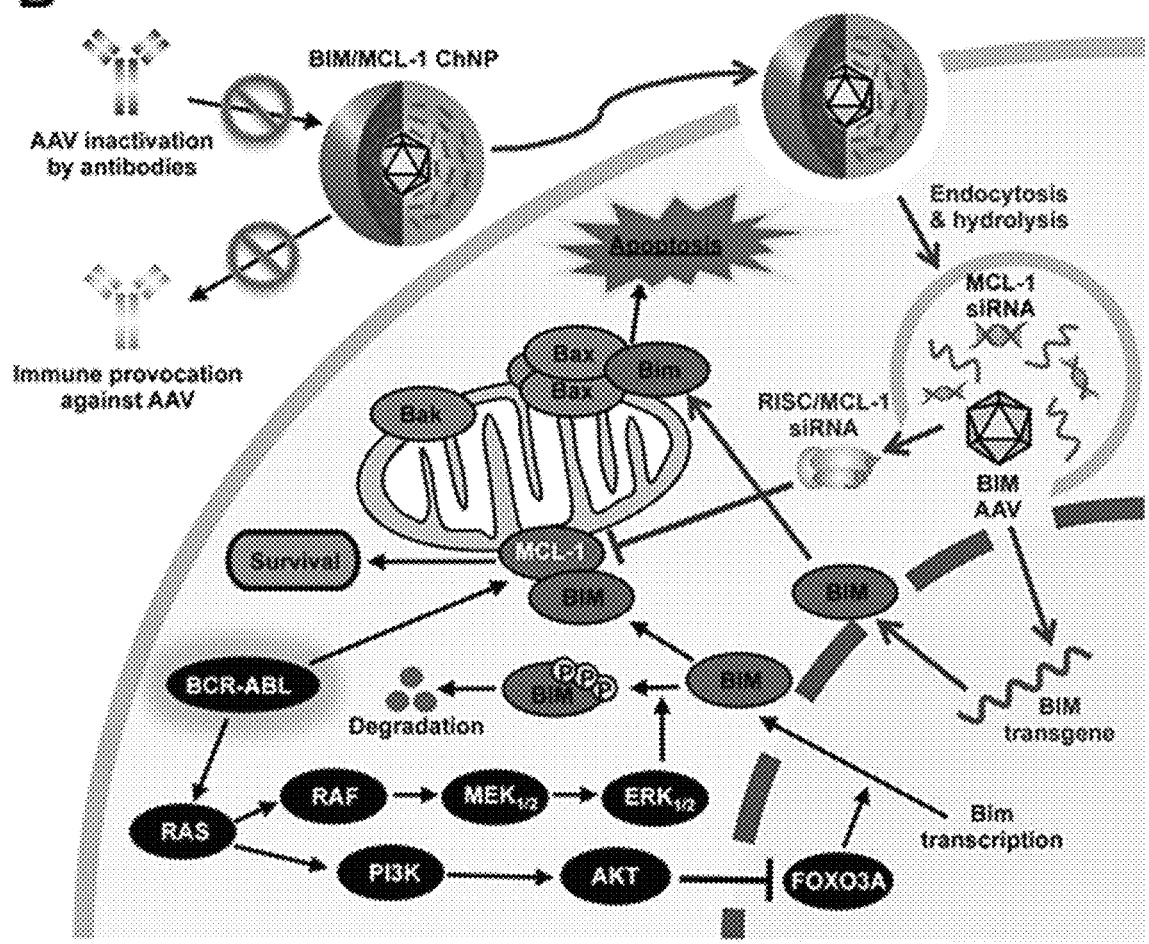
Figure 2:
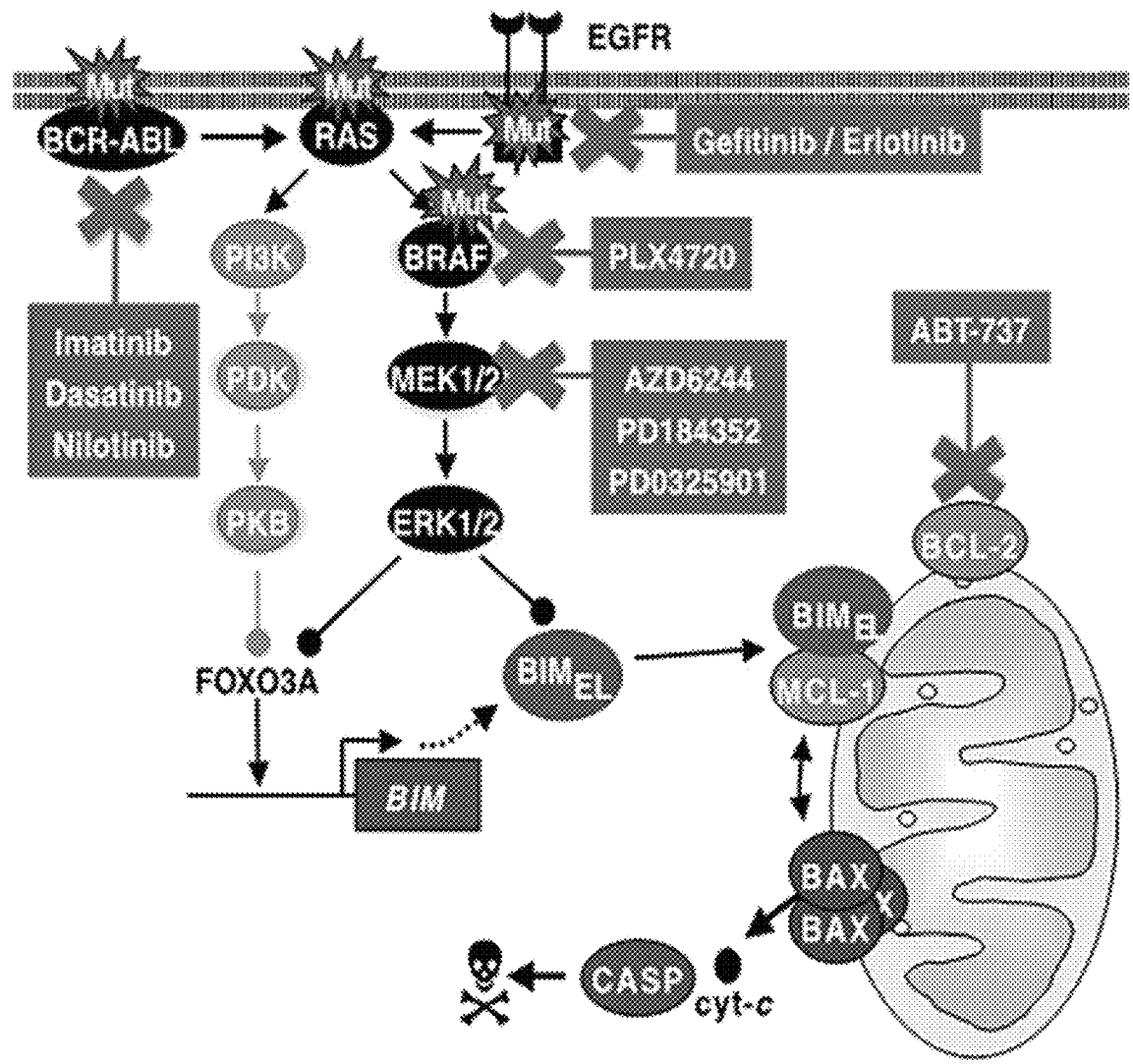
FIG. 2 demonstrates the pivotal roles of BIM and MCL-1 in apoptosis for different types of cancers.

The AAV viruses disclosed herein have been modified to comprise acid-degradable polymeric layer(s) designed to encapsulate gene silencing/editing nucleic acids (e.g., siRNA) that can rapidly hydrolyze in the mildly acidic endosome. Accordingly, as used herein the term "chimeric nanoparticles" or "ChNPs" refers to nanoparticles that comprise an AAV viral core that expresses a transgene which encodes heterologous gene product(s), such as the pro-apoptosis genes presented in FIG. 19 and/or the tumor suppressor genes presented in FIG. 20, which is surrounded by one or more shells or layers of acid labile polymers which comprise gene silencing/editing nucleic acids (e.g., siRNAs, asRNAs, or miRNAs). The polymeric shell also shields the AAV core from a host's immune response and promotes the cytoplasmic release of the gene silencing/editing nucleic acids in the acidic environment of the endosome. In a particular embodiment, the disclosure provides for ChNPs which comprise an AAV core that expresses a transgene for BIM, that is surrounded by one or more layers of an acid labile polymer comprising siRNA for MCL-1 (i.e., BIM/MCL-1 ChNPs) (e.g., see FIG. 1). As such, the BIM/MCL-1 ChNPs co-deliver BIM cDNA and MCL-1 siRNA to the same cell, and further are synthetically programed for efficient endosomal escape of their payloads while not provoking an anti-AAV immune response in the host.

In regards to the gene silencing/editing nucleic acids, the sequences of which are generally targeted to suppress expression of gene products from oncogenes. As such, the particular sequence of the antisense oligonucleotide can vary as long as the result is suppression of targeted gene product from an oncogene. In direct contrast, as gene products could be suppressed due to the mutations resulting from a cancer, certain targeted gene products that are suppressed by a cancer (e.g., tumor suppressing genes) may be overexpressed by use of the transgene disclosed herein. Examples of targeted gene products from oncogenes or genes associated with a cancer can be, e.g., found in Table 1. Other targeted gene products from an oncogene or gene associated with a cancer include, but are not limited to, BCR, BRAF, JAK1, JAK2, VEGF, EGFR, ALK, HER2, CDK1, CDK2, CDK3, CDK3, CDK4, BRCA, PIK3CA, MEK, C-KIT, NRAS, MCL-1, ABCB11, ANTXR2, BCOR, CDKN1B, CYP27A1, EMD, FANCF, ABCC8, APC, BCORL1, CDKN2A, CYP27B1, EP300, FANCG, ABCC9, AR, BLM, CEP290, DAXX, EPCAM, FANCI, ABCD1, ARID1A, BMPR1A, CFTR, DBT, EPHA5, FANCL, ABL1, ARID2, BRAF, CHEK1, DCC, EPHB2, FANCM, ACADM, ARSA, BRCA1, CHEK2, DCX, ERBB2, FAS, CADS, ASAH1, BRCA2, CHM, DDB2, ERBB3, FAT3, ACADVL, ASCC1, BRIP1, CIC, DDR2, ERBB4, FBXO11, ACTC1, ASL, BTD, CLN3, DES, ERCC2, FBXO32, ACTN2, ASPA, BTK, CLN5, DHCR7, ERCC3, FBXW7, ACVR1B, ASS1, BUB1B, CLN6, DICER1, ERCC4, FGD4, ADA, ASXL1, CALR3, CLN8, DIS3L2, ERCC5, FGFR1, ADAMTS13, ATM, CARD11, COL1A2, DKC1, ERCC6, FGFR2, ADAMTS2, ATP4A, CASP8, COL4A3, DLD, ERRFI1, FGFR3, AGA, ATP6V0D2, CAV3, COL4A4, DMD, ESCO2, FH, AGL, ATP7A, CBFB, COL7A1, DNAJB2, ESR1, FKTN, AGPS, ATP7B, CBL, COX15, DNMT3A, ETV6, FLCN, AHI1, ATP8B1, CBLB, CREBBP, DSC2, EXOC2, FLT3, AIP, ATR, CBLC, CRLF2, DSE, EXT1, FMR1, AKAP9, ATRX, CBS, CRTAP, DSC2, EXT2, FUBP1, AKT1, AXIN1, CCDC178, CRYAB, DSP, EYA4, FZD3, AKT2, AXIN2, CCNE1, CSF1R, DTNA, EZH2, G6PC, ALB, BAG3, CD79A, CSMD3, ECT2L, F11, GAA, ALDH3A2, BAI3, CD79B, CSRP3, EDA, F5, GABRA6, ALDOB, BAP1, CD96, CTNNB1, EDN3, FAH, GALNT12, ALK, BARD1, CDC27, CTNS, EDNRB, FAM46C, GALT, ALS2, BAX, CDC73, CTSK, EED, FANCA, GATA1, AMER1, BAZ2B, CDH1, CUBN, EGFR, FANCB, GATA2, AMPD1, BCKDHA, CDH23, CYLD, EGR2, FANCC, GATA3, AMPH, BCKDHB, CDK12, CYP11A1, EHBP1, FANCD2, GATAD1, ANTXR1, BCL6, CDK4, CYP21A2, ELMO1, FANCE, GBA, GCDH, JAK1, MDM2, NEK2, PLOD1, ROS1, SMPD1, GJB2, JAK2, MECP2, NEXN, PLP1, RPGRIP1L, SOX10, GLA, JAK3, MED12, NF1, PMP22, RS1, SOX2, GLB1, JUP, MEFV, NF2, PMS2, RSPO1, SPEG, GLI1, KAT6A, MEN1, NFE2L2, POLD1, RTEL1, SPOP, GLI3, KCNQ1, MET, NFKBIA, POLE, RUNX1, SRC, GLMN, KDM4B, MFSD8, NIPA2, POLH, RUNX1T1, SSTR1, GNA11, KDM6A, MIER3, NKX3-1, POMGNT1, RYR2, STAG2, GNAQ, KDR, MITF, NOTCH1, POMT1, S1PR2, STAR, GNAS, KEAP1, MKS1, NOTCH2, POU1F1, SAMD9L, STK11, GNPTAB, KIF1B, MLH1, NPC1, POU6F2, SBDS, SUFU, GPC3, KIT, MLH3, NPC2, PPM1L, SCN11A, SUZ12, GPC6, KLF6, MMAB, NPHP1, PPP2R1A, SCN5A, SYNE3, GPR78, KLHDC8B, MPL, NPHP4, PPT1, SCNN1A, TAZ, GRIN2A, KMT2A, MPZ, NPM1, PRDM1, SCNN1B, TBX20, GRM8, KMT2C, MRE11A, NRAS, PRKAG2, SCNN1G, TCAP, GXYLT1, KMT2D, MSH2, NRCAM, PRKAR1A, SCO2, TCERG1, H3F3A, KRAS, MSH3, NTRK1, PRKDC, SDHA, TCF7L2, HADHA, KREMEN1, MSH6, NUP62, PROC, SDHAF2, TERT, HADHB, L1CAM, MSMB, OR5L1, PROP1, SDHB, TET2, HBB, LAMA2, MSR1, OTC, PRPF40B, SDHC, TFG, HESX1, LAMA4, MTAP, OTOP1, PRX, SDHD, TGFB3, HEXA, LAMP2, MTHFR, PAH, PSAP, SEPT9, TGFBR1, HEXB, LDB3, MTM1, PALB2, PSEN1, SETBP1, TGFBR2, HFE, LEPRE1, MTOR, PALLD, PSEN2, SETD2, THSD7B, HGSNAT, LIG4, MUC16, PAX5, PTCH1, SF1, TINF2, HIST1H3B, LMNA, MUT, PAX6, PTCH2, SF3A1, TMC6, HNF1A, LPAR2, MUTYH, PBRM1, PTEN, SF3B1, TMC8, HRAS, LRP1B, MYBPC3, PCDH15, PTGFR, SGCD, TMEM127, HSPH1, LRPPRC, MYC, PCGF2, PTPN11, SGSH, TMEM43, IDH1, LRRK2, MYD88, PDE11A, PTPN12, SH2B3, TMEM67, IDH2, LYST, MYH6, PDGFRA, RAC1, SLC25A4, TMPO, IGF2R, MAP2K1, MYH7, PDHA1, RAD21, SLC26A2, TNFAIP3, IGHMBP2, MAP2K2, MYL2, PDZRN3, RAD50, SLC37A4, TNFRSF14, IGSF10, MAP2K4, MYL3, PEX1, RAD51B, SLC7A8, TNNC1, IKBKAP, MAP3K1, MYLK2, PEX7, RAD51C, SLC9A9, TNNI3, IKZF1, MAP4K3, MYO1B, PHF6, RAD51D, SLX4, TNNT1, IKZF4, MAP7, MYO7A, PIK3CA, RARB, SMAD2, TNNT2, IL2RG, MAPK10, MYOZ2, PIK3CG, RB1, SMAD4, TP53, IL6ST, MAS1L, MYPN, PIK3R1, RBM20, SMARCA4, TPM1, IL7R, MAX, NBN, PKHD1, RECQL4, SMARCB1, TPP1, INVS, MC1R, NCOA2, PKP2, RET, SMC1A, TRAF5, IRAK4, MCCC2, NCOR1, PLEKHG5, RHBDF2, SMC3, TRIO, ITCH, MCOLN1, NDUFA13, PLN, RNASEL, SMO, TRPV4, TRRAP, U2AF1, USH1C, WAS, WWP1, ZIC3, TSC1, U2AF2, USH1G, WBSCR17, XPA, ZNF2, TSC2, UBA1, USP16, WEE1, XPC, ZNF226, TSHB, UBR3, USP25, WNK2, XRCC3, ZNF473, TSHR, UROD, VCL, WRN, ZBED4, ZNF595, TTN, UROS, VHL, WT1, ZFHX3, and ZRSR2. Many of the targeted gene products listed above are associated with a particular type of cancer. For example, genes most commonly mutated in human breast cancer samples, include but are not limited to, ACVR1B, CDH1, EXOC2, ITCH, NCOR1, PTEN, WEE1, AKT1, CDKN2A, EXT2, KMT2C, NEK2, PTGFR, ZBED4, ATM, EGFR, FBXO32, MAP2K4, PBRM1, RB1, BAP1, EP300, FGFR1, MAP3K1, PCGF2, RET, BRCA1, ERBB2, FGFR2, MDM2, PIK3CA, SEPT9, BRCA2, ERBB3, GATA3, MUC16, PIK3R1, TP53, CBFB, ESR1, IRAK4, MYC, HER2, PPM1L, and TRAF5; genes most commonly mutated in human colorectal cancer samples, include but are not limited to, ACVR1B, BRAF, EP300, MAP2K4, MSH6, SLC9A9, TP53, AKT1, CASP8, ERBB2, MAP7, MYO1B, SMAD2, WBSCR17, APC, CDC27, FBXW7, MIER3, NRAS, SMAD4, ATM, CTNNB1, FZD3, MLH1, PIK3CA, TCERG1, ATP6V0D2, DCC, GPC6, MSH2, PIK3R1, TCF7L2, BAX, DMD, KRAS, MSH3, PTPN12, and TGFBR2; genes most commonly mutated in human myeloid cancer samples, include but are not limited to, ABL1, DNMT3A, IDH2, KRAS, RAD21, SMC1A, WT1, ASXL1, EED, IKZF1, MPL, RB1, SMC3, ZRSR2, ATRX, ETV6, JAK1, NF1, RUNX1, STAG2, BCOR, EZH2, JAK2, NPM1, SETBP1, SUZ12, BCORL1, FLT3, JAK3, NRAS, SF1, TET2, CBL, GATA1, KAT6A, PHF6, SF3A1, TP53, CBLB, GNAS, KIT, PRPF40B, SF3B1, U2AF1, DAXX, IDH1, KMT2A, PTPN11, SH2B3, and U2AF2; genes most commonly mutated in human liver cancer samples, include but are not limited to, ALB, ATM, CDKN2A, ERBB2, IGSF10, PIK3CA, WWP1, AMPH, AXIN1, CSMD3, ERRFI1, KEAP1, SAMD9L, ZIC3, APC, BAZ2B, CTNNB1, GXYLT1, KRAS, TP53, ZNF226, ARID1A, BRAF, DSE, HNF1A, MET, UBR3, ARID2, CCDC178, ELMO1, IGF2R, OTOP1, and USP25; genes most commonly mutated in human lung cancer samples, include but are not limited to, AKT1, CDKN2A, FGFR2, LRP1B, NFE2L2, RARB, SOX2, ALK, EGFR, GRM8, MDM2, NOTCH1, RB1, STK11, APC, EPHA5, KDR, MET, PDGFRA, RET, TP53, ATM, ERBB2, KEAP1, MLH1, PIK3CA, ROS1, BAI3, ERBB4, KIT, MUC16, PIK3CG, RUNX1T1, BAP1, FBXW7, KMT2D, MYC, PKHD1, SMAD4, BRAF, FGFR1, KRAS, NF1, PTEN, and SMARCA4; genes most commonly mutated in human ovarian cancer samples, include but are not limited to, AKT1, CBLC, CTNNB1, GABRA6, MLH1, PIK3CA, TP53, ARID1A, CCNE1, CUBN, KIT, MSH2, PIK3R1, USP16, BRAF, CDK12, EGFR, KRAS, NF1, PPP2R1A, BRCA1, CDKN2A, ERBB2, KREMEN1, NRAS, PTEN, BRCA2, CSMD3, FAT3, MAS1L, PDGFRA, and RB1; genes most commonly mutated in human prostate cancer samples include, but are not limited to, AKAP9, CDKN2A, KMT2D, NKX3-1, PTEN, TBX20, ZNF473, APC, GLI1, MED12, NRCAM, RB1, TFG, ZNF595, AR, IKZF4, MYC, OR5L1, SCN11A, THSD7B, CDK12, KDM4B, NCOA2, PDZRN3, SPOP, TP53, CDKN1B, KLF6, NIPA2, PIK3CA, SYNE3, and ZFHX3; and genes most commonly mutated in human gastric cancer samples, include but are not limited to, APC, CDH1, FGFR2, MET, RET, TP53, ATP4A, CTNNB1, GPR78, MYC, S1PR2, TRIO, BAI3, DCC, LPAR2, NOTCH1, SPEG, TRRAP, BRCA2, ERBB2, LRP1B, PIK3CA, SSTR1, WNK2, CCNE1, FBXW7, LRRK2, PRKDC, and STK11. Based upon whether the mutation resulting from the cancer causes overexpression or under expression of the gene products determines whether the gene target is targeted for suppression by the gene silencing/editing nucleic acids disclosed herein or targeted for overexpression via an AAV transgene disclosed herein, respectively. It should be noted that the creation of AAV vectors that express any of the genes listed herein as a transgene, can simply use the vectors described in the Examples section where the BIM gene has been replaced with one of the genes listed above. Moreover, many AAV vectors are commercially available, from vendors like Addgene, Vector Biolabs, and Cell Biolabs. Similarly, designing siRNAs or other gene silencing nucleic acids to one of the genes listed herein, can be made by using the known sequences and one of the many publicly accessible programs for designing siRNAs and the like (e.g., see dharmacon.horizondiscovery.com/design-center/; idtdna.com/site/order/designtool/index/DSIRNA_CUSTOM; and rnaidesigner.thermofisher.com/rnaiexpress/).

Provided herein is a multi-modal cancer therapy approach that simultaneously manipulates three or more components of the cell death/survival machinery in order to achieve synergistic enhancement and efficacious therapy for cancer. Ph+ leukemia was used as the model disease for the proof-of-concept study presented herein due to its survival mechanisms being well characterized. Accordingly, the approach presented herein is a platform technology that is not limited to just the exemplary systems presented herein (e.g., treatment of PH+ leukemia), but can be broadly applied to many or most types of cancer. As such, the multi-modal cancer therapy disclosed herein encompasses the following modalities: (1) increasing expression of tumor suppression genes (e.g., p53) and/or apoptotic genes (e.g., BCL genes), (2) decreasing expression of oncogenes known to be associated with a particular type of cancer (e.g., MCl-1 with PH+ leukemia; ABL1 with chronic myeloid leukemia; ARHGEF5 with breast cancer; etc.), and (3) decreasing the activity or expression of proto-oncogenic mediators and effectors (e.g., tyrosine kinases), or other chemotherapeutic targets (e.g., polymerases). It should be understood that for the methods disclosed herein, more than one type of ChNPs may be administered concurrently or sequentially to a subject. As such, the disclosure contemplates use of 1, 2, 3, 4, 5, 6, 7, 8, 9, 10 or more types of ChNPs, where the ChNPs differ by the sequence of gene silencing or gene editing oligonucleotide, and/or product(s) expressed by the transgene.

In yet a further embodiment, the disclosure provides for modifying the surface of the ChNPs disclosed herein to comprise targeting ligands. In some embodiments, this targeting ligand may direct the ChNPs to, for example, a cell, cell type, tissue type or organ. For example, the targeting ligand may specifically or non-specifically bind with a molecule on the surface of a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell. For example, the targeting moiety can recognize a tumor-specific antigen.

Any protein produced in a tumor cell that has an abnormal structure due to mutation can act as a tumor-specific antigen. Such abnormal proteins are produced due to mutation of the concerned gene. Mutation of protooncogenes and tumor suppressors which lead to abnormal protein production are the cause of the tumor and thus such abnormal proteins are called tumor-specific antigens. Examples of tumor-specific antigens include the abnormal products of ras and p53 genes. In contrast, mutation of other genes unrelated to the tumor formation may lead to synthesis of abnormal proteins which are called tumor-associated antigens. Other examples include tissue differentiation antigens, mutant protein antigens, oncogenic viral antigens, cancer-testis antigens and vascular or stromal specific antigens. Tissue differentiation antigens are those that are specific to a certain type of tissue. Mutant protein antigens are likely to be much more specific to cancer cells because normal cells shouldn't contain these proteins. Normal cells will display the normal protein antigen on their MHC molecules, whereas cancer cells will display the mutant version. Some viral proteins are implicated in forming cancer (oncogenesis), and some viral antigens are also cancer antigens. Cancer-testis antigens are antigens expressed primarily in the germ cells of the testes, but also in fetal ovaries and the trophoblast. Some cancer cells aberrantly express these proteins and therefore present these antigens, allowing attack by T-cells specific to these antigens. Example antigens of this type are CTAG1B and MAGEA1. Proteins that are normally produced in very low quantities but whose production is dramatically increased in tumor cells, trigger an immune response. An example of such a protein is the enzyme tyrosinase, which is required for melanin production. Normally tyrosinase is produced in minute quantities but its levels are very much elevated in melanoma cells.

Oncofetal antigens are another important class of tumor-specific antigens. Examples are alphafetoprotein (AFP) and carcinoembryonic antigen (CEA). These proteins are normally produced in the early stages of embryonic development and disappear by the time the immune system is fully developed. Thus, self-tolerance does not develop against these antigens.

Abnormal proteins are also produced by cells infected with oncoviruses, e.g. EBV and HPV. Cells infected by these viruses contain latent viral DNA which is transcribed and the resulting protein produces an immune response.

In addition to proteins, other substances like cell surface glycolipids and glycoproteins may also have an abnormal structure in tumor cells and could thus be targets of the immune system. Tumor antigens, because of their relative abundance in tumor cells are useful in identifying specific tumor cells. Certain tumors have certain tumor antigens in abundance.

In a particular embodiment, the disclosure provides for ChNPs that further comprise a targeting ligand, wherein the targeting ligand directs the ChNPs of the disclosure to a certain cell, cell type, tissue type, tumor, or organ. In yet a further embodiment, the ChNPs comprise a ligand (e.g., an antibody, or fragment thereof (scFV)), which binds to a tumor-specific antigen. Such tumor-specific ChNPs are designed to kill cancer cells in a target-dependent manner. Ligands to tumor-specific antigens are commercially available from a variety of vendors, and therefore do not have to be generated de novo (e.g., see Elabscience, Santa Cruz biotechnology, Biospacific, Novus Biologicals, etc.). The tumor-specific antigen should be localized on the cell-surface so it can be accessed by a circulating antibody. Upon binding of the tumor-specific ChNPs, the entire antigen/tumor-specific ChNP complex is internalized through receptor-mediated endocytosis. This process generally occurs when a ligand binds a cell-surface receptor and initiates a cascade of events, including recruitment of adaptins and clathrin, inward budding of the plasma membrane, formation of early endosomes, and lastly trafficking to late endosomes and lysosomes. Once inside lysosomes, antigen/tumor-specific ChNP complex are degraded and the antigen and tumor specific ligand are released from the ChNPs and the acid labile degradable polymer layer(s) are degraded, thereby freeing the encapsulated gene silencing/editing nucleic acids and exposing the recombinant AAV core of the ChNPs. The anticancer effects of such ChNPs is dependent on the payload of the ChNPs and the class of cytotoxic drug used in combination with ChNPs. Neighboring cancer cells may also be killed when recombinant AAVs and gene silencing/editing nucleic acids are released into the tumor environment by the dying cell in a process known as the bystander effect. In a particular embodiment, the ligand attached to the ChNPs binds to a tumor specific antigen selected from alphafetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu. The ligand that binds to the tumor-specific antigen should have bind to the target antigen with high affinity ($K_d<10$ nM) for efficient uptake into target tumor cells and it should be minimally immunogenic. In a further embodiment, the ligand that binds to the tumor-specific antigen is attached to a ChNPs disclosed herein via a use of a cleavable linker (acid-labile linkers, protease cleavable linkers, and disulfide linkers). Acid-labile linkers are designed to be stable at pH levels encountered in the blood, but become unstable and degrade when the low pH environment in lysosomes is encountered. Protease-cleavable linkers are also designed to be stable in blood/plasma, but rapidly release free drug inside lysosomes in cancer cells upon cleavage by lysosomal enzymes. They take advantage of the high levels of protease activity inside lysosomes and include a peptide sequence that is recognized and cleaved by these proteases, as occurs with a dipeptide Val-Cit linkage that is rapidly hydrolyzed by cathepsins. A third type of linker that can be used to attach the ligand to ChNPs contains a disulfide linkage. This linker exploits the high level of intracellular reduced glutathione to release free drug inside the cell. The polymer layer(s) of ChNPs described herein generally comprise functional groups that can facilitate attachment of a ligand to the ChNPs, e.g., primary amine groups. Reagents, like Traut's reagent (2-iminothiolane), MBS (3-maleimidobenzoic acid N-hydroxysuccinimide ester), and SATA (N-succinimidyl S-acetylthioacetate) can convert such primary amine groups to sulfhydryls, which can then form disulfide bonds with ligands comprising cysteine residues. Other reagents, like SPDP (N-succinimidyl 3-(2-pyridyldithio) propionate), SMCC (succinimidyl 4-(N-maleimidomethyl) cyclohexane-1-carboxylate), and Sulfo-SMCC can be used as linkers for attaching ligands to polymers of the ChNPs. Examples of how to use of such groups for attaching ligands to the polymer layer(s) to ChNPs can be found on the worldwide web at labome.com/method/Antibody-Conjugation.html, and the references cited therein, including Safdari et al., *Monoclon Antib Immunodiagn Immunother.* 2013 32:409-12; Joosten V et al., *Microb Cell Fact.* 2003 2:1; Winter et al., *Trends Pharmacol Sci.* 1993 14:139-43; Arbabi et al., Front Immunol. 2017 8:1589; Brinkley et al., *Bioconjug Chem.* 1992 3:2-13; Vlasak et al., *MAbs.* 2011 3:253-63; Ducancel et al., *MAbs.* 2012 4:445-57; McCombs et al., *AAPS J.* 2015; 17:339-51; Hondal R., Protein Pept Lett. 2005 12:757-64; Zimmerman et al., *Bioconjug Chem.* 2014 25:351-61; Traut et al., *Biochemistry.* 1973 12:3266-73; Knight P., *Biochem J.* 1979 179:191-7; Carlsson et al., *Biochem J.* 1978 173:723-37; Peeters J et al., *J Immunol Methods.* 1989 120:133-43; Hashida et al., *J Appl Biochem.* 1984 6:56-63; Avrameas et al., *Immunochemistry.* 1971 8:1175-9; Richards et al., *J Mol Biol.* 1968 37:231-3; Chandler et al., *J Immunol Methods.* 1982 53:187-94; Coulepis et al., *J Clin Microbiol.* 1985 22:119-24; White et al., *J Clin Microbiol.* 1989 27:2300-4; Liu et al., *J Immunol Methods.* 2000 234:P153-67; Tian et al., Bioconjug Chem. 2015 26:1144-55; Vira et al., *Anal Biochem.* 2010 402:146-50; Szabó et al., *Biophys J.* 2018 114:688-700; Hagan et al., *Lanthanide—Anal Bioanal Chem.* 2011 400:2847-64; Han et al. *Nat Protoc.* 2018 13:2121-2148; Bottrill et al., *Chem Soc Rev.* 2006 35:557-71; Ye et al., *J Clin Lab Anal.* 2014 28:335-40; Fernández Moreira et al., *Analyst.* 2010 135:42-52; Brouwers et al., J Nucl Med. 2004 45:327-37; Vera et al., *Nucl Med Biol.* 2012 39:3-13; Stein et al., *J Nucl Med.* 2001 42:967-74; Bratthauer G., *Methods Mol Biol.* 2010 588:257-70; Engle et al., *Science.* 2019 364:1156-1162; Sano et al., *Science.* 1992 258:120-2; Malou et al., *Trends Microbiol.* 2011 19:295-302; Cardoso et al., *Curr Med Chem.* 2012; 19:3103-27; East et al., *Methods Mol Biol.* 2014 1199:67-83; Tan et al., Nanomaterials (Basel). 2015 5:1297-1316; Geng et al., *Bioconjug Chem.* 2016 27:2287-2300; Pecanha et al., *J Immunol.* 1991 146:833-9; Pecanha et al., *J Immunol.* 1993 150:2160-8; and Chen Y., *Methods Mol Biol.* 2013 1045: 267-73, the disclosures of which are incorporated herein.

Figure 7A:
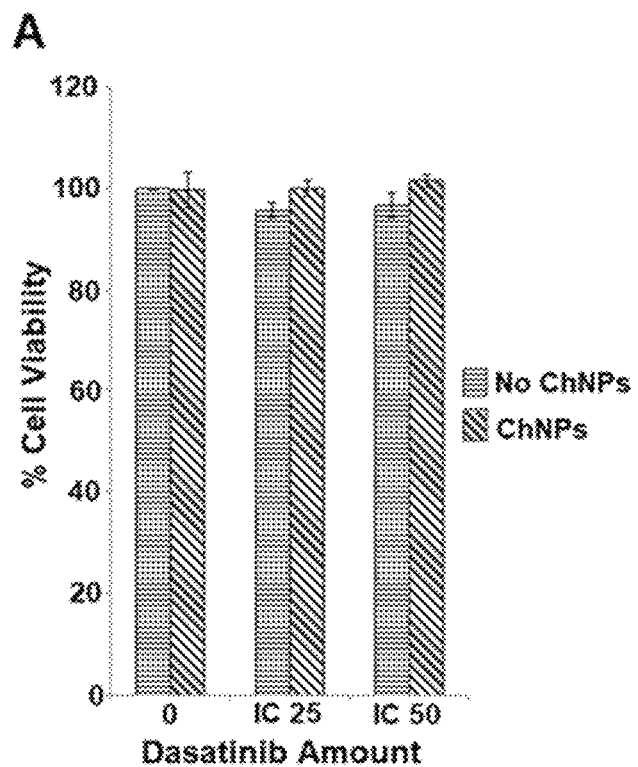
FIG. 7A-B provides for a FL5.12 (PH+) leukemia model that was treated with ChNPs and Dasatinib. Two FL5.12 cell lines were used: (A) 'healthy' FL5.12 wild type cells, and (B) 'diseased' FL5.12 cells that comprise a Bcr-Abl p190 translocation. The IC25 and IC50 amounts were determined through delivering dasatinib (tyrosine kinase inhibitor for leukemia) to the p190 cells and determining amounts of dasatinib that correlate with 25% of the cells being killed (IC25) or 50% of the cells being killed (IC50). These amounts of dasatinib were then delivered to each cell line along with 1e10 GCs/mL of BIM AAV/MCL-1 siRNA containing ChNPs. Viability was tested three days after delivery. The system was shown to be specific as (A) healthy cells had no cell death at the IC50 value of dasatinib for diseased cells, even when ChNPs co-delivered. (B) The diseased cells, however, showed a synergistic effect between the drug and ChNP combination. This synergistic effect was measured using a competitive index value (CI on the graph). CI values above 1 indicate synergy of two treatments, CI values of 1 denote an additive effect, and CI values below 1 denote an antagonistic effect between two treatments. (B) The values of 1.54 and 1.737 indicate that the dasatinib acted synergistically with the nanoparticles when treating leukemia.
Figure 7B:
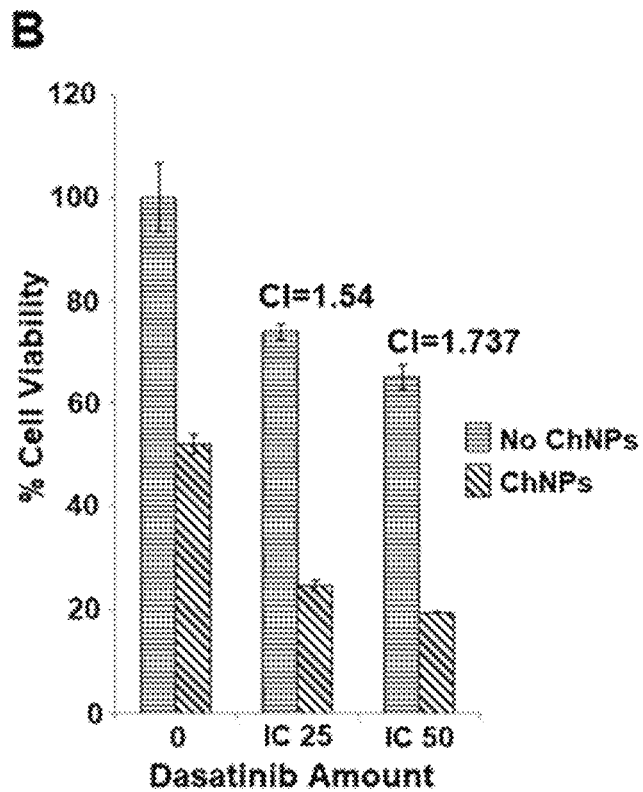
Figure 8A:
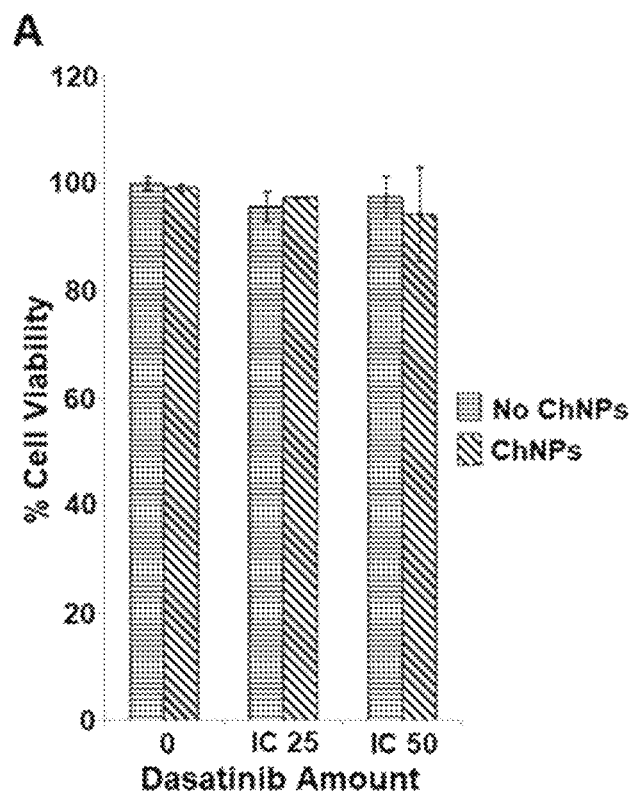
FIG. 8A-B provides for a BaF3 (PH+) leukemia model that was treated with ChNPs and Dasatinib. Two BaF3 cell lines were used: (A) 'healthy' BaF3 wild type cells, and (B) 'diseased' BaF3 cells that comprise a Bcr-Abl p210 translocation. The IC25 and IC50 amounts were determined through delivering dasatinib (tyrosine kinase inhibitor for leukemia) to the p210 cells and determining amounts of dasatinib that correlate with 25% of the cells being killed (IC25) or 50% of the cells were killed (IC50). These amounts of dasatinib were then delivered to each cell line along with 1e10 GCs/mL of BIM AAV/Mcl-1 siRNA containing ChNPs. Viability was tested three days after delivery. The system was shown to be specific as (A) healthy cells had no cell death at the IC50 value of dasatinib for diseased cells, even when ChNPs co-delivered. (B) The diseased cells, however, showed a synergistic effect between the drug and ChNP combination. This synergistic effect was measured using a competitive index value (CI on the graph). CI values above 1 indicate synergy of two treatments, CI values of 1 denote an additive effect, and CI values below 1 denote an antagonistic effect between two treatments. (B) The values of 1.523 and 2.135 indicate that the dasatinib acted synergistically with the ChNPs when treating leukemia.
Figure 8B:
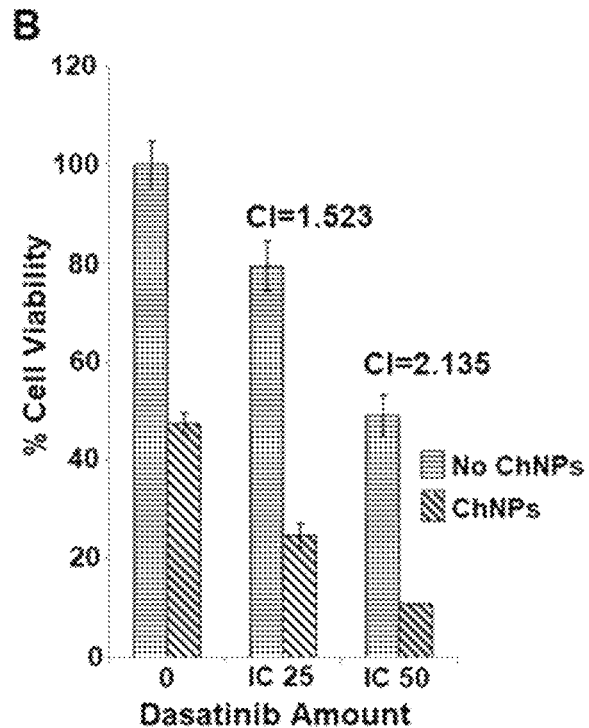
Figure 9:
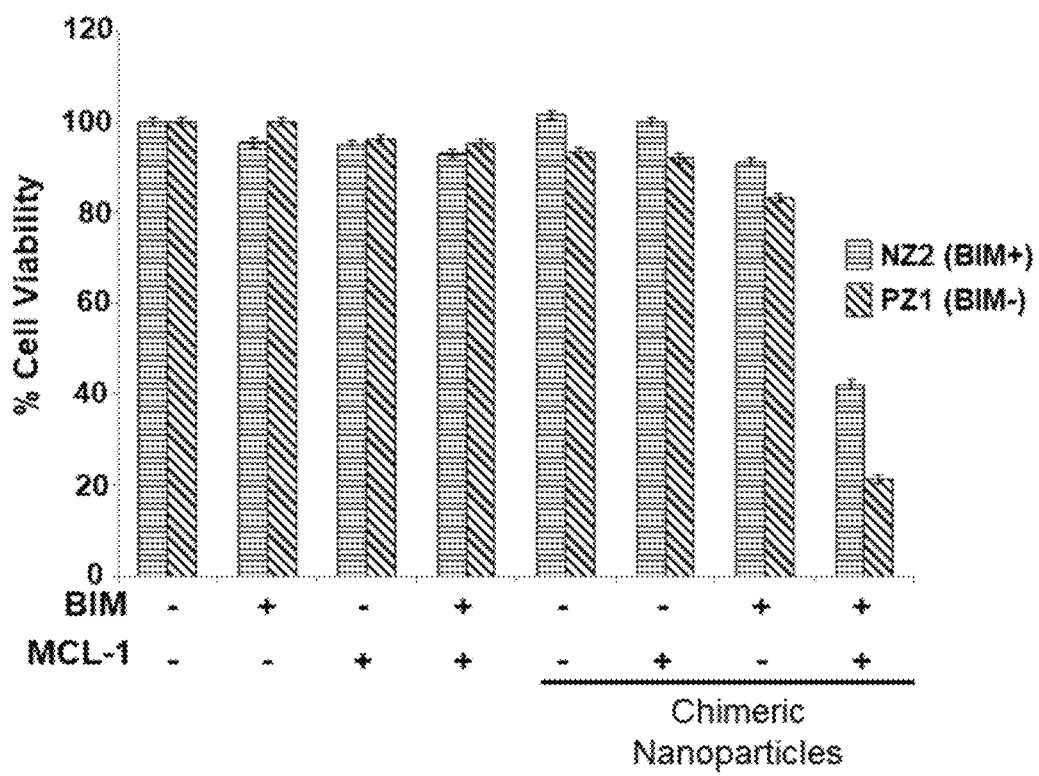
FIG. 9 provides for selective eradication of EGFR+ non-small cell lung cancer by BIM/MCL-1 ChNPs. Two different lines of non-small cell lung cancer were treated with various AAVs and ChNPs. The two lines are NZ2, a line that has high BIM expression, meaning it is less aggressive form of cancer. And PZ1, which has a BIM deletion, leading to a more aggressive cancer. Each group was delivered to the cells at a concentration of 1e10 GCs/mL or 0.75 ug siRNA/mL (depending on if they had AAV, siRNA, or both). Both lines were successfully treated by the ChNPs, with PZ1 having a more pronounced effect, likely due to it being void of BIM to begin with. Restoring BIM to these PZ1 cells caused more cell death as they likely conditioned or adapted to growing without the pro-apoptotic gene BIM.
Figure 10A:
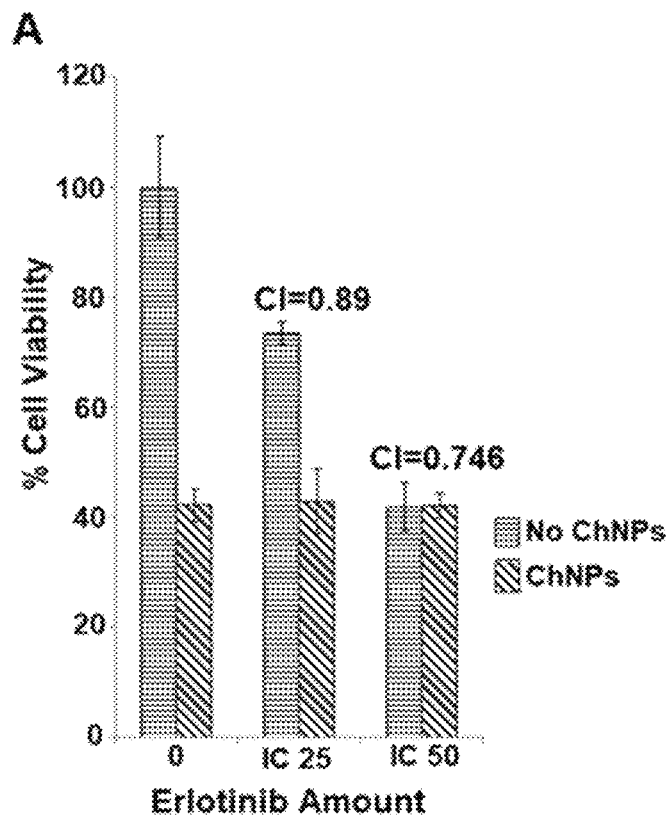
FIG. 10A-B provides for a non-small cell lung cancer (NSCLC) model that was treated with ChNPs and Erlotinib, a TKI for EGFR+ lung cancer). The cell lines used in this study are (A) NZ2, a BIM+ NSCLC; and (B) PZ1, a BIM-NSCLC. IC 25 and IC 50 values were determined in each cell line by finding the concertation of erlotinib that killed either 25% or 50% of the cells respectively. These found concentrations were then co-delivered to cells with 1e10 GCs/mL of ChNPs with BIM AAV and MCL-1 siRNA. The viability of the cells was determined 3 days after delivery. (A) The BIM high cancer NZ2 was shown to have an antagonistic effect between nanoparticles and erlotinib. This is not surprising as the high levels of BIM should respond well to chemotherapy, thus the additional BIM will likely not advance cancer treatment. (B) The BIM deleted line, PZ1, however, saw a synergistic effect between the erlotinib and ChNPs, with a CI value of 1.236 at the IC25 value of drug, and a CI value of 1.4 at the IC50 value of drug.
Figure 10B:
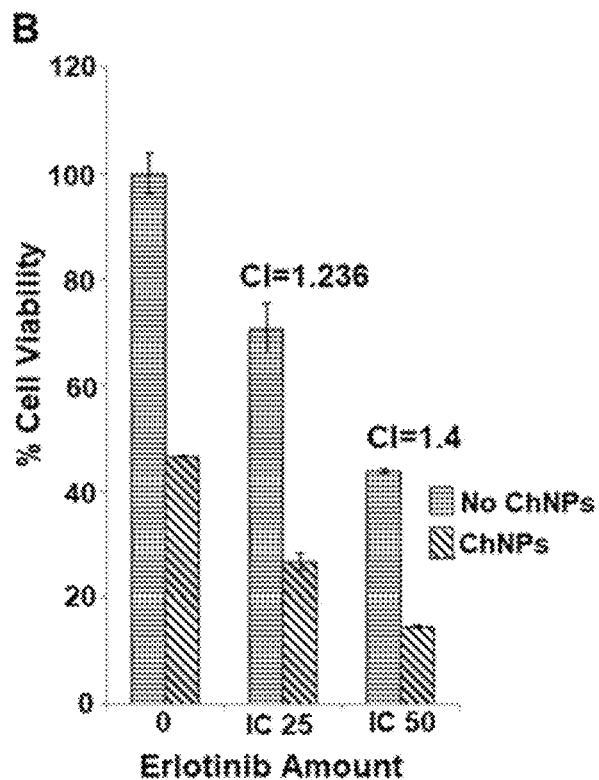
Figure 11A:
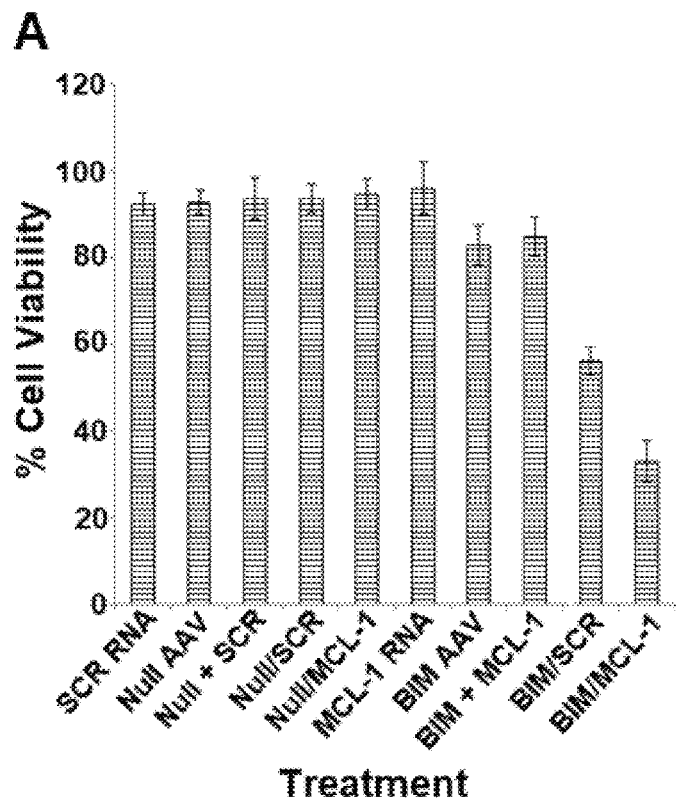
FIG. 11A-B provides for an ZR-75-30 (Her2+) Breast cancer model that was treated with ChNPs and Lapatinib. The cell line used in this study is ZR-75-30, which is a Her2+ breast cancer cell line. (A) ZR-75-30 cells were plated and treated with various groups of AAV, siRNA, AAV and siRNA, and ChNPs containing different AAV and siRNA in the ChNPs. Each was delivered at a concentration of 1e10 GCs/mL AAV, 0.75 ug/mL of siRNA, or both depending on what was being delivered. The BIM/MCL-1 combination outperformed all groups, with BIM/SCR ChNPs performing better than BIM AAV alone. (B) The combined effect of lapatinib (TKI to treat her2+ breast cancer) with BIM/MCL-1 ChNPs was tested in the ZR-75-
Figure 11B:
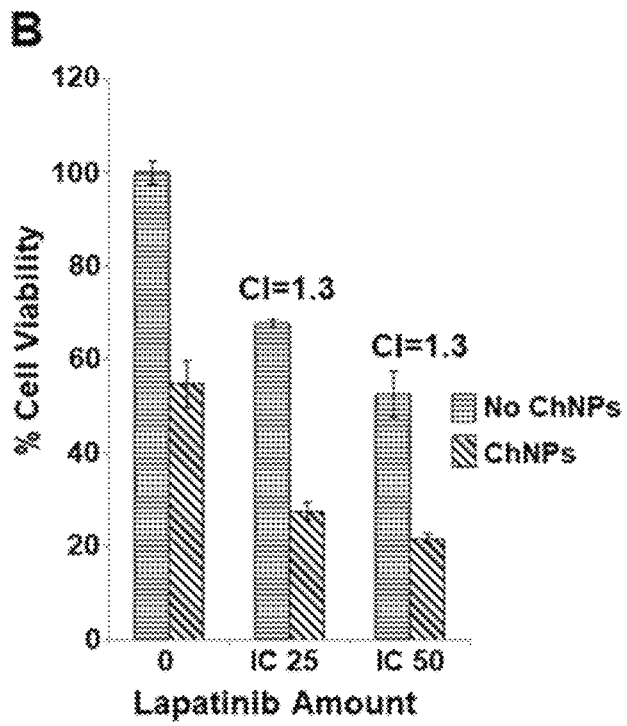

The multi-modal cancer therapies described herein comprise a gene carrier combining both viral and nonviral vectors into a single nanoparticle platform (chimeric nanoparticles [ChNPs]) for multi-delivery of a transgene and gene silencing or gene editing nucleic acids being used in combination with an anticancer agent (e.g., TKIs). It was found in the studies presented herein, that use of the ChNPs with various TKIs provided for a synergistic anticancer effect in cancers with different etiologies, such as leukemias, breast cancer, non-small cell lung cancers, and melanomas. In particular, it was found in a Ph+ Leukemia model, that use of the ChNPs with Dasatinib provided for a synergistic effect (CI>1) when FL5.12 p190 leukemia cells were treated with IC25 and IC50 concentrations of Dasatinib (e.g., see FIG. 7B). Similar synergistic results were seen when using the CHnPs with dasatinib in another Ph+ Leukemia model using BAF3 p210 leukemia cells (e.g., see FIG. 8B). When the ChNPs were used in an EGFR+ non-small cell lung cancer (NSCLC) model, ChNPs also worked synergistically with erlotinib in killing PZ1(BIM−) NSCLC cells, with CIs>1 for IC25 and IC50 concentrations of Erlotinib (e.g., see FIG. 10B). No similar synergistic effect was seen in NZ2 (Bim+) NSCLC, most likely due these cells responding well to chemotherapy with the higher levels of BIM (e.g., see FIG. 10A). In a Her2+ breast cancer model, ChNPs worked synergistically with lapatinib in killing Zr-75-30 Her2+ breast cancer cells, with CIs>1 for IC25 and IC50 concentrations of lapatinib (e.g., see FIG. 11B). In a triple negative breast cancer model, ChNPs worked even more synergistically with erlotinib in killing MDA-MB-468 triple negative breast cancer cells, with a CI>>1 for the IC25 concentration of erlotinib and a CI>1 for the IC50 concentration of erlotinib (e.g., see FIG. 12B). In an MPN model, however, the ChNPs worked merely additively or even antagonistically with ruxolitinib in killing BaF3 Jak2v617F MPN cells, with CIs<1 for IC25 and IC50 concentrations of ruxolitinib (e.g., see FIG. 14B). In a Braf+ melanoma model, ChNPs worked synergistically with PLX-4720 in killing A375 Braf+ breast cancer cells, with a CI>1 for the IC25 concentration of PLX-4720 and a CI>>>>>>1 for the IC50 concentration of PLX-4720 (e.g., see FIG. 15B). ChNPs also worked synergistically with PLX-4720 in killing Sk-Mel-28 Braf+ melanoma cells, with a CI>1 for the IC25 concentration of PLX-4720 and a CI>>>>>>1 for the IC50 concentration of PLX-4720 (e.g., see FIG. 16B). In a Kit+ melanoma model, the ChNPs also worked synergistically with dasatinib in killing WM3211 Kit+ cells, with a CI>1 for the IC25 concentration of dasatinib and a CI>>>>1 for the IC50 concentration of dasatinib (e.g., see FIG. 17B). Finally, in a Nras+ melanoma model, ChNPs worked synergistically with PD98059 in killing Sk-Mel-2 Nras+ melanoma cells, with CIs>1 for IC25 and IC50 concentrations of PD98059 (e.g., see FIG. 18B). The foregoing results clearly indicate that ChNPs of the disclosure worked synergistically with a variety of anticancer agents in treating different types of cancers.

The ChNPs described herein incorporate the advantages of a viral vector's high transduction efficiency in its core as well as nonviral vectors controlled cytosolic release of gene silencing or gene editing nucleic acids and low immunogenicity in its polymeric shell, toward achieving efficient, controlled, and targeted co-delivery of the transgene and gene silencing or gene editing nucleic acids. In a particular embodiment, the ChNPs have been specifically designed to administer a transgene and the gene silencing/editing agent that works in tandem, and in some cases, synergistically with an anti-cancer agent to provide a multimodal therapy that is more effective in treating a cancer than use of the anticancer agent alone or use of the ChNPs alone. Examples, of anticancer agents that can be used with the ChNPs disclosed herein include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammaII and calicheamicin omegaII; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included anticancer agents are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; antibodies such as trastuzumab and pharmaceutically acceptable salts, acids or derivatives of any of the above. In a particular embodiment, the disclosure provides for combined therapy comprising one or more ChNPs disclosed herein used in combination with a tyrosine kinase inhibitor (TKI). Examples of protein kinase inhibitors, include but are not limited to, adavosertib, afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, and vemurafenib. In another embodiment, the disclosure provides for combined therapy comprising one or more ChNPs disclosed herein used in combination with an angiogenesis inhibitor. Examples of angiogenesis inhibitors, include but are not limited to, axitinib, bevacizumab, cabozantinib, everolimus, lenalidomide, lenvatinib mesylate, pazopanib, ramucirumab, regorafenib, sorafenib, sunitinib, thalidomide, vandetanib, and Ziv-aflibercept. In another embodiment, the disclosure provides for combined therapy comprising one or more ChNPs disclosed herein used in combination with a PARP inhibitor. Examples of PARP inhibitors, include but are not limited to, olaparib, niraparib, rucaparib, and talzoparib. The anticancer agent may be administered, by a route and in an amount commonly used therefore, simultaneously (at the same time or in the same formulation) or sequentially with a ChNP as disclosed herein. When a ChNP as disclosed herein is used contemporaneously with one or more anticancer agents, a pharmaceutical composition containing the one or more anticancer agents in addition to a ChNP disclosed herein may be utilized but is not required. Accordingly, the pharmaceutical compositions disclosed herein include those that also contain one or more anticancer agents in addition to a ChNP disclosed herein.

The multimodal cancer therapies disclosed herein can be administered to any host, including a human or non-human animal, in an amount effective to inhibit the growth of a cancer or result in the death of cancer cells. Thus, the methods and compositions are an improvement over a single modal cancer therapy, by targeting a cancer using different and effective modalities, such as the combined use of gene therapy, gene silencing/editing nucleic acids, and anticancer agents.

Any of a variety of art-known methods can be used to administer a ChNP disclosed herein with one or more additional anticancer agents. For example, administration can be parenterally, by injection or by gradual infusion over time. The ChNPs alone or with the anticancer agent can be administered intravenously, intraperitoneally, intramuscularly, subcutaneously, intracavity, by inhalation, or transdermally.

Preparations for parenteral administration of a composition comprising a ChNP of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

The disclosure provides methods for treating a subject with a cancer or suspected of having a cancer comprising administering a multimodal cancer therapy comprising a therapeutically effective amount of one or more ChNPs and one or more anticancer agents disclosed herein. A therapeutically effective amount can be measured as the amount sufficient to prevent cancer cells from dividing and growing, ultimately killing the cancer cells. Generally, the optimal dosage of ChNPs and/or the anticancer agents will depend upon the type and stage of the cancer and factors such as the weight, sex, and condition of the subject. Nonetheless, suitable dosages can readily be determined by one skilled in the art. Typically, dosages used in vitro may provide useful guidance in the amounts useful for in situ administration of the pharmaceutical composition, and animal models may be used to determine effective dosages for treatment of specific infections. Various considerations are described, e.g., in Langer, Science, 249: 1527, (1990); Gilman et al. (eds.) (1990), each of which is herein incorporated by reference. Typically, a suitable dosage for the ChNPs is 1 to 1000 mg/kg body weight, e.g., 10 to 500 mg/kg body weight. In a particular embodiment, a ChNP disclosed herein is administered at dosage of 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 210 mg/kg, 220 mg/kg, 230 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 100 mg/kg, or a range that includes or is between any two of the foregoing dosages, including fractional dosages thereof.

A pharmaceutical composition comprising a ChNP and/or an anticancer agent of the disclosure can be in a form suitable for administration to a subject using carriers, excipients, and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The disclosure further provides for a pharmaceutical composition comprising a ChNP and/or an anticancer agent disclosed herein that can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

Cancers in many instances become resistant to chemotherapeutic treatments, ultimately limiting their usefulness. By co-delivering an anticancer agent with the ChNPs disclosed herein, you can attack cancer at a molecular level. Accordingly, the multi-modal cancer therapies described herein will increase the effectiveness of the anticancer agent by combining the anticancer agent with a ChNP disclosed herein. Further, the multi-modal cancer therapies described herein will allow for lower dosing of the anticancer agent, making the treatment safer.

Accordingly, the disclosure provides a method for inhibiting a cancer and/or a neoplastic disorder by contacting or administering a multimodal cancer therapy of the disclosure that comprises a therapeutically effective amount of a ChNP disclosed herein with one or more anticancer agents to a subject who has a cancer or is at risk of having a cancer. The term "inhibiting" means preventing or ameliorating a sign or symptoms of a cancer and/or a neoplastic disorder (e.g., tumor growth, cancer cell proliferation and/or migration, cancer cell metastasis, and the like).

The disclosure also provides a method for inhibiting the growth of a tumor or cancer by contacting the tumor cells, cancer cells or neoplastic cells with a with an inhibiting effective amount of a multimodal cancer therapy disclosed herein. The term "contacting" refers to exposing the cells (e.g., tumor, cancer or neoplastic cell) to an agent. Contacting can occur in vivo, for example, by administering a ChNP of the disclosure to a subject afflicted with a tumor, cancer or neoplasm. In vivo contacting includes both parenteral as well as topical. "Inhibiting" or "inhibiting effective amount" refers to the amount of a multimodal cancer therapy disclosed herein that is sufficient to cause, for example, tumor, cancer or neoplastic cell death, inhibition of growth and/or migration and/or inhibition of prevention of metastasis.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more ChNPs described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound disclosed herein with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Materials.

GFP-encoding AAVs (GFP$^{AAV}$; serotype 2) and luciferase-encoding AAVs (Luc$^{AAV}$; serotype 2) are purchased from Vector Biolabs (Philadelphia, Pa.) and ViroVek (Hayward, Calif.), respectively. BIM-encoding AAV vectors are prepared by Vector Biolabs using BIM (isoform L) plasmid. MCL-1 siRNA, siRNA with scrambled sequences, and primers for MCL-1 mRNA are obtained from Qiagen (Venlo, Netherlands). Eosin-5-isothiocyanate, Alexa Fluor 488 carboxylic acid succinimidyl ester, and Quant-iT PicoGreen nucleic acid assay kit are purchased from Invitrogen (Carlsbad, Calif.). N-Hydroxysuccinimide (NHS) and N,N-diisopropylethylamine (DIPEA) are purchased from Acros Organics (Thermo Fisher Scientific, Pittsburgh, Pa.), and 1-ethyl-3-(3-dimethylaminopropyl) carbodiimide (EDC) is purchased from Advanced ChemTech (Louisville, Ky.). (NHS)-functionalized polyethylene glycol (NHS-PEG, 5 kDA) are purchased from Creative PEG Works Inc. (Winston Salem, N.C., U.S.A.). PD10 size-exclusion column (MWCO 5 kDa) is purchased from GE Healthcare (Pittsburgh, Pa.) and Amicon Ultra Centrifugal filters (MWCO 100 kDa) are purchased from Millipore (Billerica, Mass.). QuickTiter AAV quantitation kit is purchased from Cell Biolabs (San Diego, Calif.). 3-(4,5-dimethyl-2-thiazolyl)-2, 5-diphenyltetrazolium bromide (MTT) is purchased from Sigma Aldrich (St. Louis, Mo.) and nucleus-staining dye DRAQS is purchased from BioStatus (Leicestershire, UK). Forward and reverse primers for GFP gene are purchased from Invitrogen (Carlsbad, Calif.). TaqMan Fast Universal PCR Mater Mix is purchased from Applied Biosystems (Carlsbad, Calif.). Steady-Glo-luciferase assay solution (Promega, Madison, Wis.) and BCA protein assay kit (Pierce, Rockford, Ill.) are used to quantify Luc expression and total protein amounts, respectively. Anti-AAV polyclonal antibodies are purchased from IMGENEX (San Diego, Calif.). siRNA against firefly luciferase (Luc$^{siRNA}$) and Dye547-labeled siRNA (Dye547-siRNA) are purchased from Ambion (Foster City, Calif.). Acid-degradable amino ketal methacrylamide monomer and acid-degradable ketal bismethacrylamide cross-linker are synthesized as reported below, with slight modifications. Non-degradable cationic monomer and cross-linker, which contain an additional ethoxy group instead of ketal linkage, were also synthesized as reported below. Sialic acid is purchased from Nacalai USA (San Diego, Calif.). Human chronic myelogenous leukemia K562 cells were purchased from ATCC (Manassas, Va., U.S.A). Murine pro-B-cell lymphoid FL5.12 cells and FL5.12/p190 cells are transduced to express firefly luciferase by lentiviral vectors purchased from Capital Bioscience (Gaithersberg, Md., U.S.A).

Cell Culture.

K562 cells and luciferase-expressing K562 cells (K562/Luc cells) are cultured in Iscove's modified Dulbecco's medium (MediaTech, Herdon, Va., U.S.A.) supplemented with 10% fetal bovine serum (FBS) (Hyclone, Logan, Utah, U.S.A.) and 1% antibiotics (MediaTech, Herdon, Va., U.S.A.). FL5.12/p190 and luciferase-expressing FL5.12/p190 cells (FL5.12/p190/Luc cells) are grown in RPMI 1640 containing 10% FBS and 1% antibiotics. FL5.12 cells are cultured in the same media supplemented with 5 ng/mL IL-3. All cells were cultured at 37° C. with 5% $CO_2$ and 100% humidity.

Preparation of BIM-Expressing, MCL-1 Silencing Chimeric Nanoparticles (BIM/MCL-1 ChNPs).

BIM/MCL-1 ChNPs are synthesized as described in Hong et al. (ACS Nano 10:8705-8714 (2016)). Briefly, BIM-encoding AAV vectors ($1.0 \times 10^{11}$ genome copy [GC]) in 5 mL of 10 mM sodium bicarbonate buffer (pH 8.0) are reacted with 2 mg of eosin-5-isothiocyanates in 10 µL of dimethyl sulfoxide (DMSO) with mild agitation. After 3 h incubation at RT, the residual eosin-5-isothiocyanates are removed using a PD mini size-exclusion column. The eosin-conjugated AAV vectors ($6.0 \times 10^{10}$ GC) are suspended in 1 mL of 10 mM HEPES buffer (pH 7.4) containing 10 mg of ascorbic acids. Ten mg of amino ketal methacrylamide monomers and 3.0 µg of siRNA are premixed in 50 µL of 10 mM HEPES buffer for 30 min at RT. The resulting monomers/siRNA solution is then added to eosin-conjugated AAV solution, followed by photopolymerization with mild stirring under a halogen lamp at 700 klux. After 10 min, 10 mg of amino ketal methacrylamide monomers and 4 mg of ketal bismethacrylamide cross-linkers are added and further polymerized for another 5 min. Ascorbic acids, unreacted monomers, and cross-linkers are removed by centrifugal filtration (100 kDa MWCO) of the resulting solution at 3000 rpm for 30 min at 4° C. For the in vivo study, ChNPs in 1 mL of 10 mM HEPES buffer are incubated with 0.5 mg of NHS-PEG (5 kDa) in 20 µL of DMSO for 4 h at 4° C. Unreacted NHS-PEG is removed using centrifugal filtrations (100 kDa MWCO) at 3000 rpm for 30 min at 4° C.

Sialic Acid (SA)-Conjugation to ChNPs for Targeted Gene Delivery.

In order to activate its carboxylic acid group, sialic acid (SA) (19.4 mg in 100 µL of 10 mM sodium bicarbonate buffer) is reacted with 24 mg of EDC and 14.5 mg of NHS for 15 min at room temperature. To ChNPs ($2\times10^{11}$ GFP$^{AAV}$) in 1 mL of 100 mM sodium bicarbonate buffer, 10 µL of DIPEA is added and the activated SA solution is added. After the resulting mixture is mildly agitated overnight at 4° C., SA-ChNPs are purified twice by centrifugal filtration (MWCO 10 kDa) at 3500 rpm (2100×g) at 4° C. for 30 min.

CD22+ DLBCL-Val/Luc and CD22− SUP-B15 cells are plated at a density of $2.0\times10^4$ cells/well in a 24-well. ChNPs and SA-ChNPs ($5\times10^9$ GC; prepared with AF488-conjugated Luc' particles and Dye547-siRNA) in 100 µL PBS are added to the cell-containing wells in a final volume of 500 µL/well. At different periods of incubation, the cells are spun down and washed twice with PBS. Average fluorescence intensity of the cells was determined by flow cytometry and used to quantify a relative amount of internalized ChNPs. Uptake of ChNPs by DLBCL-Val/Luc cells are normalized to SUP-B15 cells in order to evaluate the receptor-mediated, targeted cellular uptake of SA-ChNPs. Transduction of DLBCL-Val/Luc and SUP-B15 cells by free GFP$^{AAV}$, GFP$^{AAV}$/Luc$^{siRNA}$ ChNPs, and SA-conjugated GFP$^{AAV}$/Luc$^{siRNA}$ ChNPs is determined by measuring GFP expression as described below. The cells are also incubated with ChNPs and SA-ChNPs in the presence of free Sat various concentrations. Using flow cytometry, inference of transduction by free SA is determined by measuring reduced GFP expression.

Characterization of BIM/MCL-1 ChNPs.

The hydrodynamic size and the zeta potential of BIM/MCL-1 ChNPs ($0.8\times10^{10}$ GC AAV/mL in deionized water) are measured using a Malvern Zetasizer Nano ZS (Malvern Instruments, Westborough, Mass.). BIM/MCL-1 ChNPs ($0.3\times10^{10}$ GC AAV in 5 uL of deionized water) are spotted on a carbon-coated grid (Ted Pella, Redding, Calif.) and dried in a vacuum chamber for 2 h at room temperature. The grid is further stained with 1% uranyl acetate, dried in a vacuum chamber for 4 h, and observed under a Philips CM20 TEM (Philips Electronic Instruments, Mahwah, N.J.) at 80 kV. The concentrations of siRNA and AAV encapsulated in BIM/MCL-1 ChNPs are determined as described above. Briefly, BIM/MCL-1 ChNPs in 100 mM acetate buffer (pH 5.0) are incubated for 4 h at 37° C. with mild stirring, followed by centrifugation at 3000 rpm for 10 min using an Amicon Ultra centrifugal filter (MWCO 100 kDa; EMD Millipore, Darmstadt, Germany). The eluted free siRNA is quantified using a Quant-iT RiboGreen RNA Assay Kit (Invitrogen, Carlsbad, Calif.). The amount of BIM AAV released from acid-hydrolyzed BIM/MCL-1 ChNPs is quantified using a QuickTiter AAV Quantitation Kit (Cell Biolabs, San Diego, Calif.).

Cell Proliferation/Apoptosis and Viability Assays.

K562 cells ($5.0\times10^4$ cells/well) are seeded in a 24-well plate. After 24 h, the cells are incubated with PBS, BIM AAV alone, MCL-1 siRNA alone, mixture of BIM AAV and MCL-1 siRNA, and various ChNPs (Null/Scr, Null/MCL-1, BIM/Scr, BIM/MCL-1 ChNPs) at $1.0\times10^{10}$ GC AAV/mL and 125 nM siRNA. After 24 h, the medium is replaced with AAV- and siRNA-free media, and the cells are further maintained by replacing the old media with fresh media on a daily basis. The cells are counted by flow cytometry (Guava Technologies, Hayward, Calif., U.S.A.) after stained by Alexa Fluor 488 annexin V/Dead Cell Apoptosis Kit (Invitrogen, Carlsbad, Calif., U.S.A.) according to manufacturer's recommendation. The proliferation/apoptosis of BCR-ABL-negative FL5.12 cells and BCR-ABL-positive FL5.12/p190 cells are also carried out as described above.

Figure 3A:
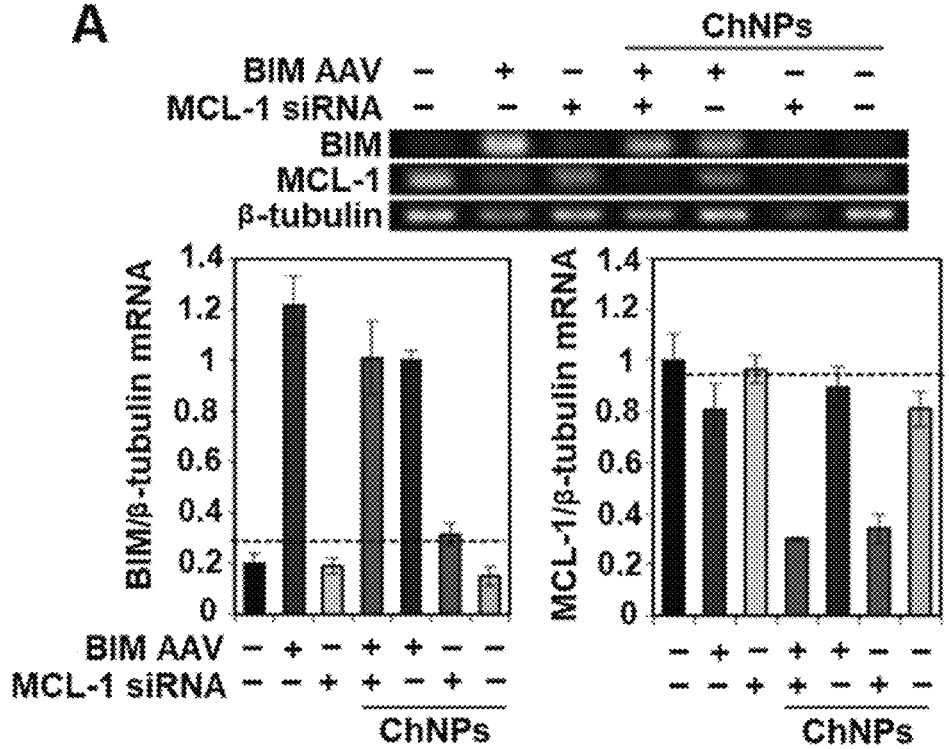
FIG. 3A-B demonstrates the synergistically induced apoptosis of BCR-ABL$^+$ human chronic myelogenous leukemia (CML) K562 cells in vitro and in vivo via simultaneous BIM expression and MCL-1 silencing by the ChNPs. Cell lysates were collected 3 days after K562 cells were treated with PBS, BIM AAV alone, MCL-1 siRNA alone, BIM/MCL-1 ChNPs, BIM/Scr ChNPs, Null/MCL-1 ChNPs, or Null/Scr ChNPs. Scr indicates that the siRNA has a scrambled sequence, while Null indicates that AAV does not encode a transgene, respectively. Consistent doses of 1.0× $10^{10}$ genome copies (GC) of BIM AAV/mL and 125 nM MCL-1 siRNA were used in the experiments, and 10% serum was used for the entire experimental period. The relative levels of BIM and MCL-1 mRNA and proteins were quantified by densitometry analysis and further normalized by β-tubulin mRNA and protein levels, respectively. Restored BIM expression and the simultaneous silencing of MCL-1 expression in K562 cells at both the mRNA and protein levels were confirmed by (A) RT-PCR and (B) Western blot. The dotted line indicates the averaged background mRNA and protein levels (e.g., BIM mRNA and protein levels in the cells incubated with PBS, MCL-1 siRNA alone, Null/MCL-1 ChNPs, and Null/Scr ChNPs; MCL-1 mRNA and protein levels in the cells incubated with PBS, BIM AAV alone, BIM/Scr ChNPs, or Null/Scr ChNPs).
Figure 3B:
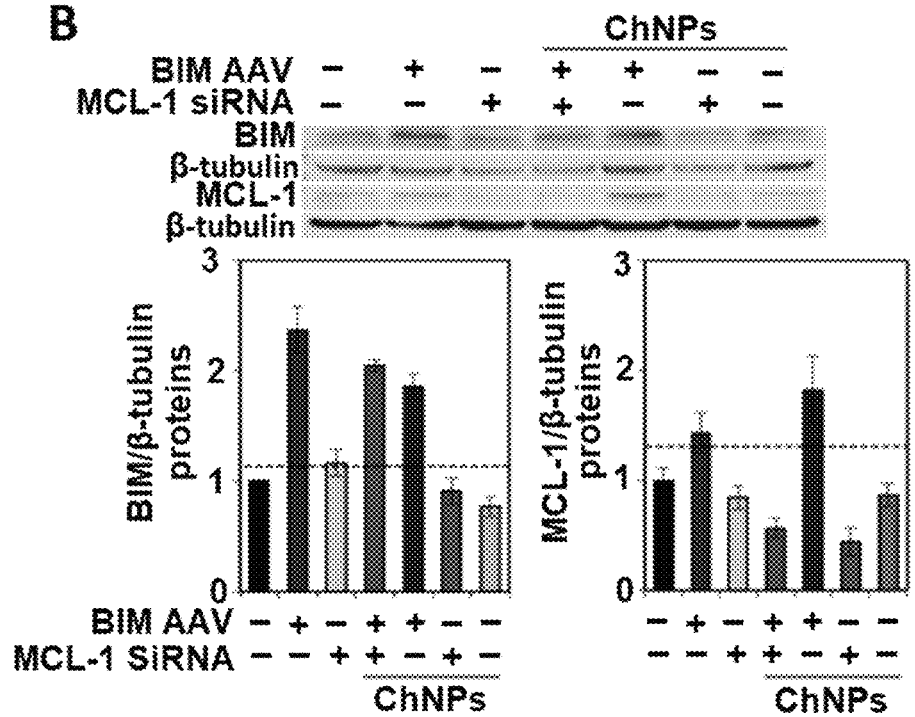

FL5.12 and FL5.12/p190 cells are seeded in a 48-well plate at a density of $2.0\times10^4$ cells/well with/without IL-3 (5 ng/mL). After 24 h, PBS, BIM AAV alone, MCL-1 siRNA alone, mixture of BIM AAV and siRNA, and various ChNPs (Null/Scr, Null/MCL-1, BIM/Scr, BIM/MCL-1 ChNPs) are added to the cells at different BIM AAV and MCL-1 siRNA concentrations. To measure cell viability, the cells maintained with fresh media everyday are pelleted by centrifugation (2000 rpm, 5 min, 4° C.) and resuspended in fresh media. The cells in 90 µL medium then are transferred into a 96-well plate where MTT (5 mg/mL in 10 µL PBS) is subsequently added. After 4 h of incubation at 37° C., the well plate is centrifuged at 2000 rpm and 4° C. for 5 min, and the media is replaced by 100 µL DMSO per well. The relative cell viability is quantified by comparing absorptions at 570 nm using a microplate reader (Synergy H1, Biotek), based on the absorption in the wells containing nontreated cells. Cancer cells (such as those listed in Table 1) are incubated with BIM/MCL-1 ChNPs ($1\times10^9$-$1\times10^{10}$ AAV GC/mL and 12.5-125 µM siRNA) and corresponding chemotherapeutic (0.1 nM-1 µM) at varying ratios (See FIG. 3). The cell viability and apoptosis assays are same as indicated above, but with minor changes.

Western Blot.

K562 cells are seeded on a 6-well plate ($3.0\times10^6$ cells per a well) for 24 h before being incubated with PBS, BIM AAV alone, MCL-1 siRNA alone, and various ChNPs (Null/Scr, Null/MCL-1, BIM/Scr, and BIM/MCL-1 ChNPs) at concentrations of $1.0\times10^{10}$ GC BIM AAV and 125 nM MCL-1 siRNA. After 3 days, the cells are collected by centrifugation (2000 rpm, 5 min, 4° C.) and lysed in IP buffer (Pierce, Rockford, Ill., U.S.A.). The protein concentration in cell lysates are measured and normalized by β-tubulin ELISA (MyBioSource, San Diego, Calif., U.S.A.), following the manufacturer's protocol. Equal amounts of protein are loaded and separated in 12% Mini-PROTEAN TGX Precast gel (Bio-Rad, Hercules, Calif., U.S.A.) for 1 h at 200 V, followed by being transferred to a nitrocellulose membrane (Bio-Rad, Hercules, Calif., U.S.A.). The membrane is then blocked with 5% milk in TBST buffer (10 mM Tris-HCl at pH 7.5, 150 mM NaCl, and 0.05% Tween 20) for 1 h at RT with gentle shaking and washed three times with TBST buffer. Rabbit IgG against BIM, MCL-1, and β-tubulin primary antibodies (Cell Signaling Technology, Beverly, Mass., U.S.A.) are added to the membrane in TBST buffer and incubated overnight at 4° C., followed by rinsing three times with TBST. Then, horseradish peroxidase conjugated antirabbit IgG secondary antibodies (Promega, Madison, Wis., U.S.A.) are added and incubated overnight at 4° C. After the membrane is rinsed three times with TBST, the protein bands are visualized using enhanced chemiluminescence detection Kit (Bio-Rad, Hercules, Calif., U.S.A.) according to the manufacturers' instructions. The chemiluminescence signals were visualized and analyzed using a UV transilluminator and its software (Alpha Innotech, Santa Clara, Calif., U.S.A.).

Reverse Transcriptase-Polymerase Chain Reaction (RT-PCR).

Entire RNA in K562 cells, which are incubated with AAV, siRNA, and ChNPs as in the Western blot above, are isolated using NucleoSpin RNA II kit (Macherey-Nagel, Duren, Germany) and reversely transcribed to cDNA using the reverse transcription system kit (Promega, Madison, Wis., U.S.A.) according to the manufacturers' protocol. RT-PCR is performed using an ABI 7900HT fast real-time PCR system (Applied Biosystems, Carlsbad, Calif., U.S.A.) in a 384-well plate. The RT-PCR is carried out at 50° C. for 30 min, 95° C. for 10 min, and 40 cycles at 95° C. for 15 s and 60° C. for 1 min. The resulting samples are electrophoresed in a 1% agarose gel containing 1 μg/mL ethidium bromide (EtBr) in TBE buffer at 110 V for 30 min. The bands are visualized and quantitatively compared using a UV transilluminator and its software (Alpha Innotech, Santa Clara, Calif., U.S.A.).

In Vivo Bioluminescence Imaging.

In an immunocompetent syngeneic model, 6-7 weeks-old Balb/c female mice are intravenously injected with BCR-ABL-positive FL5.12/p190/Luc cells ($1.0 \times 10^5$ cells per mouse) in the tail vein. After 1 week, the mice are intravenously injected with PBS, BIM AAV alone, MCL-1 siRNA alone, mixture of BIM AAV and MCL-1 siRNA, and various ChNPs (Null/MCL-1, BIM/Scr, and BIM/MCL-1 ChNPs) at doses of $5.0 \times 10^{11}$ GC AAV and 25 μg siRNA per mouse (see FIG. 5). The expansions of K562/Luc and FL5.12/p190/Luc cells are visualized by imaging mice intraperitoneally (IP) injected with 2 mg of synthetic firefly luciferin in 100 μL PBS (Promega, Madison, Wis., U.S.A.) using an IVIS Lumina system (Caliper Life Sciences, Hopkinton, Mass., U.S.A.) for 5 min. Bioluminescence signal intensities in mice are quantified using Living Image 3.2 software associated with the imaging system.

Statistical Analysis.

All triplicate experimental data collected from independently repeated measurements are represented as mean±standard deviation. Statistical analysis is performed with Student's t Test and statistical significance is at p-values lower than 0.05. Kaplan-Meier survival curve is analyzed using MedCalc statistical software.

Coadministration of BIM/MCL-1 ChNPs with Dastinib Provided a Synergistic Cancer Killing Effect In Vitro.

Figure 4:
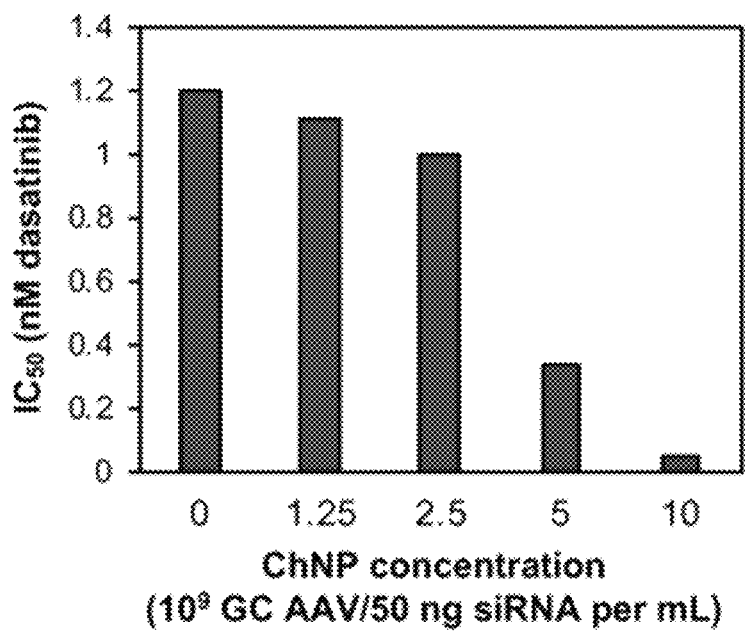
FIG. 4 presents the synergistic eradication of BCR-ABL$^+$ FL 5.12 p190 cells using a combined treatment of BIM/MCL-1 ChNPs and dasatinib. The cells were incubated with varying concentrations of BIM/MCL-1 ChNPs and dasatinib for 24 h. The cytotoxicity was measured at 3 days of post-treatment.

It was found that co-adiminstration of BIM/MCL-1 ChNPs with dastinib, a tyrosine kinase inhibitor (TKI), significantly reduced $IC_{50}$ values of dasatinib against BCR-ABL, in a concentration dependent manner (e.g., see FIG. 4). For example, BIM/MCL-1 ChNPs at a concentration of $1 \times 10^{10}$ GC AAV/0.5 μg MCL-1 siRNA per mL decreased $IC_{50}$ of dasatinib about 22 times, compared with an $IC_{50}$ of 1 nM without ChNPs. When BCR-ABL-FL5.12 cells were treated under the same conditions, about 100% cell viability was observed even at the highest concentrations of both BIM/MCL-1 ChNPs and dasatinib (data not shown). The result indicates that: (1) simultaneous BIM expression and MCL-1 silencing by BIM/MCL-1 ChNPs, and (2) synergistic eradication of BCR-ABL+ cells treated with BIM/MCL-1 ChNPs and a chemotherapeutic.

Figure 6:
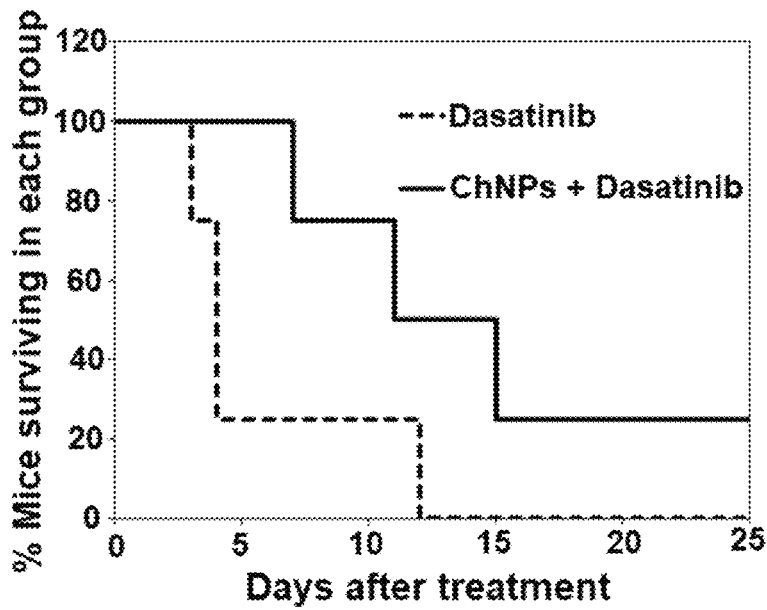
FIG. 6 demonstrates the results of an in vivo leukemia mice model. Mice were injected with Bcr-Abl p210$^+$ cells to develop leukemia and then were treated with dasatinib alone or with a combined therapy of dasatinib and BIM/MCL-1 ChNPs. As the data clearly indicates, the combined therapy of dasatinib and BIM/MCL-1 ChNPs provided improved anti-leukemic effects in the mouse model than dasatinib alone, even possibly at a late stage of the disease.

Coadministration of BIM/MCL-1 ChNPs with dastinib provided a greater antileukemic effect in vivo than administration of dastinib alone. It was found that co-administration of BIM/MCL-1 ChNPs with dastinib exhibited a greatly improved antileukemia effect in a leukemia mouse model (e.g., see FIG. 6). In particular, mice were injected with Bcr-Abl p210+ cells to develop leukemia and then were treated with dasatinib alone or with a combined therapy of dasatinib and BIM/MCL-1 ChNPs. As shown in FIG. 6, mice that were treated with the multimodal therapy of BIM/MCL-1 ChNPs with dastinib had much higher survival rates than those mice with dastinib alone. By the end of day 12, all mice treated with dastinib alone had died, while 50% of the mice treated with the multimodal therapy of BIM/MCL-1 ChNPs with dastinib were still alive; and by the end of day 25, 25% of the mice treated with the multimodal therapy were still alive. The overall high mortality rate is largely attributed to the leukemia being at an advanced stage prior to treatment. The data indicates that leukemia even at a late stage can benefit from the administration of the multimodal therapy of BIM/MCL-1 ChNPs with dastinib over use of dastinib alone.

It will be understood that various modifications may be made without departing from the spirit and scope of this disclosure. Accordingly, other embodiments are within the scope of the following claims.

What is claimed is:

1. A multimodal cancer therapy for treating a subject having a cancer, comprising:
   co-administering to the subject in need thereof a therapeutically effective amount of one or more tyrosine kinase inhibitors and one or more chimeric viral/non-viral nanoparticles (ChNPs), wherein the ChNPs comprise:
   (i) a core comprising a recombinant adeno-associated virus (AAV) that expresses a transgene which encodes BCL2L11 (BIM); and
   (ii) one or more acid labile degradable polymer layers surrounding the core, wherein the acid labile degradable polymer layers comprise encapsulated gene silencing/editing nucleic acids that suppress or inhibit the expression of MCL-1, wherein the acid degradable polymer layers hydrolyze in a mildly acidic environment having a pH from 4.5 to 6.8.

2. The multimodal cancer therapy of claim 1, wherein the cancer is selected from the group consisting of: adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

3. The multimodal cancer therapy of claim 2, wherein the cancer is selected from the group consisting of a chronic myelogenous leukemia (CML), acute lymphoblastic leukemia (ALL), non-small cell lung cancer (NSCLC), breast cancer, melanoma, colorectal cancer, and ovarian cancer.

4. The multimodal cancer therapy of claim 1, wherein the gene silencing/editing nucleic acids are siRNA, shRNA or miRNA.

5. The multimodal cancer therapy of claim 1, wherein the tyrosine kinase inhibitors are selected from the group consisting of adavosertib, afatinib, axitinib, binimetinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, neratinib, nilotinib, pazopanib, pegaptanib, ruxolitinib, sorafenib, sunitinib, trametinib, sU6656, PLX4720, PD98059, vandetanib, and vemurafenib.

6. The multimodal cancer therapy of claim 1, wherein the surface of the ChNPs have been modified to comprise a targeting moiety that targets the ChNPS to a certain cell type, a certain tissue type, a certain organ or a tumor.

7. The multimodal cancer therapy of claim 1, wherein the surface of the ChNPs have been modified to comprise a ligand that binds to a tumor-specific antigen.

8. The multimodal cancer therapy of claim 7, wherein the ligand is an antibody or a scFv.

9. The multimodal cancer therapy of claim 7, wherein the tumor-specific antigen is selected from alphafetoprotein (AFP), carcinoembryonic antigen (CEA), CA-125, CA15-3, CA19-9, MUC-1, epithelial tumor antigen (ETA), tyrosinase, melanoma-associated antigen (MAGE), abnormal products of ras or p53, CTAG1B, MAGEA1, and HER2/neu.

10. The multimodal cancer therapy of claim 1, wherein the one or more ChNPs are parenterally administered.

11. The multimodal cancer therapy of claim 1, wherein the one or more tyrosine kinase inhibitors are parenterally, and/or orally administered.

12. The multimodal cancer therapy of claim 1, wherein the one or more ChNPs are concurrently or sequentially co-administered with the one or more tyrosine kinase inhibitors.

13. The multimodal cancer therapy of claim 1, wherein the combined administration of the one or more tyrosine kinase inhibitors with the one or more ChNPs provides a synergistic effect in killing cancer cells.

* * * * *